(12) United States Patent
Gardner et al.

(10) Patent No.: US 11,981,680 B2
(45) Date of Patent: May 14, 2024

(54) SUBSTITUTED THIENOPYRROLES AS PAD4 INHIBITORS

(71) Applicant: BRISTOL-MYERS SQUIBB COMPANY, Princeton, NJ (US)

(72) Inventors: Daniel S. Gardner, Furlong, PA (US); John V. Duncia, Newtown, PA (US); Joseph B. Santella, Springfield, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 638 days.

(21) Appl. No.: 17/265,833

(22) PCT Filed: Aug. 7, 2019

(86) PCT No.: PCT/US2019/045426
§ 371 (c)(1),
(2) Date: Feb. 4, 2021

(87) PCT Pub. No.: WO2020/033490
PCT Pub. Date: Feb. 13, 2020

(65) Prior Publication Data
US 2022/0064180 A1 Mar. 3, 2022

Related U.S. Application Data

(60) Provisional application No. 62/715,834, filed on Aug. 8, 2018.

(51) Int. Cl.
C07D 495/04 (2006.01)
A61K 45/06 (2006.01)
C07D 519/00 (2006.01)

(52) U.S. Cl.
CPC ............ *C07D 495/04* (2013.01); *A61K 45/06* (2013.01); *C07D 519/00* (2013.01)

(58) Field of Classification Search
CPC ........................... C07D 495/04; C07D 519/00
See application file for complete search history.

(56) References Cited

U.S. PATENT DOCUMENTS

2019/0276440 A1   9/2019   Zhao

FOREIGN PATENT DOCUMENTS

| WO | 2014015905 A1 | 1/2014 |
|---|---|---|
| WO | 2016185279 A1 | 11/2016 |
| WO | 2017/100601 A1 | 6/2017 |
| WO | 2017108282 A1 | 6/2017 |
| WO | 2017/100594 A1 | 7/2017 |
| WO | 2017147102 A1 | 8/2017 |
| WO | 2018022897 A1 | 2/2018 |
| WO | 2018049296 A1 | 3/2018 |
| WO | 2019077631 A1 | 4/2019 |
| WO | 2019161803 A1 | 8/2019 |
| WO | 2020033488 A1 | 2/2020 |
| WO | 2020033490 A1 | 2/2020 |
| WO | 2020033514 A1 | 2/2020 |
| WO | 2020033520 A1 | 2/2020 |

OTHER PUBLICATIONS

Cancer and Metastasis Reviews (1998), 17(1), 91-106.*
Science (1999), vol. 286, 531-537.*
Cancer [online], retrieved on Sep. 26, 2023. Retrieved from the internet, URL: <https://www.nlm.nih.gov/medlineplus/cancer.html>>).*
Are We Close to a Cure for Chronic Lymphocytic Leukemia? [online]; retrieved on Sep. 26, 2023. Retrieved from the internet, URL https://www.healthline.com/health/cll/cll-cure-are-we-close.*
Guo, et al., Synthesis of reversible PAD4 inhibitors via copper-catalyzed C—H arylation of benzimidazole; Science China Chemistry; the Frontiers of Chemicalbiology and Synthesis, vol. 62, No. 5, pp. 592-596, 2019.
Lange et al., "Peptidylarginine Deiminases as Mediators ofMicrovesicular Release—Novel Therapeutic Interventions" 2017.

* cited by examiner

Primary Examiner — Shawquia Jackson
(74) Attorney, Agent, or Firm — Hong Liu

(57) ABSTRACT

The present invention provides compounds of formula (I) useful as inhibitors of PAD4, compositions thereof, and methods of treating PAD4-related disorders.

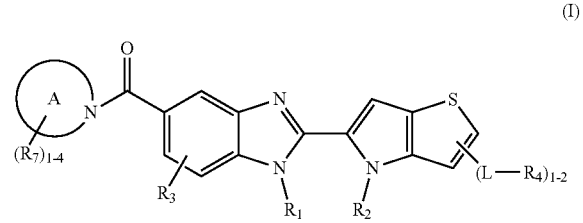

11 Claims, No Drawings

SUBSTITUTED THIENOPYRROLES AS PAD4 INHIBITORS

CROSS REFERENCE TO RELATED APPLICATIONS

This application is a national phase application under 35 U.S.C. § 371 of International Patent Application No. PCT/US2019/045426 filed on Aug. 7, 2019, which is entitled to priority pursuant to 35 U.S.C. § 119€ to U.S. provisional patent application No. 62/715,834, filed Aug. 8, 2018, which is incorporated herein in its entirety.

BACKGROUND OF THE INVENTION

PAD4 is a member of the peptidylarginine deiminase (PAD) family of enzymes capable of catalysing the citrullination of arginine into citrulline within peptide sequences. PAD4 is responsible for the deimination or citrullination of a variety of proteins in vitro and in vivo, with consequences of diverse functional responses in a variety of diseases (Jones J. E. et al, *Curr. Opin. Drug Discov. Devel.*, 12(5), (2009), 616-627). Examples of exemplar diseases include rheumatoid arthritis, diseases with neutrophilic contributions to pathogenesis (for example vasculitis, systemic lupus erythematosus, ulcerative colitis) in addition to oncology indications. PAD4 inhibitors also have wider applicability as tools and therapeutics for human disease through epigenetic mechanisms.

Inhibitors of PAD4 have utility against Rheumatoid Arthritis (RA). RA is an auto-immune disease affecting approximately 1% of the population (Wegner N. et al, *Immunol. Rev.*, 233(1) (2010), 34-54). It is characterised by inflammation of articular joints leading to debilitating destruction of bone and cartilage. A weak genetic association between PAD4 polymorphisms and susceptibility to RA has been suggested, albeit inconsistently, in a number of population studies (Kochi Y. et al, *Ann. Rheum. Dis.*, 70, (2011), 512-515). PAD4 (along with family member PAD2) has been detected in synovial tissue where it is responsible for the deimination of a variety of joint proteins. This process is presumed to lead to a break of tolerance to, and initiation of immune responses to, citrullinated substrates such as fibrinogen, vimentin and collagen in RA joints. These anti-citrullinated protein antibodies (ACPA) contribute to disease pathogenesis and may also be used as a diagnostic test for RA (e.g. the commercially available CCP2 or cyclic citrullinated protein 2 test). In addition, increased citrullination may also offer additional direct contributions to disease pathogenesis through its ability to affect directly the function of several joint and inflammatory mediators (e.g. fibrinogen, anti-thrombin, multiple chemokines). In a smaller subset of RA patients, anti-PAD4 antibodies can be measured and may correlate with a more erosive form of the disease.

PAD4 inhibitors are also useful for the reduction of pathological neutrophil activity in a variety of diseases. Studies suggest that the process of Neutrophil Extracellular Trap (NET) formation, an innate defence mechanism by which neutrophils are able to immobilise and kill pathogens, is associated with histone citrullination and is deficient in PAD4 knockout mice (Neeli J. et al, *J. Immunol.*, 180, (2008), 1895-1902 and Li P. et al, *J. Exp. Med.*, 207(9), (2010), 1853-1862). PAD4 inhibitors may therefore have applicability for diseases where NET formation in tissues contributes to local injury and disease pathology. Such diseases include, but are not limited to, small vessel vasculitis (KessenbrockK. et al, *Nat. Med*, 15(6), (2009), 623-625), systemic lupus erythematosus (Hakkim A. et al, *Proc. Natl. Acad Sci. USA*, 107(21), (2010), 9813-9818 and Villanueva E. et al, *J Immunol.*, 187(1), (2011), 538-52), ulcerative colitis (Savchenko A. et al, *Pathol. Int.*, 61(5), (2011), 290-7), cystic fibrosis, asthma (Dworski R. et al, *J. Allergy Clin. Immunol.*, 127(5), (2011), 1260-6), deep vein thrombosis (Fuchs T. et al, *Proc. Natl. Acad Sci. USA*, 107(36), (2010), 15880-5), periodontitis (Vitkov L. et al, *Ultrastructural Pathol.*, 34(1), (2010), 25-30), sepsis (Clark S. R. et al, *Nat. Med*, 13(4), (2007), 463-9), appendicitis (Brinkmann V. et al, *Science*, 303, (2004), 1532-5), and stroke. In addition, there is evidence that NETs may contribute to pathology in diseases affecting the skin, e.g., in cutaneous lupus erythematosus (Villanueva E. et al, *J. Immunol.*, 187(1), (2011), 538-52) and psoriasis (Lin A. M. et al., *J. Immunol.*, 187(1), (2011), 490-500), so a PAD4 inhibitor may show benefit to tackle NET skin diseases, when administered by a systemic or cutaneous route. PAD4 inhibitors may affect additional functions within neutrophils and have wider applicability to neutrophilic diseases.

Studies have demonstrated efficacy of tool PAD inhibitors (for example chloro-amidine) in a number of animal models of disease, including collagen-induced arthritis (Willis V. C. et al, *J. Immunol.*, 186(7), (2011), 4396-4404), dextran sulfate sodium (DSS)-induced experimental colitis (Chumanevich A. A. et al, *Am. J. Physiol. Gastrointest. Liver Physiol.*, 300(6), (2011), G929-G938), spinal cord repair (Lange S. et al, *Dev. Biol.*, 355(2), (2011), 205-14), and experimental autoimmune encephalomyelitis (EAE). The DSS colitis report also demonstrates that chloro-amidine drives apoptosis of inflammatory cells both in vitro and in vivo, suggesting that PAD4 inhibitors may be effective more generally in widespread inflammatory diseases.

PAD4 inhibitors are also useful in the treatment of cancers (Slack J. L. et al, *Cell. Mol. Life Sci.*, 68(4), (2011), 709-720). Over-expression of PAD4 has been demonstrated in numerous cancers (Chang X et al, *BMC Cancer*, 9, (2009), 40). An antiproliferative role has been suggested for PAD4 inhibitors from the observation that PAD4 citrullinates arginine residues in histones at the promoters of p53-target genes such as p21, which are involved in cell cycle arrest and induction of apoptosis (Li P. et al, *Mol. Cell Biol.*, 28(15), (2008), 4745-4758).

The aforementioned role of PAD4 in deiminating arginine residues in histones may be indicative of a role for PAD4 in epigenetic regulation of gene expression. PAD4 is the primary PAD family member observed to be resident in the nucleus as well as the cytoplasm. Early evidence that PAD4 may act as a histone demethyliminase as well as a deiminase is inconsistent and unproven. However, it may reduce histone arginine methylation (and hence epigenetic regulation associated with this mark) indirectly via depletion of available arginine residues by conversion to citrulline. PAD4 inhibitors are useful as epigenetic tools or therapeutics for affecting expression of varied target genes in additional disease settings. Through such mechanisms, PAD4 inhibitors may also be effective in controlling citrullination levels in stem cells and may therefore therapeutically affect the pluripotency status and differentiation potential of diverse stem cells including, but not limited to, embryonic stem cells, neural stem cells, haematopoietic stem cells and cancer stem cells. Accordingly, there remains an unmet need to identify and develop PAD4 inhibitors for the treatment of PAD4-mediated disorders.

SUMMARY OF THE INVENTION

It has now been found that compounds of Formula (I) are useful as inhibitors of PAD4:

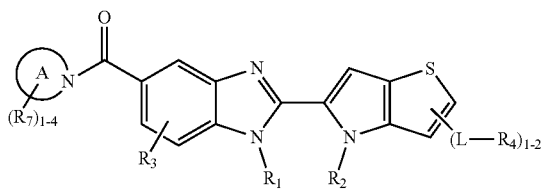

(I)

wherein each of Ring A, $R_1$, $R_2$, $R_3$, L, $R_4$, $R_7$, and other variables is as defined herein.

In some embodiments, a provided compound demonstrates selectivity for PAD4 with respect to PAD2. The present invention also provides pharmaceutically acceptable compositions comprising a provided compound. Provided compounds are useful in treatment of various disorders associated with PAD4. Such disorders are described in detail, herein, and include, for example rheumatoid arthritis, vasculitis, systemic lupus erythematosus, ulcerative colitis, cancer, cystic fibrosis, asthma, cutaneous lupus erythematosus, and psoriasis.

DETAILED DESCRIPTION OF THE INVENTION

1. General Description of Certain Aspects of the Invention

In some embodiments, such compounds include those of the formulae described herein, or a pharmaceutically acceptable salt thereof, wherein each variable is as defined herein and described in embodiments. Such compounds have the structure of Formula (I):

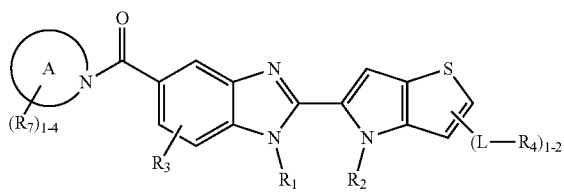

(I)

or a pharmaceutically acceptable salt thereof, wherein:
Ring A is 4- to 15-membered heterocyclyl substituted with 1-4 $R_7$;
$R_1$ is selected from $CH_3$ and $CD_3$;
$R_2$ is selected from H, $C_{1-3}$ alkyl substituted with 0-5 $R_e$, —$(CH_2)_r$—$C_{3-6}$ cycloalkyl with 0-5 $R_e$;
L is selected from —$(CR_dR_d)_{0-3}$—, —$NR_d$—, —$S(O)_p$—, and —$C(=O)$—;
$R_3$ is selected from H, F, Cl, Br, and —$OR_b$;
$R_4$ is selected from H, F, Cl, Br, —CN, —$OR_b$, $C_{1-6}$ alkyl substituted with 1-5 $R_5$, aryl substituted with 1-5 $R_5$, $C_{3-12}$ cycloalkyl substituted with 1-5 $R_5$, and heterocyclyl comprising carbon atoms and 1-3 heteroatoms selected from N, $NR_6$, O, and S and substituted with 1-5 $R_5$;
$R_5$, at each occurrence, is independently selected from H, F, Cl, Br, $C_{1-4}$alkyl substituted with 0-4 $R_e$, $C_{2-4}$alkenyl substituted with 0-4 $R_e$, $C_{2-4}$alkynyl substituted with 0-4 $R_e$, nitro, —$(CH_2)_rS(O)_pR_c$, —$(CH_2)_rS(O)_pNR_aR_a$, —$(CH_2)_rNR_aS(O)_pR_c$, —$(CH_2)_rOR_b$, —$(CH_2)_r$CN, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_rC(=O)NR_aR_a$, —$P(=O)(OC_{1-4}alkyl)_2$, —$P(=O)(C_{1-4}alkyl)_2$, $C_{3-6}$cycloalkyl substituted with 0-4 $R_e$, aryl substituted with 0-4 $R_e$, heterocyclyl substituted with 0-4 $R_e$, and heteroaryl substituted with 0-4 $R_e$;
$R_6$, at each occurrence, is independently selected from H, $C_{1-3}$alkyl substituted with 0-5 $R_e$, —$S(O)_pR_c$, —$C(=O)R_b$, —$C(=O)(CH_2)_rNR_aR_a$, —$C(=O)(CH_2)_rNR_aC(=O)R_b$, —$C(=O)OR_b$, —$S(O)_pNR_aR_a$, —$(CH_2)_r$—$C_{3-6}$cycloalkyl substituted with 0-4 $R_e$, —$(CH_2)_r$-aryl substituted with 0-4 $R_e$, —$(CH_2)_r$-heterocyclyl substituted with 0-4 $R_e$, and —$(CH_2)_r$-heteroaryl substituted with 0-4 $R_e$;
$R_7$ is selected from H, F, Cl, CN, $C_{1-3}$ alkyl, =N—$OR_b$, —$(CH_2)_rOR_b$, —$(CH_2)_rNR_aR_a$, —$NR_aC(=NH)C_{1-3}$ alkyl, —$NR_aC(=O)OR_b$, carbocyclyl, and a heterocyclyl; alternatively, two $R_7$ groups are taken together to form carbocyclyl or heterocyclyl;
$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —$(CH_2)_r$—$C_{3-6}$ carbocyclyl substituted with 0-5 $R_e$, and —$(CH_2)_r$-heterocyclyl substituted with 0-5 $R_e$;
$R_d$, at each occurrence, is independently selected from H and $C_{1-6}$ alkyl substituted with 0-5 $R_e$;
$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-aryl, F, Cl, Br, CN, $NO_2$, =O, —$C(=O)OH$, —$C(=O)OC_{1-4}$ alkyl, —$(CH_2)_rOH$, and —$(CH_2)_rOC_{1-4}$alkyl;
$R_f$, at each occurrence, is independently selected from H, F, Cl, Br, CN, OH, $C_{1-5}$ alkyl optionally substituted with OH, $C_{3-6}$ cycloalkyl, and phenyl;
p, at each occurrence, is independently selected from zero, 1, and 2;
r, at each occurrence, is independently selected from zero, 1, 2, 3, and 4; and
provided when L is selected from —$NR_d$—, —$S(O)_p$—, and —$C(=O)$—, $R_4$ is selected from aryl substituted with 1-5 $R_5$, $C_{3-12}$ cycloalkyl substituted with 1-5 $R_5$, and heterocyclyl comprising carbon atoms and 1-3 heteroatoms selected from N, $NR_6$, O, and S and substituted with 1-5 $R_5$.

2. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For examples, "$C_1$ to $C_{12}$ alkyl" or "$C_{1-12}$ alkyl" (or alkylene), is intended to include $C_1$, $C_2$, $C_3$, $C_4$, $C_5$, $C_6$, $C_7$, $C_8$, $C_9$, $C_{10}$, $C_{11}$ and $C_{12}$ alkyl groups; "$C_4$ to $C_{15}$ alkyl" or "$C_{4-18}$ alkyl" (or alkylene), is intended to include $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 15th Edition, John Wiley & Sons, Inc., New York (2007). "$C_{6-10}$ aryl" refers to phenyl and naphthyl.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N—O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium ($Na^+$), potassium ($K^+$), ammonium ($R_nNH_m+$ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis,* 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy*, 22nd Edition, Pharmaceutical Press, London, UK (2012), the disclosure of which is hereby incorporated by reference.

In addition, compounds of Formula (I) may have prodrug forms. Any compound that will be converted in vivo to provide the bioactive agent (i.e., a compound of Formula (I)) is a prodrug within the scope and spirit of the invention. Various forms of prodrugs are well known in the art. For examples of such prodrug derivatives, see:
  a) Bundgaard, H., ed., *Design of Prodrugs*, Elsevier (1985), and Widder, K. et al., eds., *Methods in Enzymology*, 112:309-396, Academic Press (1985);
  b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);
  c) Bundgaard, H., *Adv. Drug Deliv. Rev.*, 8:1-38 (1992);
  d) Bundgaard, H. et al., *J. Pharm. Sci.*, 77:285 (1988);
  e) Kakeya, N. et al., *Chem. Pharm. Bull.*, 32:692 (1984); and
  f) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield Formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

The terms "measurable affinity" and "measurably inhibit," as used herein, means a measurable change in PAD4 activity between a sample comprising a compound of the present invention, or composition thereof, and PAD4, and an equivalent sample comprising PAD4 in the absence of said compound, or composition thereof.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", "Z" and "ee" are stereochemical designations familiar to one skilled in the art. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

AcOH or HOAc acetic acid
ACN acetonitrile
Alk Alkyl
AlMe$_3$ Trimethylaluminum
BBr$_3$ boron tribromide
Bn benzyl
Boc tert-butyloxycarbonyl BOP reagent benzotriazol-1-yloxytris(dimethylamino)
   phosphonium hexafluorophosphate
Bu butyl
i-Bu isobutyl
t-Bu tert-butyl
t-BuOH tert-butanol
Cbz carbobenzyloxy
$CDCl_3$ deutero-chloroform
$CD_3OD$ deutero-methanol
$CH_2Cl_2$ dichloromethane
$CH_3CN$ acetonitrile
$CHCl_3$ chloroform
DCM dichloromethane
DIEA, DIPEA or diisopropylethylamine
   Hunig's base
DMF dimethyl formamide
DMSO dimethyl sulfoxide
Et ethyl
$Et_3N$ or TEA triethylamine
$Et_2O$ diethyl ether
EtOAc ethyl acetate
EtOH ethanol
HCl hydrochloric acid
HPLC high-performance liquid chromatography
$K_2CO_3$ potassium carbonate
$K_2HPO_4$ potassium hydrogenphosphate
LCMS liquid chromatography mass spectrometry
LiHMDS lithium bis(trimethylsilyl)amide
LG leaving group
Me methyl
MeOH methanol
$MgSO_4$ magnesium sulfate
MsOH or MSA methylsulfonic acid
NaCl sodium chloride
$Na_2CO_3$ sodium carbonate
$NaHCO_3$ sodium bicarbonate
NaOH sodium hydroxide
$Na_2SO_4$ sodium sulfate
$NH_3$ ammonia
$NH_4Cl$ ammonium chloride
$NH_4OAc$ ammonium acetate
$Pd(OAc)_2$ palladium(II) acetate
$Pd(dppf)Cl_2$ [1,1'-Bis(diphenylphosphino)ferrocene]palladium(II) dichloride
$Pd(PPh_3)_4$ tetrakis(triphenylphosphine)palladium(O)
PG protecting group
Ph phenyl
Pr propyl
i-Pr isopropyl
i-PrOH or IPA isopropanol
Rt retention time
$SiO_2$ silica oxide
SFC supercritical fluid chromatography
TBAI Tetrabutylammonium iodide
TEA triethylamine
TFA trifluoroacetic acid
TFAA Trifluoroacetic anhydride
THF tetrahydrofuran
$TiCl_4$ titanium tetrachloride
T3P 1-propanephosphonic acid cyclic anhydride 3. Description of Exemplary Compounds In a first aspect, the present invention provides a compound of Formula (I):

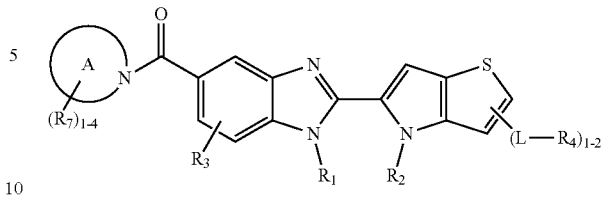

or a pharmaceutically acceptable salt thereof, wherein:
Ring A is 4- to 15-membered heterocyclyl substituted with 1-4 $R_7$;
$R_1$ is selected from $CH_3$ and $CD_3$;
$R_2$ is selected from H, $C_{1-3}$ alkyl substituted with 0-5 $R_e$, and $-(CH_2)_r-C_{3-6}$ cycloalkyl with 0-5 $R_e$;
$R_3$ is selected from H, F, Cl, Br, and $-OR_b$;
L is selected from $-(CR_dR_d)_{0-3}-$, $-NR_a-$, $-S(O)_p-$, and $-C(=O)-$;
$R_4$ is selected from H, F, Cl, Br, $-CN$, $-OR_b$, $C_{1-6}$ alkyl substituted with 1-5 $R_5$, aryl substituted with 1-5 $R_5$, $C_{3-12}$ cycloalkyl substituted with 1-5 $R_5$, and heterocyclyl comprising carbon atoms and 1-3 heteroatoms selected from N, $NR_6$, O, and S and substituted with 1-5 $R_5$;
$R_5$, at each occurrence, is independently selected from H, F, Cl, Br, $C_{1-4}$alkyl substituted with 0-4 $R_e$, $C_{2-4}$alkenyl substituted with 0-4 $R_e$, $C_{2-4}$alkynyl substituted with 0-4 $R_e$, nitro, $-(CH_2)_rS(O)_pR_c$, $-(CH_2)_rS(O)_pNR_aR_a$, $-(CH_2)_rNR_aS(O)_pR_c$, $-(CH_2)_rOR_b$, $-(CH_2)_rCN$, $-(CH_2)_rNR_aR_a$, $-(CH_2)_rNR_aC(=O)R_b$, $-(CH_2)_rNR_aC(=O)NR_aR_a$, $-(CH_2)_rC(=O)OR_b$, $-(CH_2)_rC(=O)R_b$, $-(CH_2)_rOC(=O)R_b$, $-(CH_2)_rC(=O)NR_aR_a$, $-P(=O)(OC_{1-4}alkyl)_2$, $-P(=O)(C_{1-4}alkyl)_2$, $C_{3-6}$cycloalkyl substituted with 0-4 $R_e$, aryl substituted with 0-4 $R_e$, heterocyclyl substituted with 0-4 $R_e$, and heteroaryl substituted with 0-4 $R_e$;
$R_6$, at each occurrence, is independently selected from H, $C_{1-3}$alkyl substituted with 0-5 $R_e$, $-S(O)_pR_c$, $-C(=O)R_b$, $-C(=O)(CH_2)_rNR_aR_a$, $-C(=O)(CH_2)_rNR_aC(=O)R_b$, $-C(=O)OR_b$, $-S(O)_pNR_aR_a$, $-(CH_2)_r-C_{3-6}$cycloalkyl substituted with 0-4 $R_e$, $-(CH_2)_r$-aryl substituted with 0-4 $R_e$, $-(CH_2)_r$-heterocyclyl substituted with 0-4 $R_e$, and $-(CH_2)_r$-heteroaryl substituted with 0-4 $R_e$;
$R_7$ is selected from H, F, Cl, CN, $C_{1-3}$ alkyl, $=N-OR_b$, $-(CH_2)_rOR_b$, $-(CH_2)_rNR_aR_a$, $-NR_aC(=NH)C_{1-3}$ alkyl, $-NR_aC(=O)OR_b$, carbocyclyl, and heterocyclyl; alternatively, two $R_7$ groups are taken together to form carbocyclyl or heterocyclyl;
$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;
$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;
$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —(CH$_2$)$_r$—C$_{3-6}$ carbocyclyl substituted with 0-5 R$_e$, and —(CH$_2$)$_r$-heterocyclyl substituted with 0-5 R$_e$;

R$_d$, at each occurrence, is independently selected from H and C$_{1-6}$ alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$-aryl, F, Cl, Br, CN, NO$_2$, =O, —C(=O)OH, —C(=O)OC$_{1-4}$ alkyl, —(CH$_2$)$_r$OH, and —(CH$_2$)$_r$OC$_{1-4}$alkyl;

R$_f$, at each occurrence, is independently selected from H, F, Cl, Br, CN, OH, C$_{1-5}$ alkyl optionally substituted with OH, C$_{3-6}$ cycloalkyl, and phenyl;

p, at each occurrence, is independently selected from zero, 1, and 2;

r, at each occurrence, is independently selected from zero, 1, 2, 3, and 4; and provided when L is selected from —NR$_a$—, —S(O)$_p$—, and —C(=O)—, R$_4$ is selected from aryl substituted with 1-5 R$_5$, C$_{3-12}$ cycloalkyl substituted with 1-5 R$_5$, and heterocyclyl comprising carbon atoms and 1-3 heteroatoms selected from N, NR$_6$, O, and S and substituted with 1-5 R$_5$.

In a second aspect, the present invention provides a compound of Formula (II):

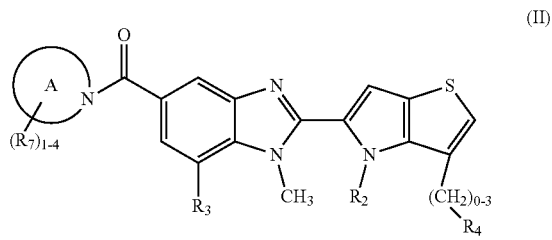

(II)

or a pharmaceutically acceptable salt thereof, within the scope of the first aspect, wherein: Ring A is selected from

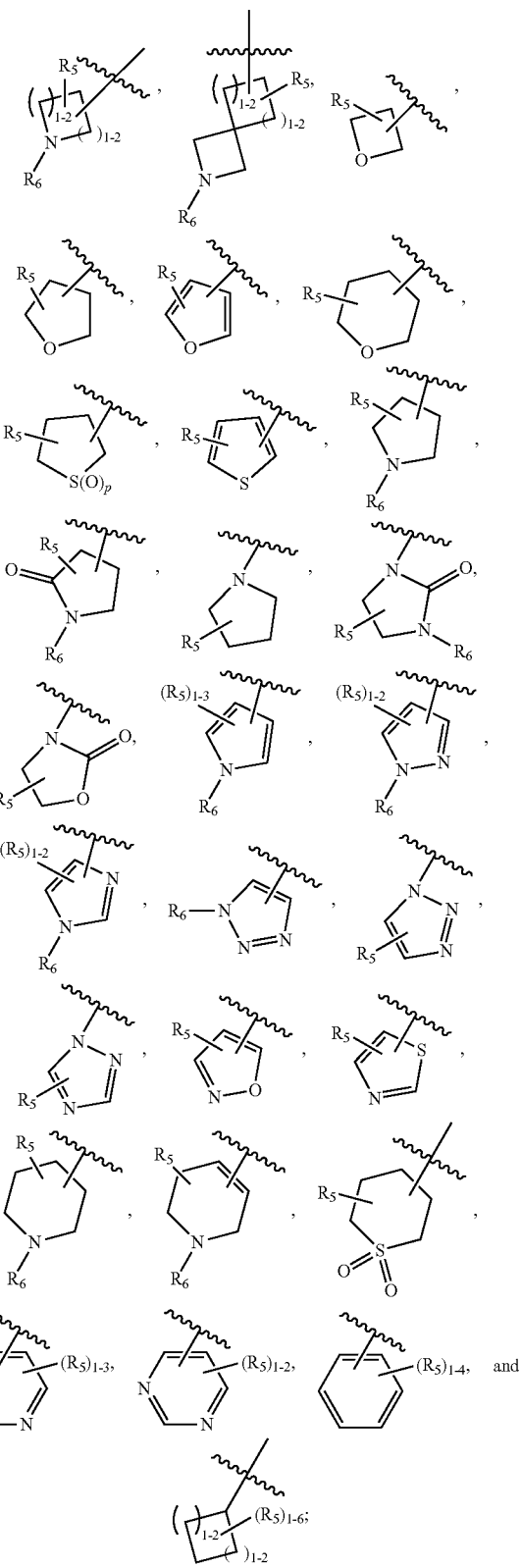

R$_2$ is selected from —CH$_3$, —CH$_2$CH$_3$, and —CH$_2$-cyclopropyl;

R$_3$ is selected from H, F, Cl, Br, and —OC$_{1-4}$ alkyl;

R$_4$ is selected from F, Cl, Br, C$_{1-5}$ alkyl substituted with 1-4 R$_5$

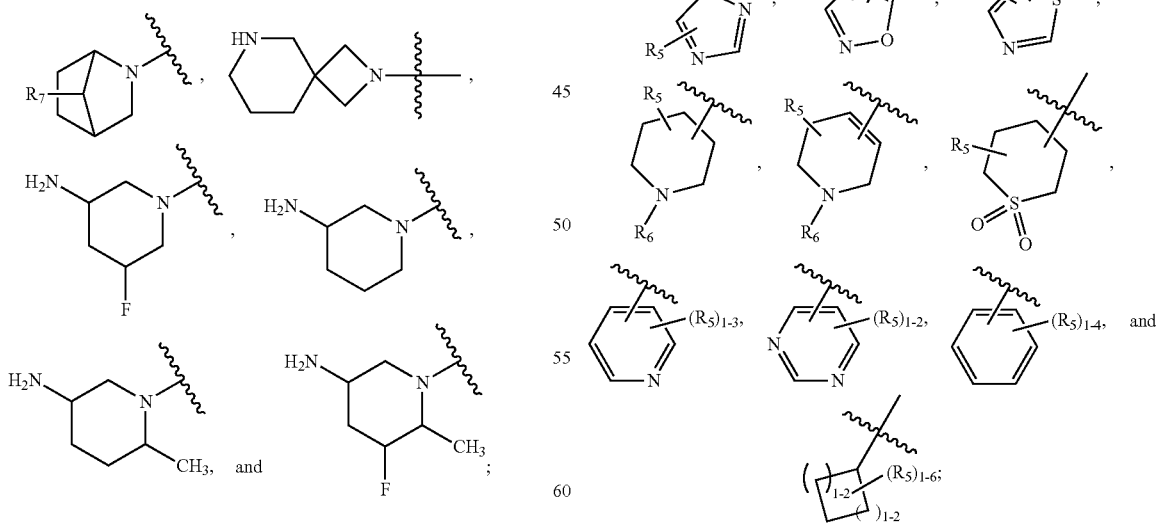

R$_5$, at each occurrence, is independently selected from H, F, Cl, Br, C$_{1-4}$alkyl, C$_{2-4}$alkenyl, C$_{2-4}$alkynyl, nitro, —S(O)$_p$R$_c$, —S(O)$_p$NR$_a$R$_a$, —NR$_a$S(O)$_p$R$_c$, —OR$_b$, —CN, —NR$_a$R$_a$, —NR$_a$C(=O)R$_b$, —NR$_a$C(=O)

NR$_a$R$_a$, —C(=O)OR$_b$, —C(=O)R$_b$, —OC(=O)R$_b$, —C(=O)NR$_a$R$_a$, P(=O)(C$_{1-4}$alkyl)$_2$, C$_{3-6}$cycloalkyl substituted with 0-4 R$_e$, aryl substituted with 0-4 R$_e$, heterocyclyl substituted with 0-4 R$_e$, and heteroaryl substituted with 0-4 R$_e$;

R$_6$, at each occurrence, is independently selected from H, C$_{1-3}$alkyl substituted with 0-5 R$_e$, —S(O)$_p$R$_c$, —C(=O)R$_b$, —C(=O)NR$_a$R$_a$, —C(=O)OR$_b$, —S(O)$_p$NR$_a$R$_a$, —(CH$_2$)$_r$—C$_{3-6}$cycloalkyl substituted with 0-4 R$_e$, —(CH$_2$)$_r$-aryl substituted with 0-4 R$_e$, —(CH$_2$)$_r$-heterocyclyl substituted with 0-4 R$_e$, and —(CH$_2$)$_r$-heteroaryl substituted with 0-4 R$_e$;

R$_a$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$ alkynyl substituted with 0-5 R$_e$, —(CH$_2$)$_r$—C$_{3-6}$ carbocyclyl substituted with 0-5 R$_e$, and —(CH$_2$)$_r$-heterocyclyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$-aryl, F, Cl, Br, CN, NO$_2$, =O, C(=O)OH, —C(=O)OC$_{1-4}$ alkyl, —(CH$_2$)$_r$OH, and —(CH$_2$)$_r$OC$_{1-4}$alkyl;

R$_f$, at each occurrence, is independently selected from H, F, Cl, Br, CN, OH, C$_{1-5}$ alkyl optionally substituted with OH, C$_{3-6}$ cycloalkyl, and phenyl;

p, at each occurrence, is independently selected from zero, 1, and 2; and r, at each occurrence, is independently selected from zero, 1, 2, 3, and 4.

In a third aspect, the present invention provides a compound of Formula (III):

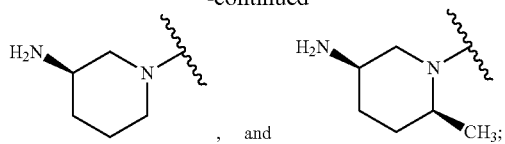

or a pharmaceutically acceptable salt thereof, wherein:
Ring A is selected from

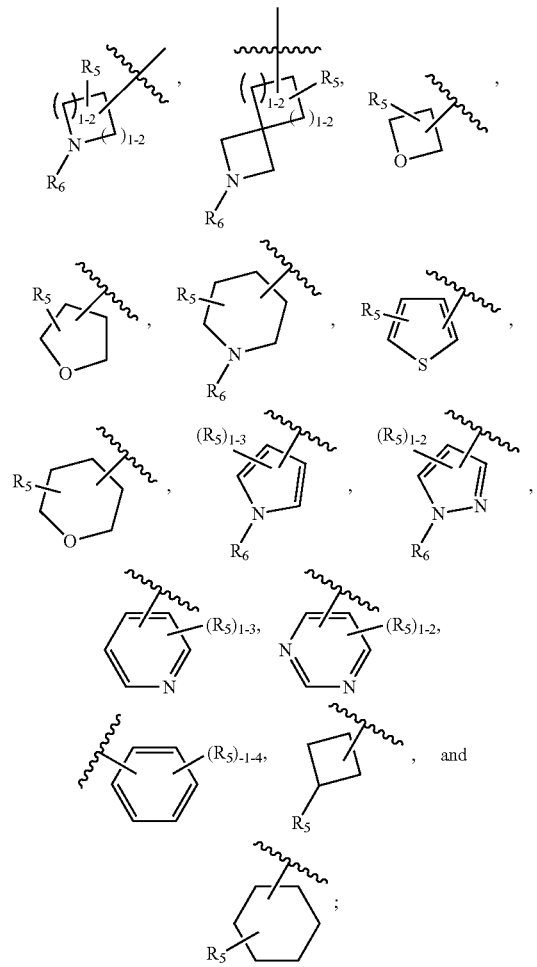

R$_2$ is selected from —CH$_3$, and —CH$_2$-cyclopropyl;
R$_3$ is —OC$_{1-4}$ alkyl;
R$_4$ is selected from R$_5$, at each occurrence, is independently selected from H, F, Cl, Br, C$_{1-4}$alkyl, —OR$_b$, —CN, —S(O)$_p$R$_c$, —S(O)$_p$ NR$_a$R$_a$, —NR$_a$S(O)$_p$R$_c$, —NR$_a$C(=O)NR$_a$R$_a$, —C(=O)OR$_b$, —C(=O)R$_b$, —OC(=O)R$_b$, —C(=O)NR$_a$R$_a$, and NHC(=O)R$_b$;

R$_6$, at each occurrence, is independently selected from H, C$_{1-3}$alkyl substituted with 0-5 R$_e$, —C(=O)R$_b$, —C(=O)OR$_b$,

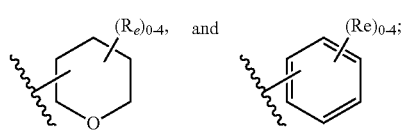

R$_a$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$-aryl, F, Cl, Br;

R$_f$, at each occurrence, is independently selected from H, F, Cl, Br, CN, OH, C$_{1-5}$ alkyl optionally substituted with OH, C$_{3-6}$ cycloalkyl, and phenyl;

r, at each occurrence, is independently selected from zero, 1, 2, 3, and 4.

In a fourth aspect, the present invention provides a compound or a pharmaceutically acceptable salt thereof, wherein:

Ring A is

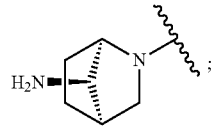

R$_2$ is selected from —CH$_3$ and —CH$_2$-cyclopropyl;
R$_3$ is —OCH$_3$;
R$_4$ is selected from

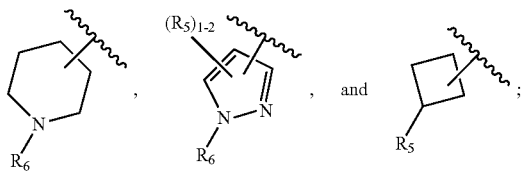

R$_5$, at each occurrence, is independently selected from H, C$_{1-4}$ alkyl, CN, OH, —C(=O)NR$_a$R$_a$, and NHC(=O)C$_{1-4}$ alkyl; and R$_6$, at each occurrence, is independently selected from H, methyl, ethyl, and —C(=O)C$_{1-4}$ alkyl.

In a fifth aspect, the present invention provides a compound of Formula (IV):

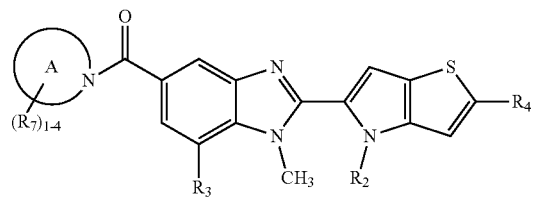

(IV)

or a pharmaceutically acceptable salt thereof, within the scope of the first aspect, wherein:

Ring A is selected from

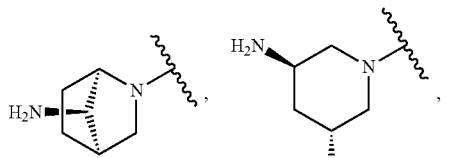

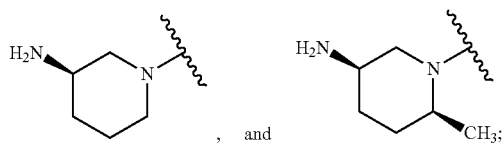

R$_2$ is selected from —CH$_3$, —CH$_2$CH$_3$, and —CH$_2$-cyclopropyl;

R$_3$ is selected from H, F, Cl, Br, and —OC$_{1-4}$ alkyl;

R$_4$ is selected from H, F, Cl, Br, C$_{1-3}$ alkyl substituted with 0-4 R$_e$,

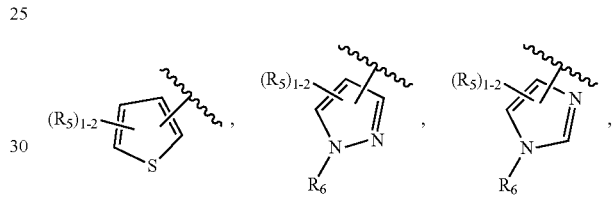

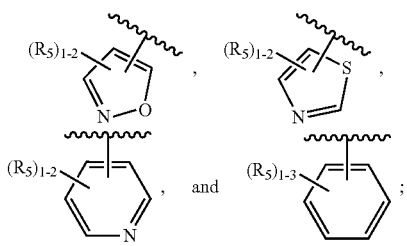

R$_5$, at each occurrence, is independently selected from H, F, Cl, Br, C$_{1-4}$alkyl;

R$_6$, at each occurrence, is independently selected from H, C$_{1-6}$ alkyl substituted with 0-5 R$_e$, —(CH$_2$)$_r$-aryl substituted with 0-4 R$_e$, and —(CH$_2$)$_r$-heterocyclyl substituted with 0-4 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, —(CH$_2$)$_r$-aryl, F, Cl, Br, CN, NO$_2$, =O, C(=O)OH, —C(=O)OC$_{1-4}$ alkyl, —(CH$_2$)$_r$OH, and —(CH$_2$)$_r$OC$_{1-4}$alkyl;

R$_f$, at each occurrence, is independently selected from H, F, Cl, Br, CN, OH, C$_{1-5}$ alkyl optionally substituted with OH, C$_{3-6}$ cycloalkyl, and phenyl; and r, at each occurrence, is independently selected from zero, 1, 2, 3, and 4.

In a sixth aspect, the present invention provides a compound or a pharmaceutically acceptable salt thereof, within the scope of the fifth aspect, wherein:

Ring A is selected from

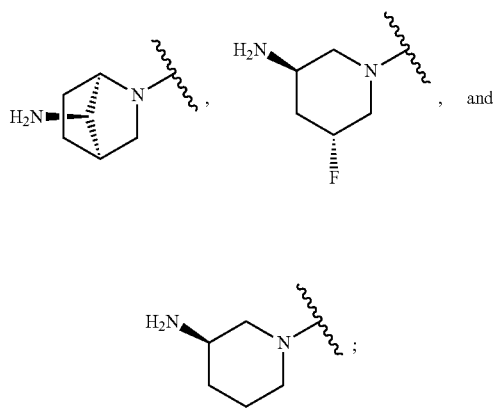

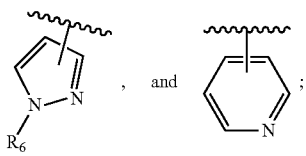

$R_2$ is —$CH_2$-cyclopropyl;
$R_3$ is —$OC_{1-4}$ alkyl;
$R_4$ is selected from H, F, Cl, Br, $C_{1-3}$ alkyl,

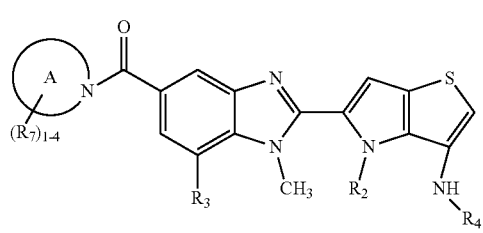

and $R_6$ is selected from H and $C_{1-3}$ alkyl.

In a seventh aspect, the present invention provides a compound or a pharmaceutically acceptable salt thereof, within the scope of the second aspect, wherein:

L is —$(CHR_d)_0$—;
$R_4$ is $C_{1-5}$ alkyl substituted with 1-3 $R_5$;
$R_5$, at each occurrence, is independently selected from H, F, Cl, Br, $C_{1-4}$alkyl, —$OR_b$, —CN, —$NR_aR_a$, and —$C(=O)NR_aR_a$;
$R_a$, at each occurrence, is independently selected from H, and $C_{1-6}$ alkyl; and
$R_b$, at each occurrence, is independently selected from H and $C_{1-6}$ alkyl.

In an eighth aspect, the present invention provides a compound of Formula (V):

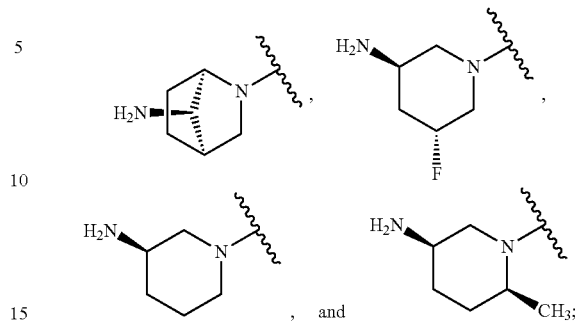

or a pharmaceutically acceptable salt thereof, within the scope of the third aspect, wherein:

Ring A is selected from

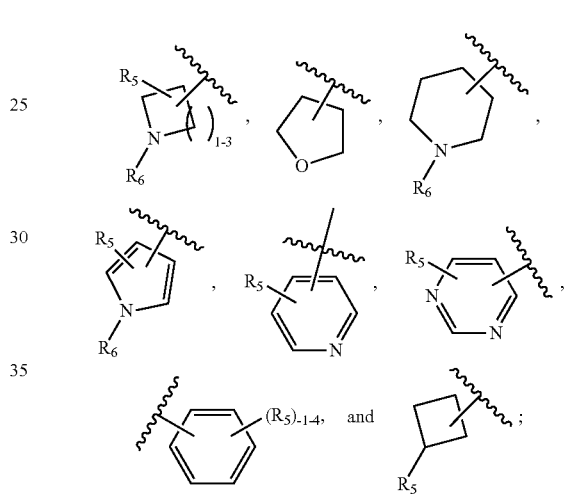

$R_2$ is selected from —$CH_3$ and —$CH_2$-cyclopropyl;
$R_3$ is —$OC_{1-4}$ alkyl;
$R_4$ is selected from $R_5$, at each occurrence, is independently selected from H, F, Cl, Br, $C_{1-4}$alkyl, —$OR_b$, —CN, —$C(=O)NR_aR_a$ and $NHC(=O)R_b$;
$R_6$, at each occurrence, is independently selected from H, $C_{1-3}$ alkyl, —$C(=O)R_b$, and —$C(=O)OR_b$;
$R_a$, at each occurrence, is independently selected from H, and $C_{1-6}$ alkyl; and
$R_b$, at each occurrence, is independently selected from H and $C_{1-6}$ alkyl.

In a ninth aspect, the present invention provides a compound of Formula (I), or a pharmaceutically acceptable salt thereof, wherein: Ring A is 4- to 15-membered heterocyclyl substituted with 1-4 $R_7$;
$R_1$ is selected from $CH_3$ and $CD_3$;
$R_2$ is selected from H, $C_{1-3}$ alkyl substituted with 0-5 $R_e$, and —$(CH_2)_r$—$C_{3-6}$ cycloalkyl with 0-5 $R_e$;
$R_3$ is selected from F, Cl, Br, and —$OR_b$;
L is selected from —$(CR_dR_d)_{0-3}$—, —$NR_a$—, —$S(O)_p$—, and —$C(=O)$—;
$R_4$ is selected from H, F, Cl, Br, —CN, —$OR_b$, $C_{1-6}$ alkyl substituted with 1-5 $R_5$, aryl substituted with 1-5 $R_5$, $C_{3-12}$ cycloalkyl substituted with 1-5 $R_5$, and heterocyclyl comprising carbon atoms and 1-3 heteroatoms selected from N, $NR_6$, O, and S and substituted with 1-5 $R_5$;

R₅, at each occurrence, is independently selected from H, F, Cl, Br, nitro, =O, —C₁₋₄alkyl substituted with 0-4 R_e, C₂₋₄alkenyl substituted with 0-4 R_e, C₂₋₄alkynyl substituted with 0-4 R_e, —(CH₂)_rCN, —(CH₂)_rOR_b, (CH₂)_rS(O)_pR_c, —(CH₂)_rS(O)_pNR_aR_a, —(CH₂)_rNR_aS (O)_pR_c, —(CH₂)_rNR_aR_a, —(CH₂)_rNR_aC(=O)R_b, —(CH₂)_rNR_aC(=O)NR_aR_a, —(CH₂)_rC(=O)OR_b, —(CH₂)_rC(=O)R_b, —(CH₂)_rOC(=O)R_b, —(CH₂)_rC (=O)NR_aR_a, —P(=O)(OC₁₋₄alkyl)₂, —P(=O)(C₁₋₄ alkyl)₂, C₃₋₆cycloalkyl substituted with 0-4 R_e, aryl substituted with 0-4 R_e, heterocyclyl substituted with 0-4 R_e, and heteroaryl substituted with 0-4 R_e;

R₆, at each occurrence, is independently selected from H, C₁₋₃alkyl substituted with 0-5 R_e, —C(=O)R_b, —C(=O)(CH₂)_rNR_aR_a, —C(=O)(CH₂)_rNR_aC(=O) R_b, —C(=O)OR_b, —S(O)_pR_e, —S(O)_pNR_aR_a, —(CH₂)_r—C₃₋₆cycloalkyl substituted with 0-4 R_e, —(CH₂)_r-aryl substituted with 0-4 R_e, —(CH₂)_r-heterocyclyl substituted with 0-4 R_e, and —(CH₂)_r-heteroaryl substituted with 0-4 R_e;

R₇ is selected from H, F, Cl, CN, C₁₋₃ alkyl, =N—OR_b, —(CH₂)_rOR_b, —(CH₂)_rNR_aR_a, —NR_aC(=NH)C₁₋₃ alkyl, —NR_aC(=O)OR_b, carbocyclyl, and a heterocyclyl; alternatively, two R₇ groups are taken together to form carbocyclyl or heterocyclyl;

R_a, at each occurrence, is independently selected from H, C₁₋₆ alkyl substituted with 0-5 R_e, C₂₋₆ alkenyl substituted with 0-5 R_e, C₂₋₆ alkynyl substituted with 0-5 R_e, —(CH₂)_r—C₃₋₁₀carbocyclyl substituted with 0-5 R_e, and —(CH₂)_r-heterocyclyl substituted with 0-5 R_e; or R_a and R_a together with the nitrogen atom to which they are both attached form a heterocyclic ring substituted with 0-5 R_e;

R_b, at each occurrence, is independently selected from H, C₁₋₆ alkyl substituted with 0-5 R_e, C₂₋₆ alkenyl substituted with 0-5 R_e, C₂₋₆ alkynyl substituted with 0-5 R_e, —(CH₂)_r—C₃₋₁₀carbocyclyl substituted with 0-5 R_e, and —(CH₂)_r-heterocyclyl substituted with 0-5 R_e;

R_c, at each occurrence, is independently selected from C₁₋₆ alkyl substituted with 0-5 R_e, C₂₋₆alkenyl substituted with 0-5 R_e, C₂₋₆ alkynyl substituted with 0-5 R_e, —(CH₂)_r—C₃₋₆ carbocyclyl substituted with 0-5 R_e, and —(CH₂)_r-heterocyclyl substituted with 0-5 R_e;

R_d, at each occurrence, is independently selected from H and C₁₋₆ alkyl substituted with 0-5 R_e;

R_e, at each occurrence, is independently selected from C₁₋₆ alkyl substituted with 0-5 R_f, C₂₋₆ alkenyl, C₂₋₆ alkynyl, —(CH₂)_r—C₃₋₆ cycloalkyl, —(CH₂)_r-aryl, F, Cl, Br, CN, NO₂, =O, —C(=O)OH, —C(=O)OC₁₋₄ alkyl, —(CH₂)_rOH, and —(CH₂)_rOC₁₋₄alkyl;

R_f, at each occurrence, is independently selected from H, F, Cl, Br, CN, OH, C₁₋₅ alkyl optionally substituted with OH, C₃₋₆ cycloalkyl, and phenyl;

p, at each occurrence, is independently selected from zero, 1, and 2;

r, at each occurrence, is independently selected from zero, 1, 2, 3, and 4; and provided when L is selected from —NR_a—, —S(O)_p—, and —C(=O)—, R₄ is selected from aryl substituted with 1-5 R₅, C₃₋₁₂ cycloalkyl substituted with 1-5 R₅, and heterocyclyl comprising carbon atoms and 1-3 heteroatoms selected from N, NR₆, O, and S and substituted with 1-5 R₅.

In a tenth aspect, the present invention provides a compound of Formula (II): or a pharmaceutically acceptable salt thereof, wherein:

Ring A is selected from

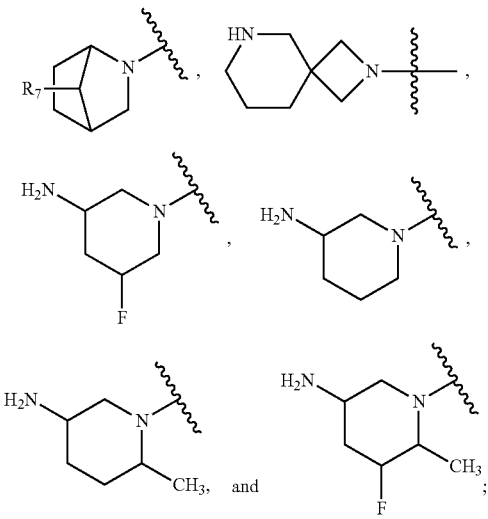

R₂ is selected from —CH₃, —CH₂CH₃, and —CH₂-cyclopropyl;

R₃ is selected from H, F, Cl, Br, and —OC₁₋₄ alkyl;

R₄ is selected from F, Cl, Br, C₁₋₅ alkyl substituted with 1-4 R₅,

R₄ is

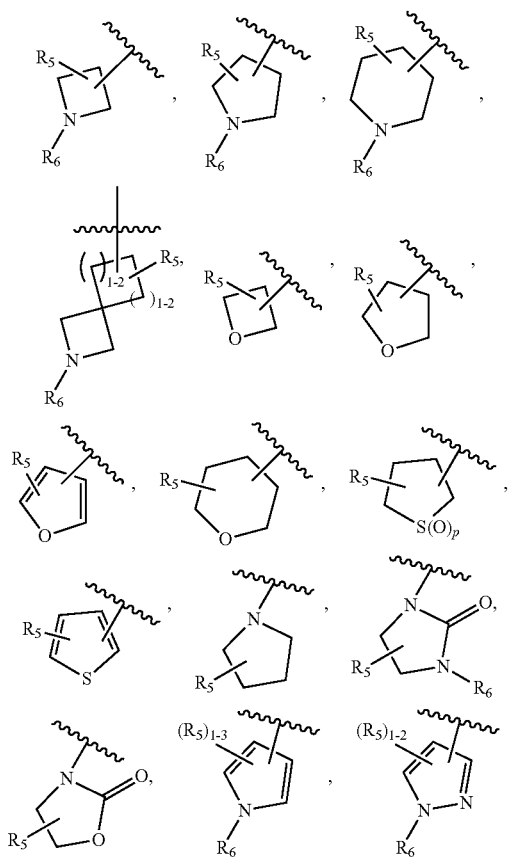

-continued

[chemical structures showing various heterocyclic rings including imidazole, triazole, pyrazole, isoxazole, thiazole, piperidine, thiane dioxide, pyridine, pyrazine, phenyl, and cycloalkyl groups with R₅ and R₆ substituents]

$R_5$, at each occurrence, is independently selected from H, F, Cl, Br, $C_{1-4}$alkyl, $C_{2-4}$alkenyl, $C_{2-4}$alkynyl, nitro, —CN, $OR_b$, —S(O)$_p R_c$, —S(O)$_p NR_a R_a$, —$NR_a$S(O)$_p R_c$, —$NR_a R_a$, —$NR_a$C(=O)$R_b$, —$NR_a$C(=O)$NR_a R_a$, —C(=O)$OR_b$, —C(=O)$R_b$, —OC(=O)$R_b$, —C(=O)$NR_a R_a$, —P(=O)($C_{1-4}$alkyl)$_2$, $C_{3-6}$cycloalkyl substituted with 0-4 $R_e$, aryl substituted with 0-4 $R_e$, heterocyclyl substituted with 0-4 $R_e$, and heteroaryl substituted with 0-4 $R_e$;

$R_6$, at each occurrence, is independently selected from H, $C_{1-6}$ alkyl substituted with 0-5 $R_e$, —C(=O)$R_b$, —C(=O)$NR_a R_a$, —C(=O)$OR_b$, —S(O)$_p R_c$, —S(O)$_p NR_a R_a$, —(CH$_2$)$_r$—$C_{3-6}$cycloalkyl substituted with 0-4 $R_e$, —(CH$_2$)$_r$-aryl substituted with 0-4 $R_e$, —(CH$_2$)$_r$-heterocyclyl substituted with 0-4 $R_e$, and —(CH$_2$)$_r$-heteroaryl substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —(CH$_2$)$_r$—$C_{3-6}$ carbocyclyl substituted with 0-5 $R_e$, and —(CH$_2$)$_r$-heterocyclyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —(CH$_2$)$_r$—$C_{3-6}$ cycloalkyl, —(CH$_2$)$_r$-aryl, F, Cl, Br, CN, NO$_2$, =O, C(=O)OH, —C(=O)OC$_{1-4}$ alkyl, —(CH$_2$)$_r$OH, and —(CH$_2$)$_r$OC$_{1-4}$alkyl;

$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

As defined above and described herein, L is —(CR$_d$R$_d$)$_{0-3}$—, —NR$_a$—, —S(O)$_p$—, or —C(=O)—. In some embodiments, L is absent when L is —(CR$_a$R$_a$)$_0$—. In some embodiments, L is —CH$_2$—. In some embodiments, L is —CH$_2$CH$_2$—. In some embodiments, L is —CH$_2$CH$_2$CH$_2$—. In some embodiments, L is —NR$_a$—, R$_a$ is H or $C_{1-3}$ alkyl. In some embodiments, L is —NH—. In certain embodiments, L is selected from those functional groups depicted in the examples below.

As defined above and described herein, $R_1$ is selected from CH$_3$ and CD$_3$. In some embodiments, $R_1$ is CH$_3$. In some embodiments, $R_1$ is CD$_3$.

As defined above and described herein, $R_2$ is hydrogen, $C_{1-3}$ alkyl substituted with 0-5 $R_e$, or $C_{3-6}$ cycloalkyl substituted with 0-5 $R_e$. In some embodiments, $R_2$ is hydrogen. In some embodiments, $R_2$ is $C_{1-2}$ alkyl substituted with $C_{3-6}$ cycloalkyl. In some embodiments, $R_2$ is $C_{3-6}$ cycloalkyl. In some embodiments, $R_2$ is methyl. In some embodiments, $R_2$ is ethyl. In some embodiments, $R_2$ is cyclopropyl. In some embodiments, $R_2$ is cyclobutyl. In some embodiments, $R_2$ is cyclopentyl. In some embodiments, $R_2$ is cyclohexyl. In some embodiments, $R_2$ is cyclopropylmethyl. In some embodiments, $R_2$ is cyclobutylmethyl. In some embodiments, $R_2$ is cyclopentylmethyl. In some embodiments, $R_2$ is cyclohexylmethyl. In some embodiments, $R_2$ is cyclopropylethyl. In some embodiments, $R_2$ is cyclobutylethyl. In some embodiments, $R_2$ is cyclopentylethyl. In some embodiments, $R_2$ is cyclohexylethyl. In some embodiments, $R_2$ is —CH$_2$-cyclopropyl or —CH$_2$-cyclobutyl. In some embodiments, $R_2$ is —CH$_2$-cyclobutyl optionally substituted with methyl and —OH. In certain embodiments, $R_2$ is selected from those functional groups depicted in the examples below.

As defined above and described herein, $R_3$ is selected from F, Cl, Br, —OR$_b$, and $C_{1-3}$ alkyl substituted with 0-5 $R_e$. In some embodiments, $R_3$ is F, Cl, Br. In some embodiments, $R_3$ is F, In some embodiments, $R^3$ is $C_{1-3}$ alkyl. In some embodiments, $R_3$ is methyl. In some embodiments, $R_3$ is ethyl. In some embodiments, $R_3$ is propyl. In some embodiments, $R_3$ is OR$_b$. In some embodiments, $R_3$ is —OCH$_3$. In some embodiments, $R_3$ is —OCH$_2$CH$_3$. In some embodiments, $R_3$ is —OCH$_2$CH$_2$CH$_3$. In certain embodiments, $R_3$ is —OCH(F)$_2$. In certain embodiments, $R_3$ is selected from those functional groups depicted in the examples below.

As defined above and described herein, each $R_4$ is

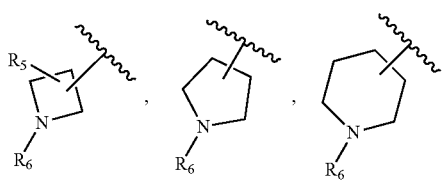

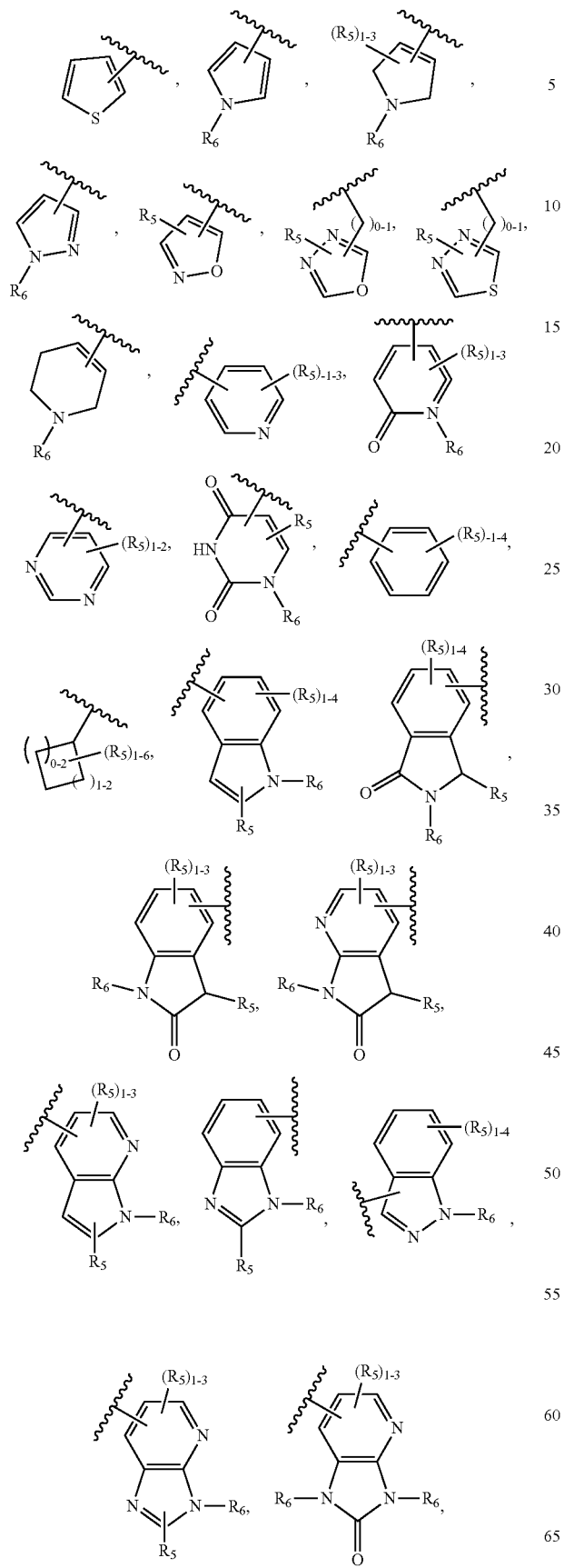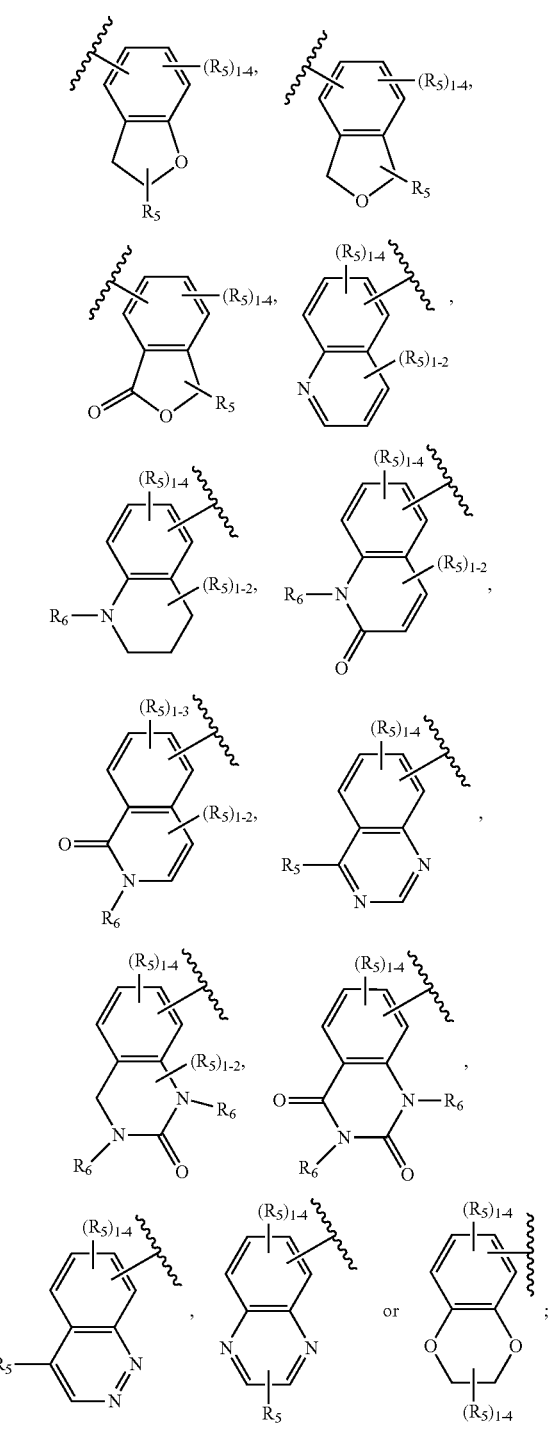
In some embodiments, $R_4$ is
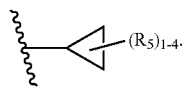

In some embodiments, $R_4$ is
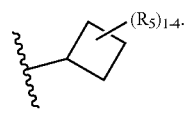
In some embodiments, $R_4$ is
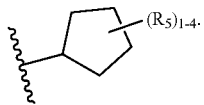
In some embodiments, $R_4$ is
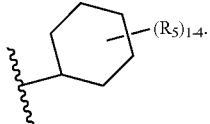
In some embodiments, $R_4$ is
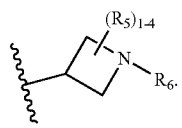
In some embodiments, $R_4$ is
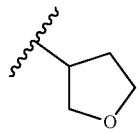
In some embodiments, $R_4$ is
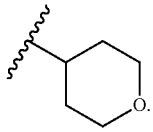
In some embodiments, $R_4$ is
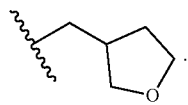
In some embodiments, $R_4$ is
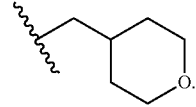
In some embodiments, $R_4$ is
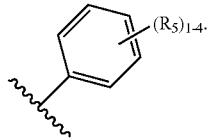
In some embodiments, $R_4$ is
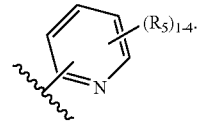
In some embodiments, $R_4$ is
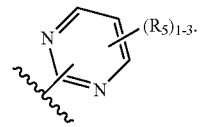
In some embodiments, $R_4$ is
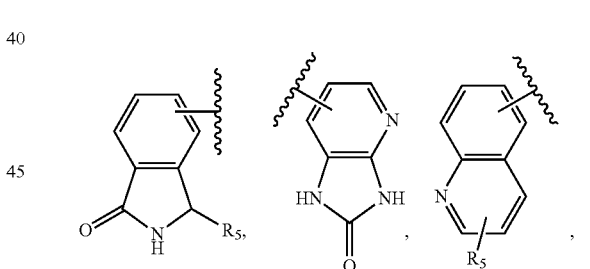
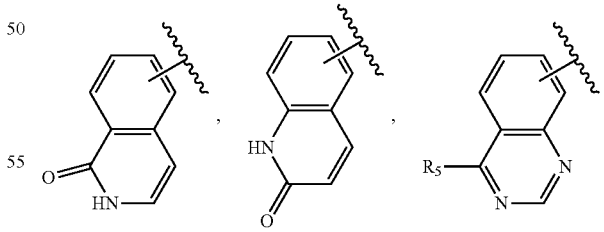
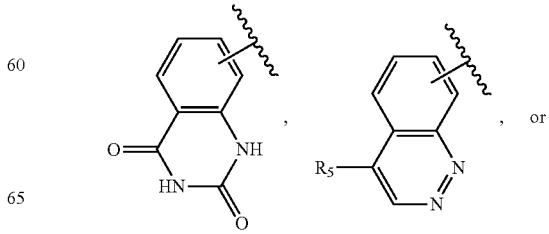

-continued

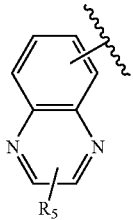

In certain embodiments, $R_4$ is selected from those functional groups depicted in the examples below.

As defined above and described herein, $R_5$ is H, F, Cl, Br, CN, $C_{1-4}$alkyl substituted with 0-5 $R_e$, $C_{2-4}$alkenyl, $C_{2-4}$alkynyl, nitro, —S(O)$_p$R$_c$, —S(O)$_p$NR$_a$R$_a$, —NR$_a$S(O)$_p$ R$_c$, —(CHR$_d$)$_r$OR$_b$, —(CH$_2$)$_r$NR$_a$R$_a$, —NR$_a$C(=O)R$_b$, —NR$_a$C(=O)OR$_b$, —NR$_a$C(=O)NR$_a$R$_a$, —C(=O)R$_b$, —C(=O)OR$_b$, —C(=O)NR$_a$R$_a$, —OC(=O)R$_b$, $C_{3-6}$cycloalkyl substituted with 0-4 $R_e$, aryl substituted with 0-4 $R_e$, and heterocyclyl substituted with 0-4 $R_e$.

In some embodiments, $R_5$ is F. In some embodiments, $R_5$ $C_{1-4}$alkyl. In some embodiments, $R_5$ is —OH or —OC$_{1-3}$alkyl. In some embodiments, $R_5$ is —NHS(O)$_2$C$_{2-4}$alkenyl. In certain embodiments, $R_5$ is selected from those functional groups depicted in the examples below.

As defined above and described herein, $R_6$ is H, $C_{1-3}$alkyl substituted with 0-4 $R_e$, —S(O)$_p$R$_c$, —C(=O)R$_b$, —(CH$_2$)$_r$—C(=O)NR$_a$R$_a$, —C(=O)(CH$_2$)$_r$NR$_a$C(=O)R$_b$, —C(=O)OR$_b$, —S(O)$_p$NR$_a$R$_a$, aryl substituted with 0-4 $R_e$, or heterocyclyl substituted with 0-4 $R_e$.

In some embodiments, $R_6$ is H. In some embodiments, $R_6$ is methyl or isopropyl. In some embodiments, $R_6$ is —(CH$_2$)$_2$ C(=O)NH$_2$. In some embodiments, $R_6$ is —(CH$_2$)$_2$OH. In some embodiments, $R_6$ is C(=O)C$_{1-4}$alkyl. In certain embodiments, $R_6$ is selected from those functional groups depicted in the examples below.

As defined above and described herein, $R_7$ is H, F, Cl, $C_{1-3}$alkyl, —NR$_a$R$_a$, or —NR$_a$C(=O)OR$_b$. In some embodiments, $R_7$ is NH$_2$. In some embodiments $R_7$ is F.

As defined above, Ring A is

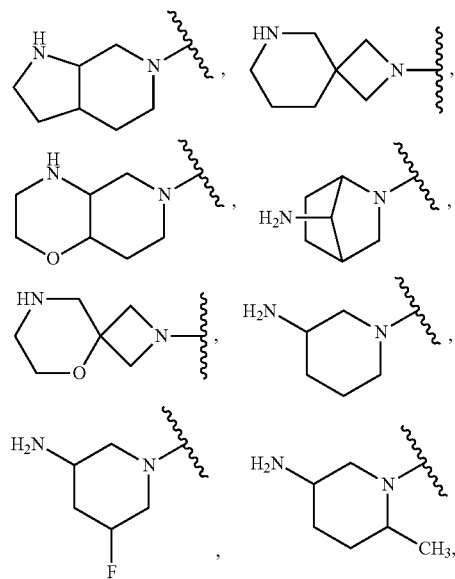

In some embodiments, Ring A is

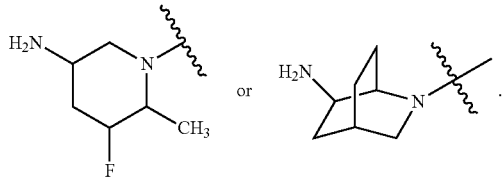

In some embodiments, Ring A is

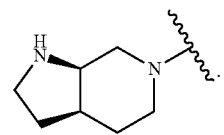 [SMILES: *N1CC[C@H]2CCN[C@H]2C1]

In some embodiments, Ring A is

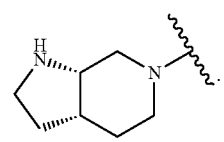 [SMILES: *N1CC[C@@H]2CCN[C@@H]2C1]

In some embodiments, Ring A is

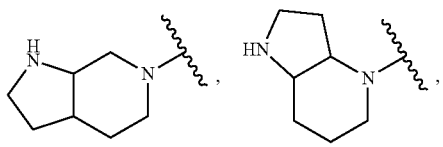

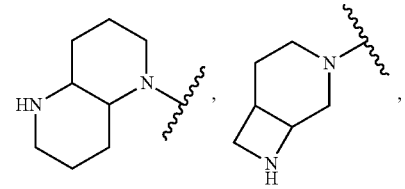

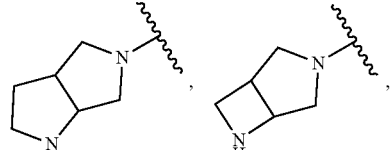

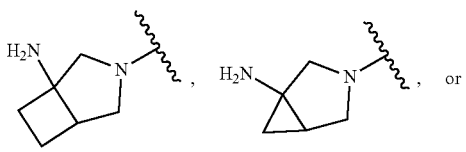

In some embodiments, Ring A is
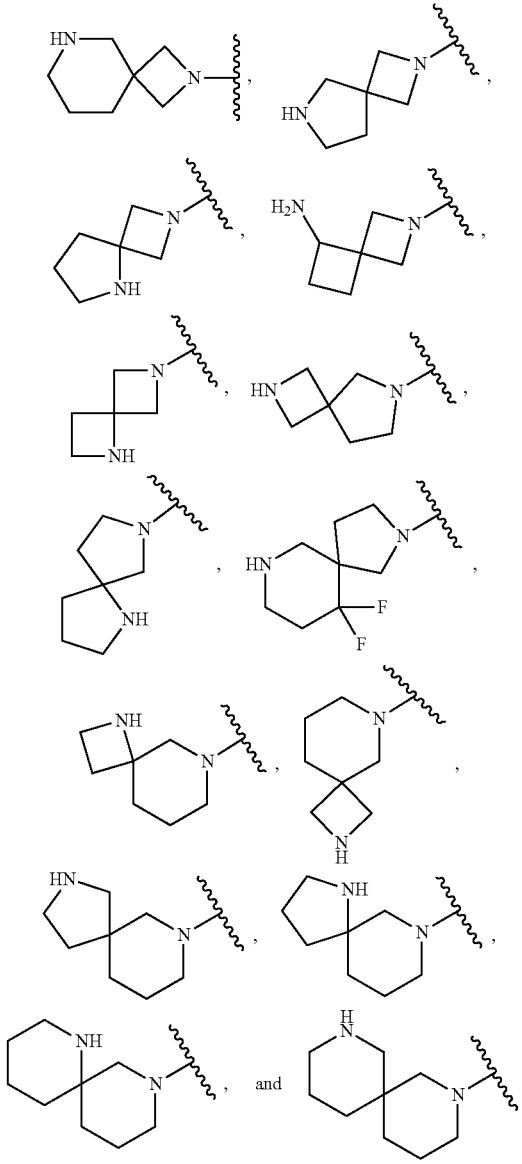
In some embodiments, Ring A is
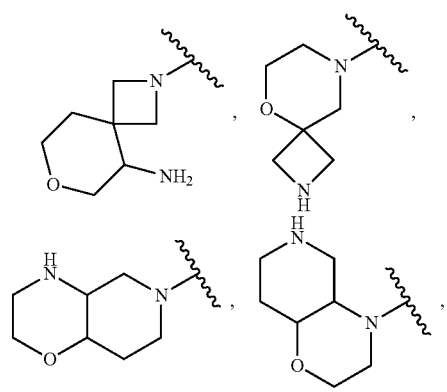
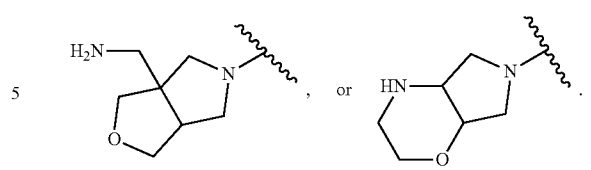
In some embodiments, Ring A is
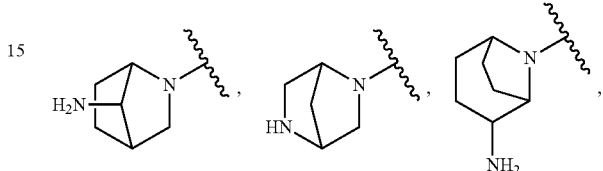
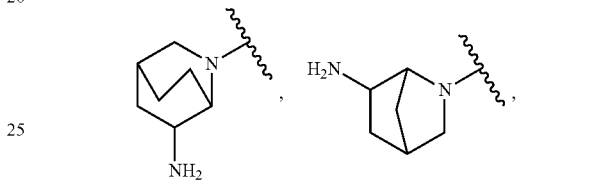
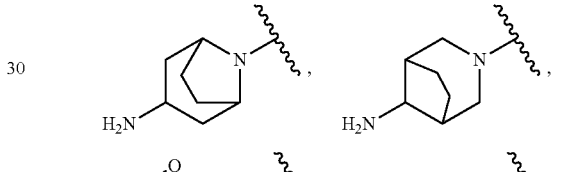
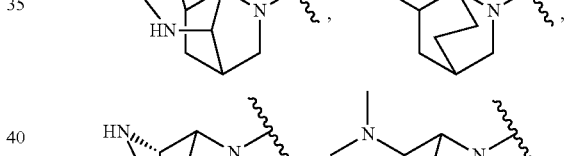
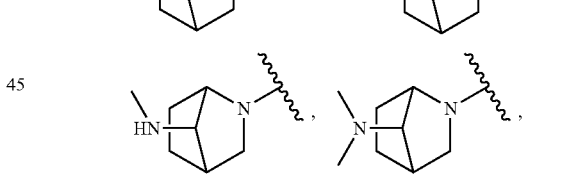
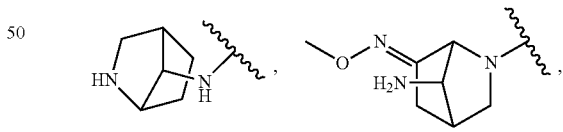
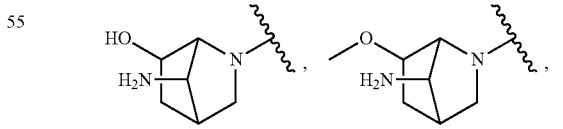
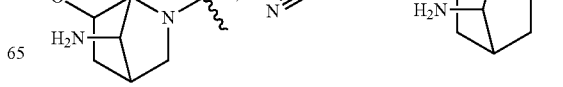

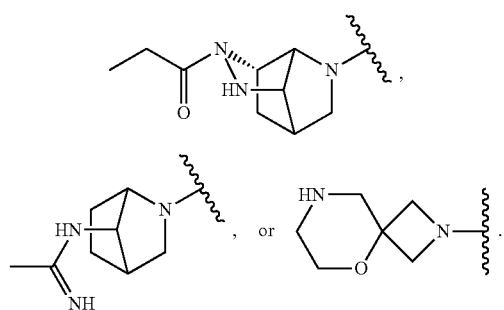
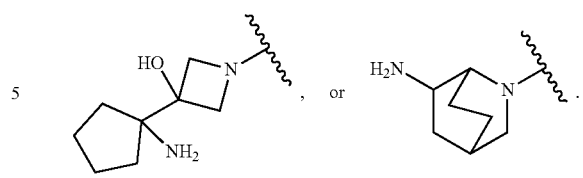
In some embodiments, Ring A is
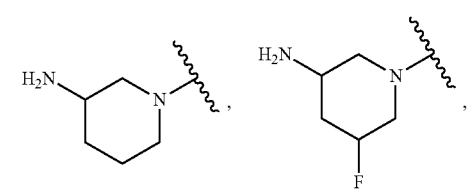
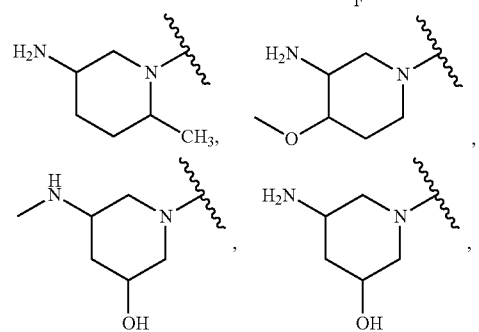
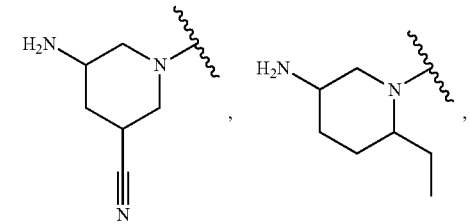
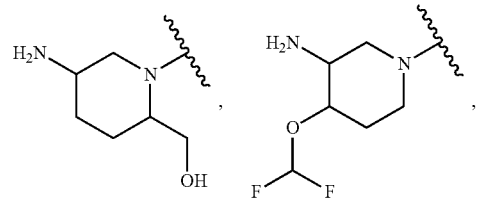
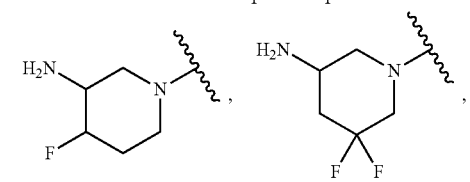
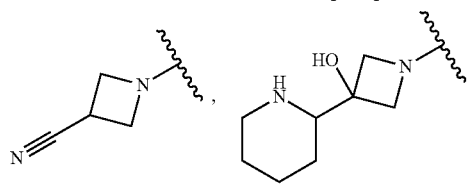
In some embodiments, Ring A is
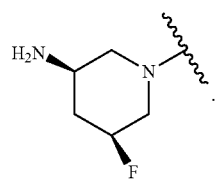 [SMILES: *N1C[C@H](N)C[C@H](F)C1]
In some embodiments, Ring A is
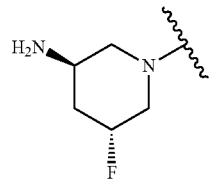
In some embodiments, Ring A is
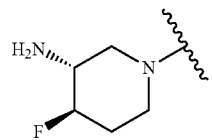
In some embodiments, Ring A is
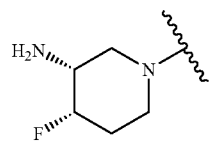
In some embodiments, Ring A is
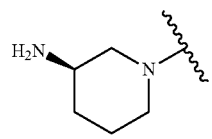

In some embodiments, Ring A is
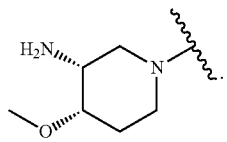 [SMILES: *N1CC[C@H](OC)[C@H](N)C1]
In some embodiments, Ring A is
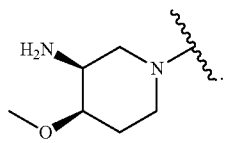 [SMILES: *N1CC[C@@H](OC)[C@@H](N)C1]
In some embodiments, Ring A is
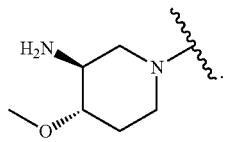 [SMILES: *N1CC[C@H](OC)[C@@H](N)C1]
In some embodiments, Ring A is
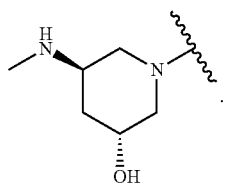 [SMILES: *N1C[C@H](O)C[C@@H](NC)C1]
In some embodiments, Ring A is
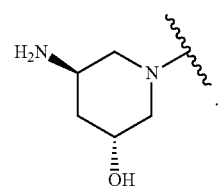
In some embodiments, Ring A is
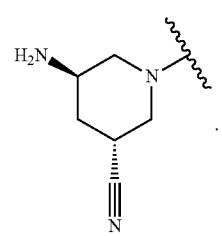
In some embodiments, Ring A is
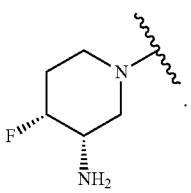
In some embodiments, Ring A is
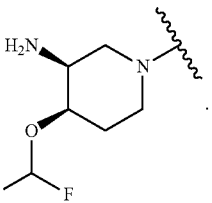
In some embodiments, Ring A is
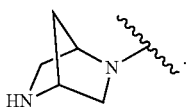
In some embodiments, Ring A is
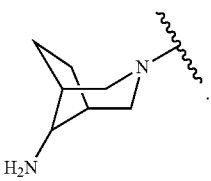
In some embodiments, Ring A is
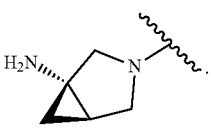
In some embodiments, Ring A is
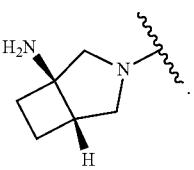 [SMILES: *N1C[C@@H]2CC[C@]2(N)C1]

In some embodiments, Ring A is
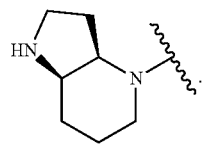 [SMILES: *N1CCC[C@H]2NCC[C@H]21]
In some embodiments, Ring A is
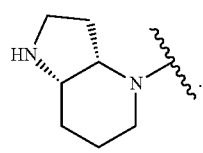 [SMILES: *N1CCC[C@@H]2NCC[C@@H]21]
In some embodiments, Ring A is
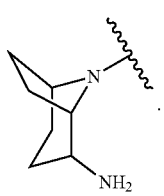 [SMILES: *N1C2CCC(N)C1CC2]
In some embodiments, Ring A is
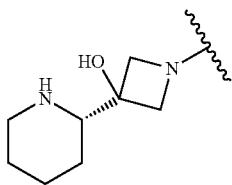
In some embodiments, Ring A is
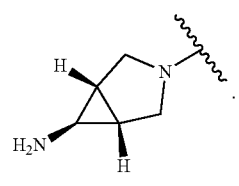 [SMILES: *N1C[C@@H]2[C@@H](N)[C@@H]2C1]
In some embodiments, Ring A is
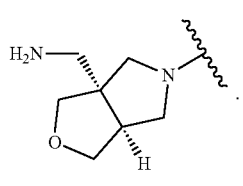
In some embodiments, Ring A is
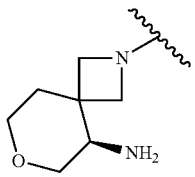
In some embodiments, Ring A is
In some embodiments, Ring A is
In some embodiments, Ring A is
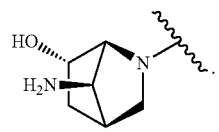 [SMILES: *N1C[C@H]2C[C@H](O)[C@@H]1[C@@H]2N]
In some embodiments, Ring A is
In some embodiments, Ring A is
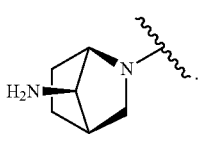

| 41 | 42 |
|---|---|
| In some embodiments, Ring A is 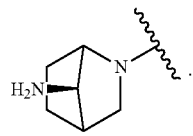 | In some embodiments, Ring A is 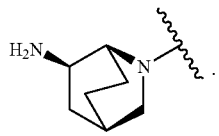 |
| In some embodiments, Ring A is 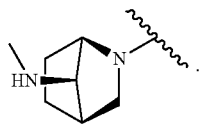 [SMILES: *N1C[C@H]2CC[C@@H]1[C@@H]2NC] | In some embodiments, Ring A is 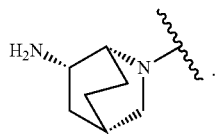 |
| In some embodiments, Ring A is 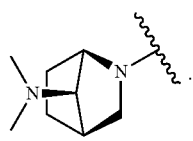 [SMILES: *N1C[C@H]2CC[C@@H]1[C@@H]2N(C)C] | In some embodiments, Ring A is 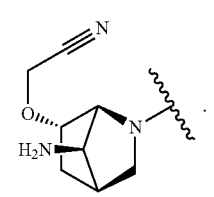 |
| In some embodiments, Ring A is 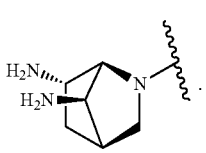 [SMILES: *N1C[C@H]2C[C@H](N)[C@@H]1[C@@H]2N] | In some embodiments, Ring A is 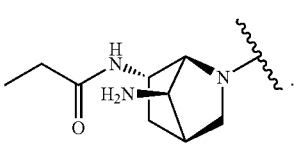 |
| In some embodiments, Ring A is 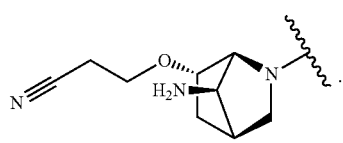 [SMILES: *N1C[C@H]2C[C@H](OCCC#N)[C@@H]1[C@@H]2N] | In some embodiments Ring A is 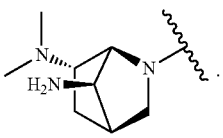 |
| In some embodiments, Ring A is 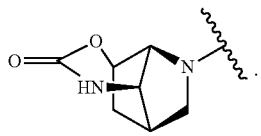 [SMILES: *N1C[C@H]2CC3OC(=O)N[C@H]2[C@@H]31] | In some embodiments, Ring A is 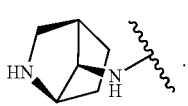 |
| In some embodiments, Ring A is 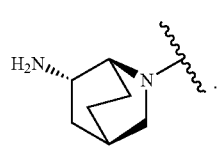 [SMILES: *N1C[C@@H]2CC[C@H]1[C@@H](N)C2] | In some embodiments, Ring A is 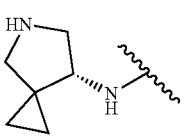 |

In some embodiments, Ring A is
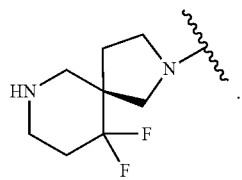
In some embodiments, Ring A is
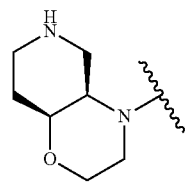
In some embodiments, Ring A is
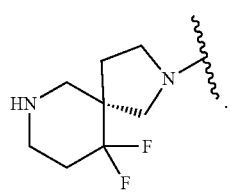 [SMILES: *N1CC[C@@]2(CNCCC2(F)F)C1]
In some embodiments, Ring A is
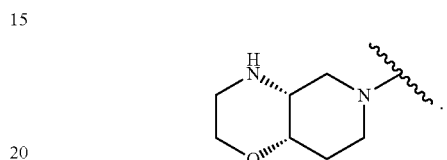
In some embodiments, Ring A is
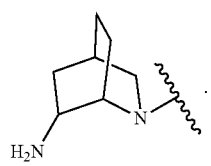
In some embodiments, Ring A is
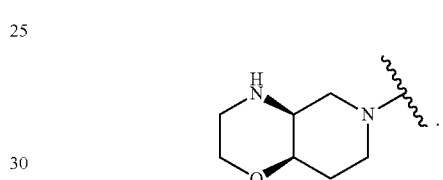
In some embodiments Ring A is
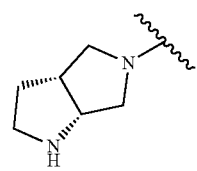
In some embodiments, Ring A is
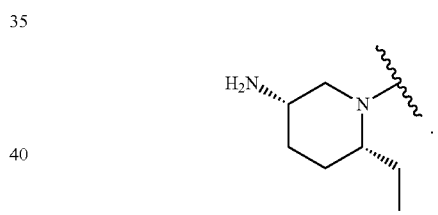
In some embodiments, Ring A is
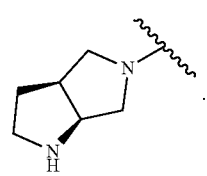 [SMILES: *N1C[C@@H]2CCN[C@@H]2C1]
In some embodiments, Ring A is
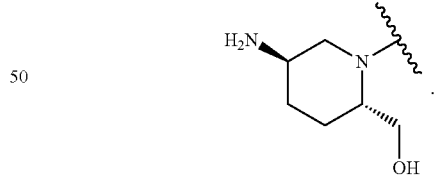
In some embodiments Ring A is
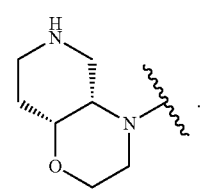 [SMILES: *N1CCO[C@@H]2CCNC[C@@H]21]
In some embodiments, Ring A is
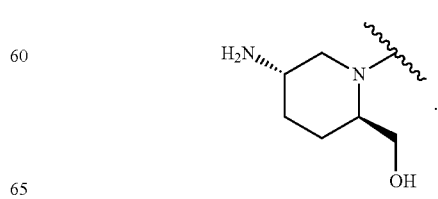

In some embodiments, Ring A is

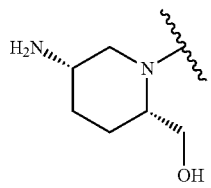

In some embodiments, Ring A is

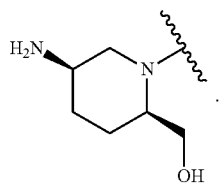 [SMILES: *N1C[C@H](N)CC[C@@H]1CO]

In some embodiments, Ring A is

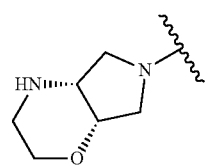

In some embodiments, Ring A is

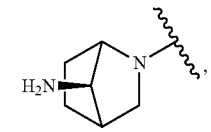

In certain embodiments, Ring A is selected from those functional groups depicted in the examples below.

As defined above and described herein, r is 0-4. In some embodiments, r is 0. In some embodiments, r is 1. In some embodiments, r is 2. In some embodiments, r is 3. In some embodiments, r is 4.

In some embodiments, Ring A is

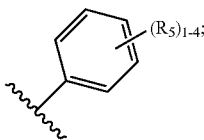

L is absent; $R_2$ is cyclopropylmethyl; $R_3$ is H, F or —OCH$_3$; $R_4$ is

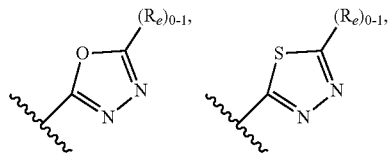

and $R_5$ is H, F, Cl, CN, $C_{1-4}$alkyl, $C_{1-4}$alkyl substituted with OH, NH$_2$, and COOH, SC$_{1-4}$alkyl, S(O)$_2$C$_{1-4}$alkyl, S(O)$_2$NH-cyclopropyl, —(CH$_2$)$_{0-1}$NHS(O)$_2$C$_{1-4}$alkyl, N(R$_d$)S(O)$_2$ C$_{2-4}$alkenyl, —(CH$_2$)$_{0-1}$OH, OC$_{1-4}$alkyl, —(CH$_2$)$_{0-1}$NH$_2$, —(CH$_2$)$_{0-1}$NHC(=O)C$_{1-4}$alkyl, —NR$_d$C(=O)C$_{2-4}$alkenyl, —NHC(=O)C$_{2-4}$alkynyl, —(CH$_2$)$_{0-1}$C(=O)OH, —C(=O)OC$_{1-4}$alkyl, —NHC(=O)OC$_{1-4}$alkyl, —NHC(=O)O(CH$_2$)$_2$OC$_{1-4}$alkyl, —NHC(=O)OCH$_2$-cyclopropyl, —NHC(=O)NH$_2$, C(=O)NHC$_{1-4}$alkyl, CONH(CH$_2$)$_{1-2}$C(=O)OH, —(CH$_2$)$_{0-1}$C(=O)NH$_2$, —(CH$_2$)$_{0-1}$C(=O)NHC$_{1-4}$alkyl, C(=O)NH-pyridine, —C(=O)NH(CH$_2$)$_2$N(C$_{1-4}$alkyl)$_2$, —C(=O)NH(CH$_2$)$_2$OH, —C(=O)NH(CH$_2$)$_2$S(O)$_2$C$_{1-4}$alkyl, and —OC(=O)C$_{1-4}$alkyl,

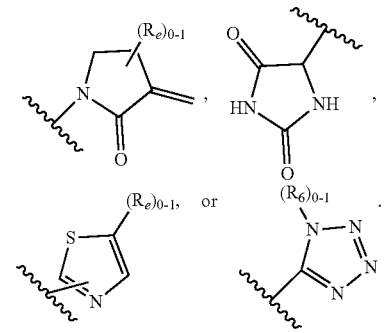

In some embodiments, Ring A is

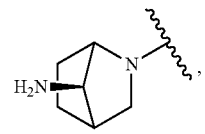

L is —CH$_2$—; $R_2$ is cyclopropylmethyl; $R_3$ is H, F or —OCH$_3$; $R_4$ is

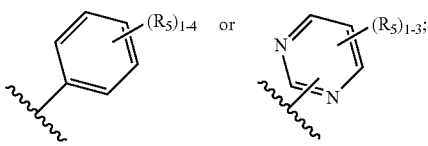

and $R_5$ is H, F, Cl, CN, $C_{1-4}$alkyl, $C_{1-4}$alkyl substituted with OH, NH$_2$, and COOH, SC$_{1-4}$alkyl, S(O)$_2$C$_{1-4}$alkyl, S(O)$_2$NH-cyclopropyl, —(CH$_2$)$_{0-1}$NHS(O)$_2$C$_{1-4}$alkyl, N(R$_d$)S(O)$_2$ C$_{2-4}$alkenyl, —(CH$_2$)$_0$—O$_1$H, OC$_{1-4}$alkyl, —(CH$_2$)$_{0-1}$ NH$_2$, —(CH$_2$)$_{0-1}$NHC(=O)C$_{1-4}$alkyl, —NR$_d$C(=O)C$_{2-4}$alkenyl, —NHC(=O)C$_{2-4}$alkynyl, —(CH$_2$)$_{0-1}$C(=O)OH, —C(=O)OC$_{1-4}$alkyl, —NHC(=O)OC$_{1-4}$alkyl, —NHC(=O)O(CH$_2$)$_2$OC$_{1-4}$alkyl, —NHC(=O)OCH$_2$-cyclopropyl, —NHC(=O)NH$_2$, C(=O)NHC$_{1-4}$alkyl, CONH(CH$_2$)$_{1-2}$C(=O)OH, —(CH$_2$)$_{0-1}$C(=O)NH$_2$, —(CH$_2$)$_{0-1}$C(=O)NHC$_{1-4}$alkyl, C(=O)NH-pyridine, —C(=O)NH(CH$_2$)$_2$N(C$_{1-4}$alkyl)$_2$, —C(=O)NH(CH$_2$)$_{20}$H, —C(=O)NH(CH$_2$)$_2$S(O)$_2$C$_{1-4}$alkyl, and —OC(=O)C$_{1-4}$alkyl,

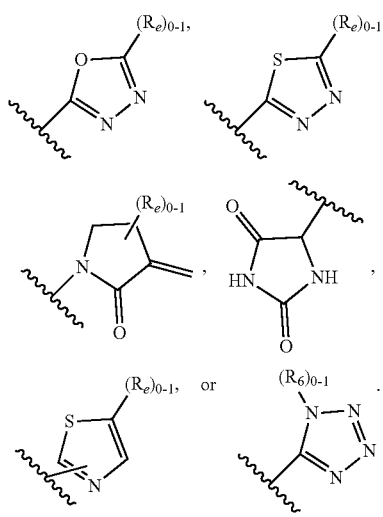

In some embodiments, Ring A is

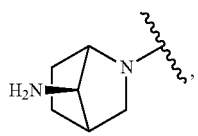

L is absent; R$_2$ is cyclopropylmethyl; R$_3$ is H, F or —OCH$_3$; R$_4$ is

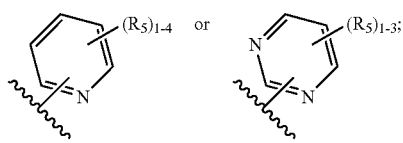

and R$_5$ is H, F, Cl, CN, C$_{1-4}$alkyl, C$_{1-4}$alkyl substituted with OH, NH$_2$, and COOH, SC$_{1-4}$alkyl, S(O)$_2$C$_{1-4}$alkyl, S(O)$_2$NH-cyclopropyl, —(CH$_2$)$_{0-1}$NHS(O)$_2$C$_{1-4}$alkyl, N(R$_d$)S(O)$_2$ C$_{2-4}$alkenyl, —(CH$_2$)$_0$—O$_1$H, OC$_{1-4}$alkyl, —(CH$_2$)$_{0-1}$NH$_2$, —(CH$_2$)$_{0-1}$NHC(=O)C$_{1-4}$alkyl, —NR$_d$C(=O)C$_{2-4}$alkenyl, —NHC(=O)C$_{2-4}$alkynyl, —(CH$_2$)$_{0-1}$C(=O)OH, —C(=O)OC$_{1-4}$alkyl, —NHC(=O)OC$_{1-4}$alkyl, —NHC(=O)O(CH$_2$)$_2$OC$_{1-4}$alkyl, —NHC(=O)OCH$_2$-cyclopropyl, —NHC(=O)NH$_2$, C(=O)NHC$_{1-4}$alkyl, CONH(CH$_2$)$_{1-2}$C(=O)OH, —(CH$_2$)$_{0-1}$C(=O)NH$_2$, —(CH$_2$)$_{0-1}$C(=O)NHC$_{1-4}$alkyl, C(=O)NH-pyridine, —C(=O)NH(CH$_2$)$_2$N(C$_{1-4}$alkyl)$_2$, —C(=O)NH(CH$_2$)$_{20}$H, —C(=O)NH(CH$_2$)$_2$S(O)$_2$C$_{1-4}$alkyl, and —OC(=O)C$_{1-4}$alkyl,

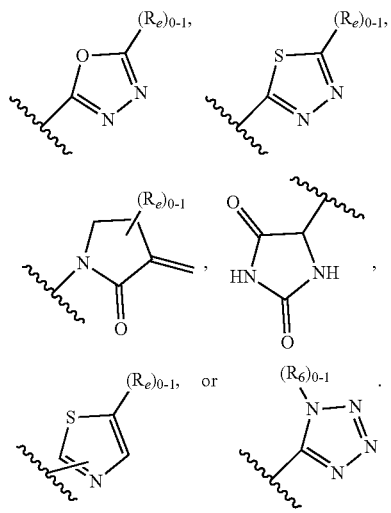

In some embodiments, Ring A is

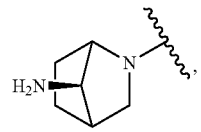

L is —CH$_2$—; R$_2$ is cyclopropylmethyl; R$_3$ is H, F or —OCH$_3$; R$_4$ is

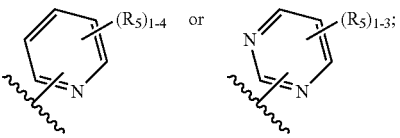

and R$_5$ is H, F, Cl, CN, C$_{1-4}$alkyl, C$_{1-4}$alkyl substituted with OH, NH$_2$, and COOH, SC$_{1-4}$alkyl, S(O)$_2$C$_{1-4}$alkyl, S(O)$_2$NH-cyclopropyl, —(CH$_2$)$_{0-1}$NHS(O)$_2$C$_{1-4}$alkyl, N(R$_d$)S(O)$_2$ C$_{2-4}$alkenyl, —(CH$_2$)$_{0-1}$O$_1$H, OC$_{1-4}$alkyl, —(CH$_2$)$_{0-1}$NH$_2$, —(CH$_2$)$_{0-1}$NHC(=O)C$_{1-4}$alkyl, —NR$_d$C(=O)C$_{2-4}$alkenyl, —NHC(=O)C$_{2-4}$alkynyl, —(CH$_2$)$_{0-1}$C(=O)OH, —C(=O)OC$_{1-4}$alkyl, —NHC(=O)OC$_{1-4}$alkyl, —NHC(=O)O(CH$_2$)$_2$OC$_{1-4}$alkyl, —NHC(=O)OCH$_2$-cyclopropyl, —NHC(=O)NH$_2$, C(=O)NHC$_{1-4}$alkyl, CONH(CH$_2$)$_{1-2}$C(=O)OH, —(CH$_2$)$_{0-1}$C(=O)NH$_2$, —(CH$_2$)$_{0-1}$C(=O)NHC$_{1-4}$alkyl, C(=O)NH-pyridine, —C(=O)NH(CH$_2$)$_2$N(C$_{1-4}$alkyl)$_2$, —C(=O)NH(CH$_2$)$_2$OH, —C(=O)NH(CH$_2$)$_2$S(O)$_2$C$_{1-4}$alkyl, and —OC(=O)C$_{1-4}$alkyl,

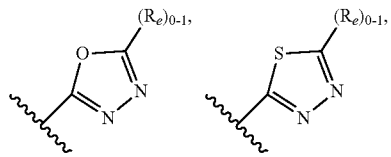

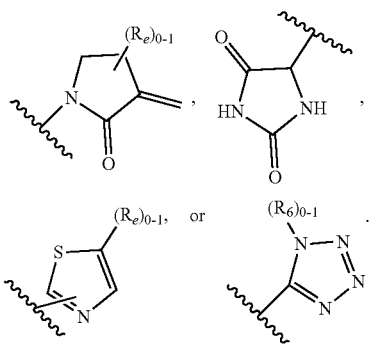

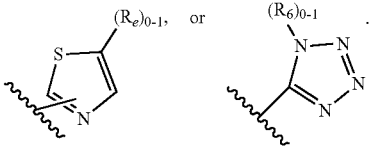

In some embodiments, Ring A is

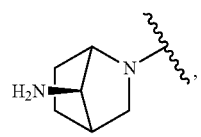

L is absent or —CH$_2$—; R2 is cyclopropylmethyl; R3 is H, F or —OCH3; R4 is

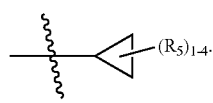

In some embodiments, Ring A is

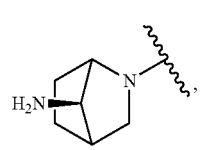

L is absent or —CH$_2$—; R2 is cyclopropylmethyl; R3 is H, F or —OCH3; R4 is

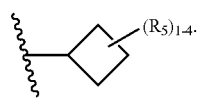

In some embodiments, Ring A is

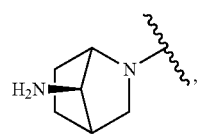

L is absent or —CH$_2$—; R$_2$ is cyclopropylmethyl; R$_3$ is H, F or —OCH3; R$_4$ is

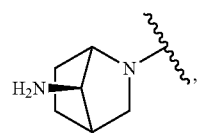

In some embodiments, Ring A is

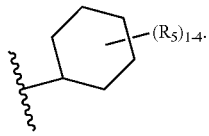

L is absent or —CH$_2$—; R$_2$ is cyclopropylmethyl; R$_3$ is H, F or —OCH$_3$; R$_4$ is

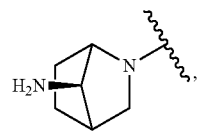

In some embodiments, Ring A is

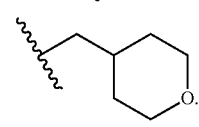

L is absent or —CH$_2$—; R$_2$ is cyclopropylmethyl; R$_3$ is H, F or —OCH$_3$; R$_4$ is

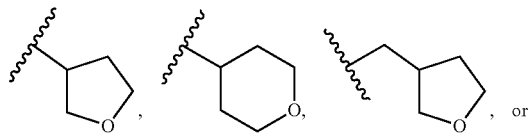

In some embodiments, Ring A is

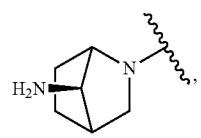

L is absent or —CH$_2$—; R$_2$ is cyclopropylmethyl; R$_3$ is H, F or —OCH$_3$; R$_4$ is

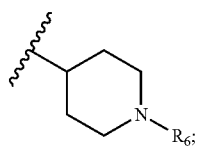

$R_6$ is H, $C_{1-3}$ alkyl and —C(=O)$R_b$.

In some embodiments, Ring A is

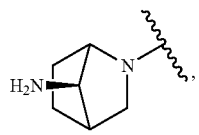

L is absent or —$CH_2$—; $R_2$ is cyclopropylmethyl; $R_3$ is H, F or —$OCH_3$; $R_4$ is

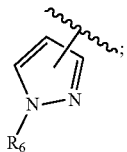

$R_6$ is H, $C_{1-3}$ alkyl and —C(=O)$R_b$.

In some embodiments, the compound of Formula (I) is selected from examples depicted below. In certain embodiments, the present invention provides any compound described above and herein, or a pharmaceutically acceptable salt thereof. In some embodiments, the present invention provides any compound described above and herein in isolated form.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit PAD4, in a biological sample or in a patient. In certain embodiments, the amount of compound in compositions of this invention is such that is effective to measurably inhibit PAD4, in a biological sample or in a patient. In certain embodiments, a composition of this invention is formulated for administration to a patient in need of such composition. In some embodiments, a composition of this invention is formulated for oral administration to a patient.

The term "subject," as used herein, is used interchangeably with the term "patient" and means an animal, preferably a mammal. In some embodiments, a subject or patient is a human. In other embodiments, a subject (or patient) is a veterinary subject (or patient). In some embodiments, a veterinary subject (or patient) is a canine, a feline, or an equine subject.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. Exemplary of such other therapeutic agents include corticosteroids, rolipram, calphostin, cytokine-suppressive antiinflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-□ inhibitors such as tenidap, anti-TNF antibodies or soluble TNF receptor, and rapamycin (sirolimus or Rapamune) or derivatives thereof. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

5. Uses of Compounds and Pharmaceutically Acceptable Compositions

Compounds and compositions described herein are generally useful for the inhibition of PAD4.

The activity of a compound utilized in this invention as an inhibitor of PAD4, may be assayed in vitro, in vivo or in a cell line. In vitro assays include assays that determine the inhibition of PAD4. Detailed conditions for assaying a compound utilized in this invention as an inhibitor of PAD4 are set forth in the Examples below. In some embodiments, a provided compound inhibits PAD4 selectively as compared to PAD2.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of PAD4 and are therefore useful for treating one or more disorders associated with activity of PAD4. Thus, in certain embodiments, the present invention provides a method for treating a PAD4-mediated disorder comprising the step of administering to a patient in need thereof a compound of the present invention, or pharmaceutically acceptable composition thereof.

In one embodiment, a PAD4-mediated disorder is a disease, condition, or disorder mediated by inappropriate PAD4 activity. In some embodiments, a PAD4-mediated disorder is selected from the group consisting of rheumatoid arthritis, vasculitis, systemic lupus erythematosus, ulcerative colitis, cancer, cystic fibrosis, asthma, cutaneous lupus erythematosus, and psoriasis. In a further embodiment, the disorder mediated by inappropriate PAD4 activity is rheumatoid arthritis. In a further embodiment, the disorder mediated by inappropriate PAD4 activity is systemic lupus. In a further embodiment, the disorder mediated by inappropriate PAD4 activity is vasculitis. In a further embodiment, the disorder mediated by inappropriate PAD4 activity is cutaneous lupus erythematosus. In a further embodiment, the disorder mediated by inappropriate PAD4 activity is psoriasis.

In one embodiment there is provided a method of treatment of rheumatoid arthritis, vasculitis, systemic lupus erythematosus, ulcerative colitis, cancer, cystic fibrosis, asthma, cutaneous lupus erythematosus, or psoriasis, which method comprises administering to a human subject in need thereof, a therapeutically effective amount of a provided compound or a pharmaceutically acceptable salt thereof.

In one embodiment there is provided a method of treatment of rheumatoid arthritis, which method comprises administering to a human subject in need thereof, a therapeutically effective amount of a provided compound, or a pharmaceutically acceptable salt thereof. In one embodiment there is provided a method of treatment of systemic lupus, which method comprises administering to a human subject in need thereof, a therapeutically effective amount of a provided compound, or a pharmaceutically acceptable salt thereof. In one embodiment there is provided a method of treatment of vasculitis, which method comprises administering to a human subject in need thereof, a therapeutically effective amount of a provided compound, or a pharmaceutically acceptable salt thereof. In one embodiment there is provided a method of treatment of cutaneous lupus erythematosus, which method comprises administering to a human subject in need thereof, a therapeutically effective amount of a provided compound, or a pharmaceutically acceptable salt thereof. In one embodiment there is provided a method of treatment of psoriasis, which method comprises administering to a human subject in need thereof, a therapeutically effective amount of a provided compound, or a pharmaceutically acceptable salt thereof.

In some embodiments, a PAD4-mediated disorder is selected from the group consisting of acid-induced lung injury, acne (PAPA), acute lymphocytic leukemia, acute, respiratory distress syndrome, Addison's disease, adrenal hyperplasia, adrenocortical insufficiency, ageing, AIDS, alcoholic hepatitis, alcoholic hepatitis, alcoholic liver disease, allergen induced asthma, allergic bronchopulmonary, aspergillosis, allergic conjunctivitis, alopecia, Alzheimer's disease, amyloidosis, amyotropic lateral sclerosis, and weight loss, angina pectoris, angioedema, anhidrotic ecodermal dysplasia-ID, ankylosing spondylitis, anterior segment, inflammation, antiphospholipid syndrome, aphthous stomatitis, appendicitis, arthritis, asthma, atherosclerosis, atopic dermatitis, autoimmune diseases, autoimmune hepatitis, bee sting-induced inflammation, Behcet's disease, Behcet's syndrome, Bells Palsy, berylliosis, Blau syndrome, bone pain, bronchiolitis, burns, bursitis, cancer, cardiac hypertrophy, carpal tunnel syndrome, catabolic disorders, cataracts, cerebral aneurysm, chemical irritant-induced inflammation, chorioretinitis, chronic heart failure, chronic lung disease of prematurity, chronic lymphocytic leukemia, chronic obstructive pulmonary disease, colitis, complex regional pain syndrome, connective tissue disease, corneal ulcer, Crohn's disease, cryopyrin-associated periodic syndromes, cyrptococcosis, cystic fibrosis, deficiency of the interleukin-1-receptor antagonist (DIRA), dermatitis, dermatitis endotoxemia, dermatomyositis, diffuse intrinsic pontine glioma, endometriosis, endotoxemia, epicondylitis, erythroblastopenia, familial amyloidotic polyneuropathy, familial cold urticarial, familial Mediterranean fever, fetal growth retardation, glaucoma, glomerular disease, glomerular nephritis, gout, gouty arthritis, graft-versus-host disease, gut diseases, head injury, headache, hearing loss, heart disease, hemolytic anemia, Henoch-Scholein purpura, hepatitis, hereditary periodic fever syndrome, herpes zoster and simplex, HIV-1, Hodgkin's disease, Huntington's disease, hyaline membrane disease, hyperammonemia, hypercalcemia, hypercholesterolemia, hyperimmunoglobulinemia D with recurrent fever (HIDS), hypoplastic and other anemias, hypoplastic anemia, idiopathic thrombocytopenic purpura, incontinentia pigmenti, infectious mononucleosis, inflammatory bowel disease, inflammatory lung disease, inflammatory neuropathy, inflammatory pain, insect bite-induced inflammation, iritis, irritant-induced inflammation, ischemia/reperfusion, juvenile rheumatoid arthritis, keratitis, kidney disease, kidney injury caused by parasitic infections, kidney injury caused by parasitic infections, kidney transplant rejection prophylaxis, leptospiriosis, leukemia, Loeffler's syndrome, lung injury, lung injury, lupus, lupus, lupus nephritis, lymphoma, meningitis, mesothelioma, mixed connective tissue disease, Muckle-Wells syndrome (urticaria deafness amyloidosis), multiple sclerosis, muscle wasting, muscular dystrophy, myasthenia gravis, myocarditis, mycosis fungoides, mycosis fungoides, myelodysplastic syndrome, myositis, nasal sinusitis, necrotizing enterocolitis, neonatal onset multisystem inflammatory disease (NOMID), nephrotic syndrome, neuritis, neuropathological diseases, non-allergen induced asthma, obesity, ocular allergy, optic neuritis, organ transplant, osteoarthritis, otitis media, Paget's disease, pain, pancreatitis, Parkinson's disease, pemphigus, pericarditis, periodic fever, periodontitis, peritoneal endometriosis, pertussis, pharyngitis and adenitis (PFAPA syndrome), plant irritant-induced inflammation, pneumonia, pneumonitis, pneumosysts infection, poison ivy/urushiol oil-induced inflammation, polyarteritis *nodosa*, polychondritis, polycystic kidney disease, polymyositis, psoriasis, psoriasis, psoriasis, psoriasis, psychosocial stress diseases, pulmonary disease, pulmonary hypertension, pulmonayr fibrosis, pyoderma gangrenosum, pyogenic sterile arthritis, renal disease, retinal disease, rheumatic carditis, rheumatic disease, rheumatoid arthritis, sarcoidosis, seborrhea, sepsis, severe pain, sickle cell, sickle cell anemia, silica-induced disease, Sjogren's syndrome, skin diseases, sleep apnea, solid tumors, spinal cord injury, Stevens-Johnson syndrome, stroke, subarachnoid hemorrhage, sunburn, temporal arteritis, tenosynovitis, thrombocytopenia, thyroiditis, tissue transplant, TNF receptor associated periodic syndrome (TRAPS), toxoplasmosis, transplant, traumatic brain injury, tuberculosis, type 1 diabetes, type 2 diabetes, ulcerative colitis, urticarial, uveitis, Wegener's granulomatosis, interstitial lung disease, psoriatic arthritis, juvenile idiopathic arthritis, Sjögren's syndrome, antineutrophil cytoplasmic antibody (ANCA)-associated vasculitis, antiphospholipid antibody syndrome, sepsis, deep vein thrombosis, fibrosis, Alzheimer's, scleroderma and CREST syndrome.

In one embodiment, the invention provides a provided compound, or a pharmaceutically acceptable salt thereof, for use in therapy. In another embodiment, the invention provides a provided compound, or a pharmaceutically acceptable salt thereof, for use in the treatment of a disorder mediated by inappropriate PAD4 activity. In another embodiment, the invention provides a provided compound, or a pharmaceutically acceptable salt thereof, for use in the treatment of rheumatoid arthritis, vasculitis, systemic lupus erythematosus, ulcerative colitis, cancer, cystic fibrosis, asthma, cutaneous lupus erythematosus, or psoriasis. In another embodiment, the invention provides a provided compound, or a pharmaceutically acceptable salt thereof, for use in the treatment of rheumatoid arthritis. In another embodiment, the invention provides a provided compound, or a pharmaceutically acceptable salt thereof, for use in the treatment of systemic lupus. In another embodiment, the invention provides a provided compound, or a pharmaceutically acceptable salt thereof, for use in the treatment of vasculitis. In another embodiment, the invention provides a provided compound, or a pharmaceutically acceptable salt thereof, for use in the treatment of cutaneous lupus erythematosus. In another embodiment, the invention provides a provided compound, or a pharmaceutically acceptable salt thereof, for use in the treatment of psoriasis. In another embodiment, the invention provides the use of a provided compound, or a pharmaceutically acceptable salt thereof, in the manufacture of a medicament for use in the treatment of a disorder mediated by inappropriate PAD4 activity. In another embodiment, the invention provides the use of a provided compound, or a pharmaceutically acceptable salt thereof, in the manufacture of a medicament for use in the treatment of rheumatoid arthritis, vasculitis, systemic lupus erythematosus, ulcerative colitis, cancer, cystic fibrosis, asthma, cutaneous lupus erythematosus, or psoriasis. In another embodiment, the invention provides the use of a provided compound, or a pharmaceutically acceptable salt thereof, in the manufacture of a medicament for use in the treatment of rheumatoid arthritis. In another embodiment, the invention provides the use of a provided compound, or a pharmaceutically acceptable salt thereof, in the manufacture of a medicament for use in the treatment of systemic lupus. In another embodiment, the invention provides the use of a provided compound, or a pharmaceutically acceptable salt thereof, in the manufacture of a medicament for use in the treatment of vasculitis. In another embodiment, the invention provides the use of a provided compound, or a pharmaceutically acceptable salt thereof, in the manufacture of a medicament for use in the treatment of cutaneous lupus erythematosus. In another embodiment, the invention provides the use of a provided compound, or a pharmaceutically acceptable salt thereof, in the manufacture of a medicament for use in the treatment of psoriasis. In a further embodiment, the invention provides a pharmaceutical composition for the treatment or prophylaxis of a disorder mediated by inappropriate PAD4 activity comprising a provided compound, or a pharmaceutically acceptable salt thereof. In a further embodiment, the invention provides a pharmaceutical composition for the treatment or prophylaxis of rheumatoid arthritis, vasculitis, systemic lupus erythematosus, ulcerative colitis, cancer, cystic fibrosis, asthma, cutaneous lupus erythematosus, or psoriasis, comprising a provided compound, or a pharmaceutically acceptable salt thereof. In a further embodiment, the invention provides a pharmaceutical composition for the treatment or prophylaxis of rheumatoid arthritis comprising a provided compound, or a pharmaceutically acceptable salt thereof. In a further embodiment, the invention provides a pharmaceutical composition for the treatment or prophylaxis of systemic lupus comprising a provided compound, or a pharmaceutically acceptable salt thereof. In a further embodiment, the invention provides a pharmaceutical composition for the treatment or prophylaxis of vasculitis comprising a provided compound, or a pharmaceutically acceptable salt thereof. In a further embodiment, the invention provides a pharmaceutical composition for the treatment or prophylaxis of cutaneous lupus erythematosus comprising a provided compound, or a pharmaceutically acceptable salt thereof. In a further embodiment, the invention provides a pharmaceutical composition for the treatment or prophylaxis of psoriasis comprising a provided compound, or a pharmaceutically acceptable salt thereof.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Certain compounds of the present invention were prepared according to Schemes described below.

For the synthesis of compounds involving photoredox chemistry, see Scheme 1

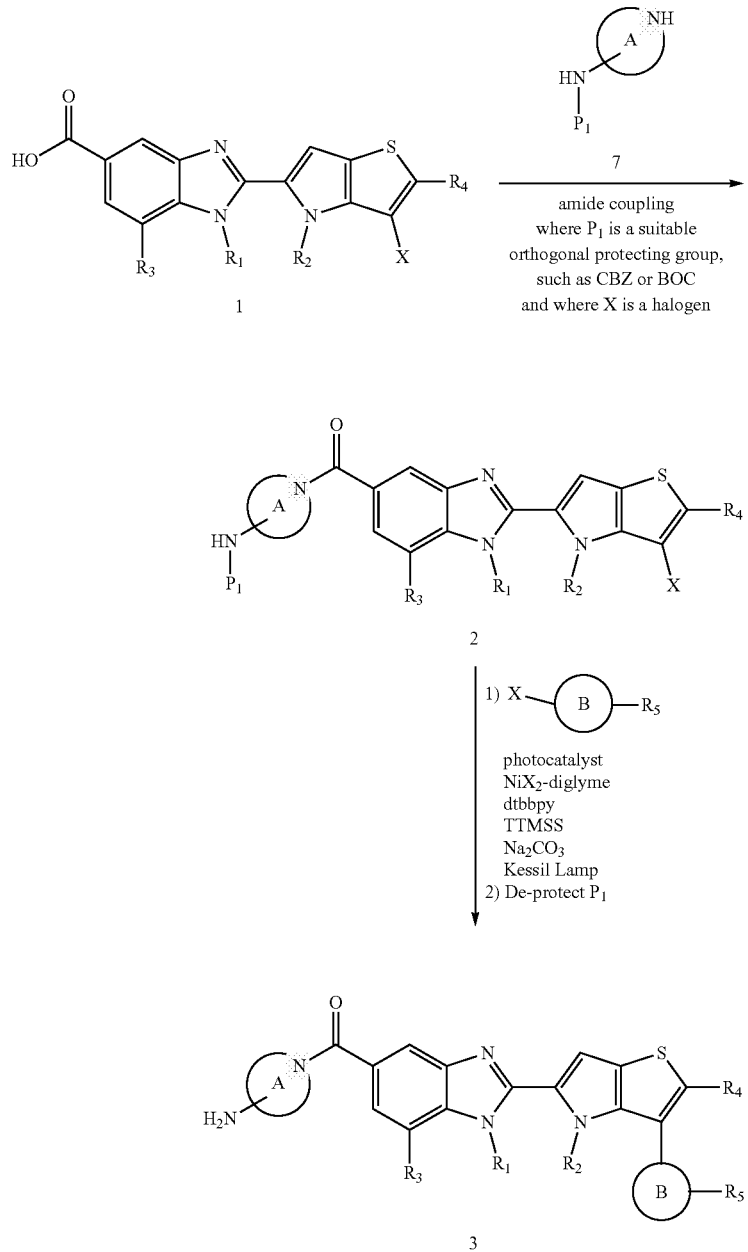

For the synthesis of compounds involving photoredox chemistry of cyclic, bicyclic, or tricyclic protected amines followed by deprotection and subsequent coupling see Scheme 2. Note that the cyclic amine used in the photoredox step can also be in fully elaborated form requiring no subsequent deprotection and coupling steps.

Scheme 2

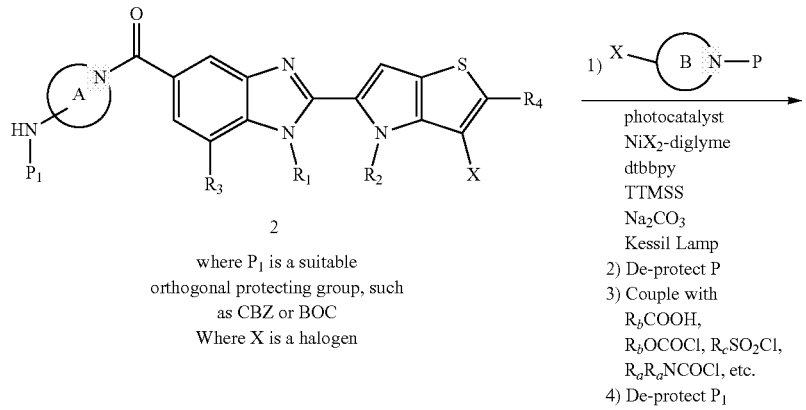

2 where P$_1$ is a suitable orthogonal protecting group, such as CBZ or BOC
Where X is a halogen 1) photocatalyst
NiX$_2$-diglyme
dtbbpy
TTMSS
Na$_2$CO$_3$
Kessil Lamp
2) De-protect P
3) Couple with R$_b$COOH, R$_b$OCOCl, R$_c$SO$_2$Cl, R$_a$R$_a$NCOCl, etc.
4) De-protect P$_1$

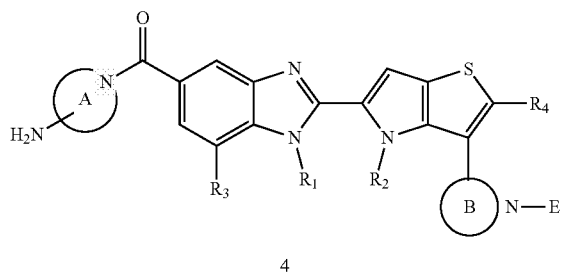

4 where "B" is a saturated ring with or without embedded heteroatoms; E is R$_b$CO—, R$_b$OCO—, R$_c$SO$_2$—, R$_a$R$_a$NCO—, etc.
and R$_1$—R$_6$ are substituents.

For the synthesis of compounds involving photoredox chemistry of cyclic, bicyclic, or tricyclic protected carboxylic acids (for example, esters) followed by deprotection and subsequent coupling see Scheme 3. Note that the cyclic carboxylic acid used in the photoredox step can also be in fully derivatized form requiring no subsequent deprotection and coupling steps.

Scheme 3

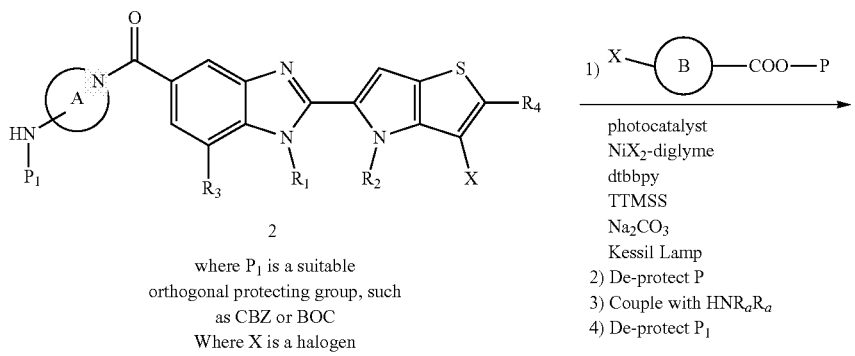

2 where P$_1$ is a suitable orthogonal protecting group, such as CBZ or BOC
Where X is a halogen 1) photocatalyst
NiX$_2$-diglyme
dtbbpy
TTMSS
Na$_2$CO$_3$
Kessil Lamp
2) De-protect P
3) Couple with HNR$_a$R$_a$
4) De-protect P$_1$

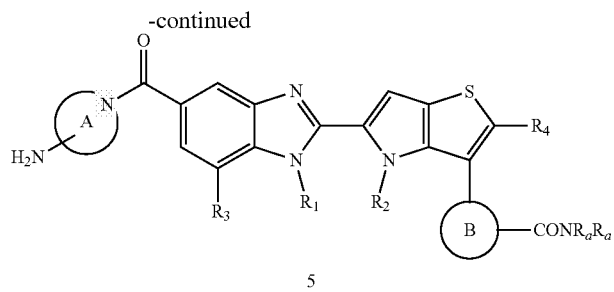

5 where "B" is a saturated ring
with or without
embedded heteroatoms
and $R_1$—$R_6$ are substituents.

For the synthesis of compounds involving the Suzuki, Stille or other aromatic cross-coupling reactions, see Scheme 4.

Scheme 4

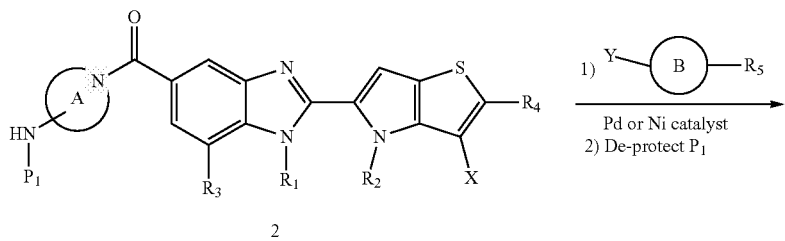

2 where $P_1$ is a suitable
orthogonal protecting group, such
as CBZ or BOC
where X is a halogen and
where Y is a boronic ester or acid,
trifluoroborate salt, zinc halide, magnesium
halide, trialkyltin, or other coupling partner
familiar to one skilled in the art

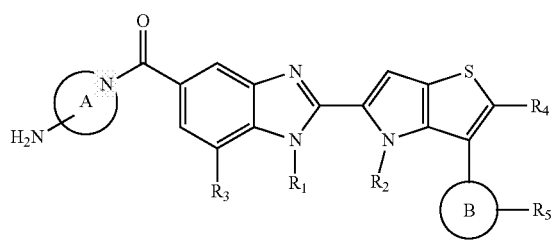

6 where "B" is an aromatic or
heteroaromatic ring or a partially
unsaturated ring containg zero or one
heteroatoms and $R_1$—$R_5$ are substituents.

For the synthesis of Buchwald reaction-type coupled products, see Scheme 5.

Scheme 5

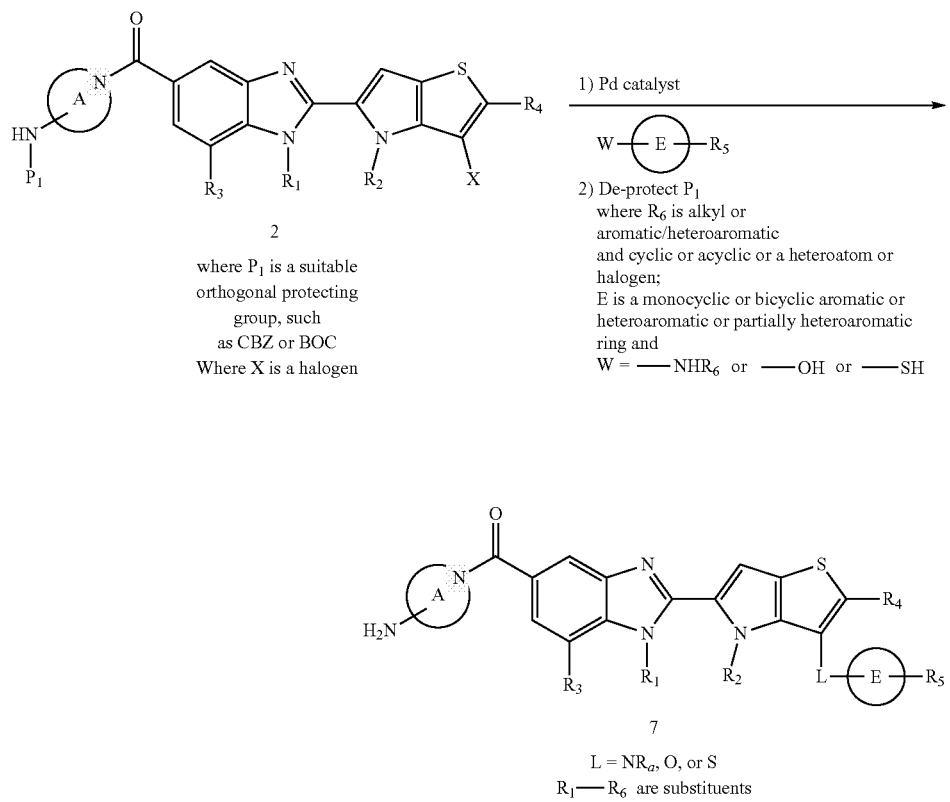

L = NR$_a$, O, or S
R$_1$—R$_6$ are substituents

Description of Analytical LCMS Methods:

Method 1: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Method 2: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Method A: Column: Waters Acquity UPLC BEH C18, 2.1×50 mm, 1.7 μm particles; Mobile Phase A: 5:95 ACN:water with 10 mM NH$_4$OAc; Mobile Phase B: 95:5 ACN:water with 10 mM NH$_4$OAc; Temperature: 50° C.; Gradient: 0-100% B over 3 minutes, then a 0.75 minute hold at 100% B; Flow: 1.11 mL/min; Detection: UV at 220 nm.

Method B: Column: Waters Acquity UPLC BEH C18, 2.1×50 mm, 1.7 μm particles; Mobile Phase A: 5:95 ACN:water with 0.1% TFA; Mobile Phase B: 95:5 ACN:water with 0.1% TFA; Temperature: 50° C.; Gradient: 0-100% B over 3 minutes, then a 0.75 minute hold at 100% B; Flow: 1.11 mL/min; Detection: UV at 220 nm.

Method C: Column: PHENOMENEX® Luna 3 m C$_{18}$ (2.0×30 mm); Mobile Phase A: 10:90 MeOH:water with 0.1% TFA; Mobile Phase B: 90:10 MeOH:water with 0.1% TFA; Gradient: 0-100% B over 2 minutes, then a 1 minute hold at 100% B; Flow: 1 mL/min; Detection: UV at 220 nm.

Method D: Waters Acquity UPLC BEH C18, 2.1×50 mm, 1.7 μm particles; Mobile Phase A: water with 0.05% TFA; Mobile Phase B: ACN with 0.05% TFA; Gradient: 2-98% B over 1 minute, then a 0.5 minute hold at 98% B; Flow: 0.8 mL/min; Detection: UV at 220 or 254 nm.

Example 1

((1R,4R,7R)-7-amino-2-azabicyclo[2.2.1]heptan-2-yl)(2-(3-bromo-4-(cyclopropylmethyl)-4H-thieno[3,2-b]pyrrol-5-yl)-7-methoxy-1-methyl-1H-benzo[d]imidazol-5-yl)methanone

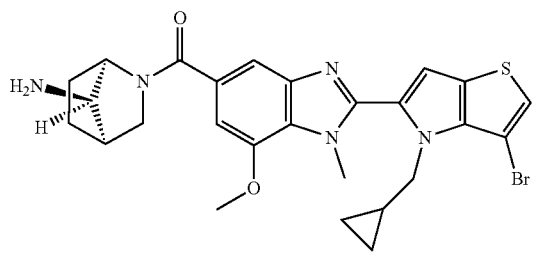 [SMILES: COc1cc(C(=O)N2C[C@H]3CC[C@@H]2[C@@H]3N)cc2nc(-c3cc4scc(Br)c4n3CC3CC3)n(C)c12]

Intermediate 1A: Cyclopropylmethyl 3-bromo-4-(cyclopropylmethyl)-4H-thieno[3,2-b]pyrrole-5-carboxylate

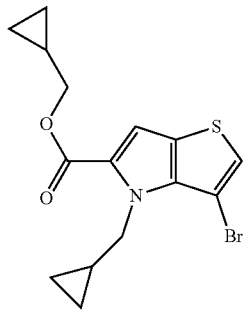 [SMILES: O=C(OCC1CC1)c1cc2scc(Br)c2n1CC1CC1]

In a 40 mL scintillation vial, a stirring mixture of 3-bromo-4H-thieno[3,2-b]pyrrole-5-carboxylic acid (1 g, 4.06 mmol) and potassium carbonate (2.247 g, 16.26 mmol) in DMF (5 mL) was treated with (bromomethyl)cyclopropane (1.577 mL, 16.26 mmol). The vial was sealed, and the reaction was stirred at 70° C. for 3 hours, at which point it was judged to be complete by LCMS. The mixture was diluted with ethyl acetate (75 mL), and the turbid solution was washed once with water, 3× with 10% lithium chloride, and once with brine, then dried over sodium sulfate and concentrated in vacuo. The residue was adsorbed onto Celite and chromatographed via MPLC over a 40 g silica gel column, eluting at 40 mL/min with a 0% to 30% ethyl acetate/hexanes gradient over 14 column volumes. Fractions containing the desired product were pooled and concentrated in vacuo to yield the title compound (1.33 g, 3.75 mmol, 92% yield) as an amber solid. $^1$H NMR (499 MHz, chloroform-d) δ 7.25 (s, 1H), 7.24 (s, 1H), 4.79 (d, J=7.2 Hz, 2H), 4.13 (d, J=7.2 Hz, 2H), 1.46-1.37 (m, 1H), 1.31-1.21 (m, 1H), 0.66-0.60 (m, 2H), 0.52-0.46 (m, 4H), 0.41-0.36 (m, 2H). MS ESI m/z=353.9 (M+H). HPLC retention time 1.25 minutes, Method D.

Intermediate 1B: 3-bromo-4-(cyclopropylmethyl)-4H-thieno[3,2-b]pyrrole-5-carboxylic acid

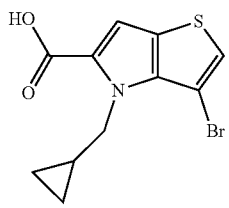 [SMILES: O=C(O)c1cc2scc(Br)c2n1CC1CC1]

A stirring solution of cyclopropylmethyl 3-bromo-4-(cyclopropylmethyl)-4H-thieno[3,2-b]pyrrole-5-carboxylate (1.27 g, 3.58 mmol) in methanol/TIF (3:1) (20 mL) was treated with 1M sodium hydroxide (11.11 mL, 11.11 mmol). The reaction was stirred at 70° C. for 3 hours, at which point it was judged to be complete by LCMS. The organic solvents were evaporated, and the remaining aqueous solution was washed twice with diethyl ether, then treated with 1M HCl (14 mL). The turbid solution was extracted 4× with ethyl acetate, then the combined organic phases were washed once with brine, dried over sodium sulfate, and concentrated in vacuo to yield the title compound (0.99 g, 3.30 mmol, 92% yield) as a colorless solid. $^1$H NMR (500 MHz, DMSO-d$_6$) δ 12.76 (br s, 1H), 7.71 (s, 1H), 7.23 (s, 1H), 4.70 (d, J=7.0 Hz, 2H), 1.37-1.26 (m, 1H), 0.48-0.37 (m, 4H).

Intermediate 1C: methyl 2-(3-bromo-4-(cyclopropylmethyl)-4H-thieno[3,2-b]pyrrol-5-yl)-7-methoxy-1-methyl-1H-benzo[d]imidazole-5-carboxylate

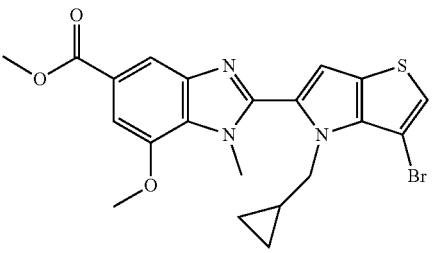 [SMILES: COC(=O)c1cc(OC)c2c(c1)nc(-c1cc3scc(Br)c3n1CC1CC1)n2C]

A stirring solution of methyl 3-amino-5-methoxy-4-(methylamino)benzoate (0.832 g, 3.96 mmol), 3-bromo-4-(cyclopropylmethyl)-4H-thieno[3,2-b]pyrrole-5-carboxylic acid (0.99 g, 3.30 mmol), and Hunig's Base (1.440 mL, 8.25 mmol) in DMF (10 mL) was treated with HATU (1.505 g, 3.96 mmol). The reaction was stirred under a nitrogen atmosphere at room temperature for 60 hours, at which point it was judged to be complete by LCMS based on the disappearance of starting material. The reaction mixture was concentrated in vacuo, and the residue was taken up in ethyl acetate (250 mL) and 10% lithium chloride (100 mL). The turbid mixture was filtered, the layers were separated, and the ethyl acetate phase was washed twice with 10% lithium chloride and once with brine. The organic phase was dried over sodium sulfate and concentrated in vacuo, and the residue was taken up in acetic acid (15 mL). The reaction was heated to 75° C. and stirred for 90 minutes, at which point it was judged to be complete by LCMS. The mixture was concentrated in vacuo, and the residue was taken up in ethyl acetate (100 mL). A magnetic stir bar was added to the flask, and the stirring mixture was carefully treated with half-saturated sodium carbonate until gas evolution ceased. The mixture was stirred for another 10 minutes, during which time a colorless solid precipitated. The solids were collected by filtration, rinsed thoroughly with water and ethyl acetate, followed by a small amount of methanol, and dried under vacuum to yield 700 mg of a pale yellow solid. NMR and LCMS are consistent with the expected product. The combined filtrate and rinsings were transferred to a separatory funnel, and the layers were separated. The organic phase was washed twice with saturated sodium carbonate, and the combined aqueous phases were extracted twice with ethyl acetate (50 mL). The combined organic phases were washed once with brine, dried over sodium sulfate, and concentrated in vacuo to yield 0.85 g of a sticky amber solid. The material was stirred in boiling methanol (15 mL) for 5 minutes, then the solution was allowed to cool to room temperature. The resulting solids were collected by filtration, rinsed 3× with methanol, and dried under vacuum to yield 525 mg of an amber solid. NMR is consistent with the expected product. The two crops of solids were combined to yield the title compound (1.25 g, 2.64 mmol, 80% yield). $^1$H NMR (499 MHz, DMSO-d$_6$) δ 7.94 (d, J=1.3 Hz, 1H), 7.61 (s, 1H), 7.39 (d, J=1.2 Hz, 1H), 7.08 (s, 1H), 4.59 (d, J=7.0 Hz, 2H), 4.09 (s, 3H), 4.02 (s, 3H), 3.89 (s, 3H), 1.13-1.02 (m, 1H), 0.34-0.28 (m, 2H), 0.00--0.05 (m, 2H). MS ESI m/z=476.1 (M+H). HPLC retention time 1.10 minutes, Method D.

Intermediate 1D: 2-(3-bromo-4-(cyclopropylmethyl)-4H-thieno[3,2-b]pyrrol-5-yl)-7-methoxy-1-methyl-1H-benzo[d]imidazole-5-carboxylic acid

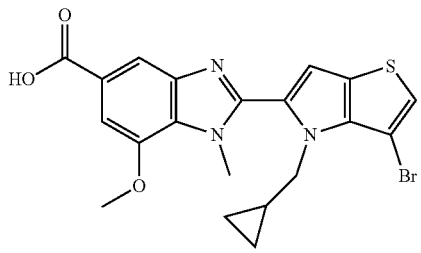 [SMILES: COc1cc(C(=O)O)cc2nc(-c3cc4scc(Br)c4n3CC3CC3)n(C)c12]

A stirring solution of methyl 2-(7-bromo-1-(cyclopropylmethyl)-1H-indol-2-yl)-7-methoxy-1-methyl-1H-benzo[d]imidazole-5-carboxylate (1.25 g, 2.67 mmol) in methanol/THF (2:1) (15 mL) was treated with 1 M sodium hydroxide (8.01 mL, 8.01 mmol). The reaction was stirred at 50° C. for 18 hours, at which point it was judged to be complete by LCMS. The organic solvents were removed on the rotary evaporator, and the remaining heterogeneous aqueous mixture was adjusted to pH 5 with 1M HCl. The mixture was vigorously stirred for 30 minutes, then extracted 4× with ethyl acetate (75 mL). The combined organic phases were washed once with brine, dried over sodium sulfate, and concentrated in vacuo to yield the title compound (1.12 g, 2.433 mmol, 91% yield) as a colorless solid. $^1$H NMR (499 MHz, DMSO-$d_6$) δ 12.85 (br s, 1H), 7.92 (d, J=1.2 Hz, 1H), 7.61 (s, 1H), 7.39 (d, J=1.2 Hz, 1H), 7.07 (s, 1H), 4.59 (d, J=7.0 Hz, 2H), 4.09 (s, 3H), 4.01 (s, 3H), 1.12-1.02 (m, 1H), 0.35-0.27 (m, 2H), 0.00--0.07 (m, 2H). MS ESI m/z=460.1 (M+H). HPLC retention time 0.93 minutes, Method D.

Intermediate 1 E: tert-Butyl ((1R,4R,7R)-2-(2-(3-bromo-4-(cyclopropylmethyl)-4H-thieno[3,2-b]pyrrol-5-yl)-7-methoxy-1-methyl-1H-benzo[d]imidazole-5-carbonyl)-2-azabicyclo[2.2.1]heptan-7-yl)carbamate

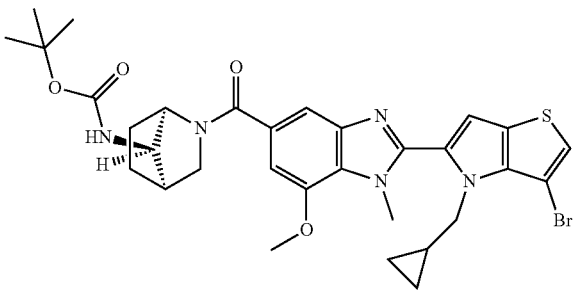 [SMILES: COc1cc(C(=O)N2C[C@H]3CC[C@@H]2[C@@H]3NC(=O)OC(C)(C)C)cc2nc(-c3cc4scc(Br)c4n3CC3CC3)n(C)c12]

A stirring solution of tert-butyl ((1R,4R,7R)-2-azabicyclo[2.2.1]heptan-7-yl)carbamate (0.568 g, 2.68 mmol), 2-(3-bromo-4-(cyclopropylmethyl)-4H-thieno[3,2-b]pyrrol-5-yl)-7-methoxy-1-methyl-1H-benzo[d]imidazole-5-carboxylic acid (1.12 g, 2.433 mmol), and triethylamine (1.017 mL, 7.30 mmol) in dichloromethane (20 mL) was treated with BOP (1.130 g, 2.55 mmol). The reaction was stirred at room temperature for 18 hours, at which point it was judged to be complete by LCMS. The mixture was concentrated in vacuo, and the residue was taken up in ethyl acetate (300 mL). The turbid solution was washed 3× with water, 3× with 1 M sodium hydroxide, and once with brine, then dried over sodium sulfate and concentrated in vacuo. The residue was chromatographed via MPLC over an 80 g silica gel column, eluting at 60 mL/min with a 0% to 10% methanol/dichloromethane gradient over 15 column volumes. Fractions containing the desired product were pooled and concentrated in vacuo to yield the title compound (1.65 g, 2.52 mmol, 104% yield) as a white solid. $^1$H NMR (499 MHz, CHLOROFORM-d) δ 7.48 (d, J=1.1 Hz, 1H), 7.14 (s, 1H), 7.05-6.97 (m, 1H), 6.72-6.67 (m, 1H), 4.69-4.47 (m, 3H), 4.35 (br s, 1H), 4.12 (s, 3H), 4.03 (s, 3H), 3.90-3.71 (m, 2H), 3.31-3.18 (m, 1H), 2.54 (br s, 1H), 2.11-1.81 (m, 3H), 1.72 (br s, 1H), 1.53-1.36 (m, 9H), 1.15-1.05 (m, 1H), 0.40-0.27 (m, 2H), 0.01--0.16 (m, 2H). MS ESI m/z=654.2 (M+H). HPLC retention time 0.97 minutes, Method D.

Example 1

((1R,4R,7R)-7-amino-2-azabicyclo[2.2.1]heptan-2-yl)(2-(3-bromo-4-(cyclopropylmethyl)-4H-thieno[3,2-b]pyrrol-5-yl)-7-methoxy-1-methyl-1H-benzo[d]imidazol-5-yl)methanone A stirring solution of tert-butyl ((1R,4R,7R)-2-(2-(3-bromo-4-(cyclopropylmethyl)-4H-thieno[3,2-b]pyrrol-5-yl)-7-methoxy-1-methyl-1H-benzo[d]imidazole-5-carbonyl)-2-azabicyclo[2.2.1]heptan-7-yl)carbamate (20 mg, 0.031 mmol) in dichloromethane (1 mL) was treated with 4M HCl in dioxane (1 mL, 4.00 mmol). The reaction was stirred at room temperature for one hour, at which point it was judged to be complete by LCMS. The mixture was concentrated in vacuo. The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 31% B, 31-71% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation to yield the title compound, (17.1 mg, 0.031 mmol, 101% yield). $^1$H NMR (500 MHz, DMSO-$d_6$) δ 7.58 (d, J=2.3 Hz, 1H), 7.52-7.36 (m, 1H), 7.04 (d, J=1.7 Hz, 1H), 7.02-6.94 (m, 1H), 4.61 (br d, J=5.1 Hz, 2H), 4.11 (s, 3H), 4.04 (s, 3H), 3.77-3.59 (m, 3H), 3.20-3.06 (m, 1H), 2.35-2.20 (m, 1H), 2.13-1.70 (m, 4H), 1.56-1.40 (m, 1H), 1.09 (br d, J=3.2 Hz, 1H), 0.37 (br d, J=7.9 Hz, 2H), 0.02 (br s, 2H). MS ESI m/z=554.0.2 (M+H). HPLC retention time 1.97 minutes, Method 1.

Example 2

(( 1R,4R,7R)-7-amino-2-azabicyclo[2.2.1]heptan-2-yl)(2-(4-(cyclopropylmethyl)-3-(oxetan-3-yl)-4H-thieno[3,2-b]pyrrol-5-yl)-7-methoxy-1-methyl-1H-benzo[d]imidazol-5-yl)methanone

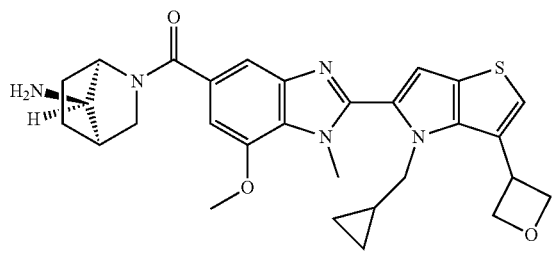 [SMILES: COc1cc(C(=O)N2C[C@H]3CC[C@@H]2[C@@H]3N)cc2nc(-c3cc4scc(C5COC5)c4n3CC3CC3)n(C)c12]

In a 2-dram vial, a stirring mixture of 3-iodooxetane (28.1 mg, 0.153 mmol), tert-butyl ((1R,4R,7R)-2-(2-(3-bromo-4-(cyclopropylmethyl)-4H-thieno[3,2-b]pyrrol-5-yl)-7-methoxy-1-methyl-1H-benzo[d]imidazole-5-carbonyl)-2-azabicyclo[2.2.1]heptan-7-yl)carbamate (50 mg, 0.076 mmol), tris(trimethylsilyl)silane (0.035 mL, 0.115 mmol), Ir(dF(CF3)ppy)$_2$(dtbbpy)PF6 (2.57 mg, 2.291 µmol), and sodium carbonate (32.4 mg, 0.306 mmol) in 1,4-Dioxane (2 mL) was degassed with bubbling nitrogen for 10 minutes. In a separate vial, a stirring mixture of nickel(II) chloride ethylene glycol dimethyl ether complex (2.52 mg, 0.011 mmol), and 4,4'-di-tert-butyl-2,2'-bipyridine (3.49 mg, 0.013 mmol) in 1,4-dioxane (1 mL) was degassed with nitrogen for 20 minutes. The nickel complex was transferred to the containing the other mixture, the vial was sealed, and the reaction was stirred at room temperature under a blue Kessil lamp for 18 hours, at which point it was judged to be complete by LCMS. The mixture was diluted with dichloromethane (2 mL) and filtered, and the filtrate was concentrated in vacuo. The residue was taken up in dichloromethane (2 mL), and the solution was treated with TFA (200 µl, 2.60 mmol). The reaction was stirred at room temperature for 2 hours, at which point it was judged to be complete by LCMS. The mixture was concentrated in vacuo, and the residue was concentrated 3× from dichloromethane to remove residual TFA. The crude material was purified via preparative LC/MS with the following conditions: Column: XBridge C18, 200 mm×19 mm, 5-µm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 16% B, 16-56% B over 30 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation to yield the title compound, (14.9 mg, 0.028 mmol, 36.5% yield). $^1$H NMR (500 MHz, DMSO-d$_6$) δ 7.24 (s, 1H), 7.19-7.06 (m, 1H), 6.75-6.64 (m, 2H), 4.80-4.73 (m, 2H), 4.59 (br t, J=6.0 Hz, 2H), 4.51-4.41 (m, 1H), 4.04 (br s, 2H), 3.84 (s, 3H), 3.75 (s, 3H), 3.57-3.26 (m, 3H), 3.14-2.92 (m, 1H), 2.87-2.74 (m, 1H), 2.05-1.91 (m, 1H), 1.82-1.62 (m, 2H), 1.59-1.43 (m, 1H), 1.27-1.03 (m, 1H), 0.64-0.53 (m, 1H), 0.01 (br d, J=7.6 Hz, 2H), −0.47−−0.62 (m, 2H). MS ESI m/z=532.2 (M+H). HPLC retention time 1.42 minutes, Method 1.

The following compounds in Table 1 can be made by the procedures described in Example 2, substituting the appropriate alkyl halide for 3-bromo-1-propanol. For examples where the substituent at the indole 7-position contains a basic amine, the appropriate Boc-protected aminoalkyl halide was used, and the Boc-group was cleaved during the final deprotection step.

TABLE 1

| Ex # | Structure | Name | M + H (obsion) | LC/MS Method | LC/MS Rt (min) |
|---|---|---|---|---|---|
| 3 | 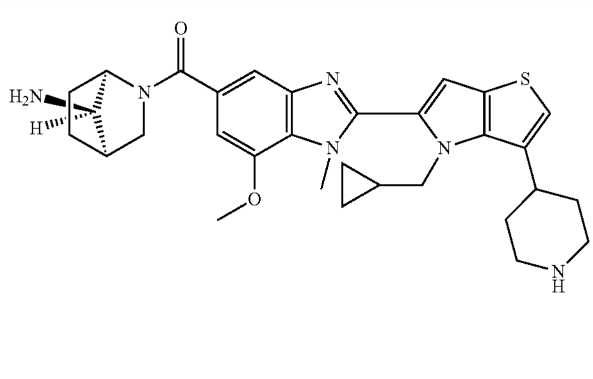 [SMILES: COc1cc(C(=O)N2C[C@H]3CC[C@@H]2[C@@H]3N)cc2nc(-c3cc4scc(C5CCNCC5)c4n3CC3CC3)n(C)c12] | ((1R,4R,7R)-7-amino-2-azabicyclo[2.2.1]heptan-2-yl)(2-(4-(cyclopropylmethyl)-3-(piperidin-4-yl)-4H-thieno[3,2-b]pyrrol-5-yl)-7-methoxy-1-methyl-1H-benzo[d]imidazol-5-yl)methanone | 559.4 | 2 | 0.96 |

TABLE 1-continued

| Ex # | Structure | Name | M + H (obsion) | LC/MS Method | LC/MS Rt (min) |
|---|---|---|---|---|---|
| 4 | 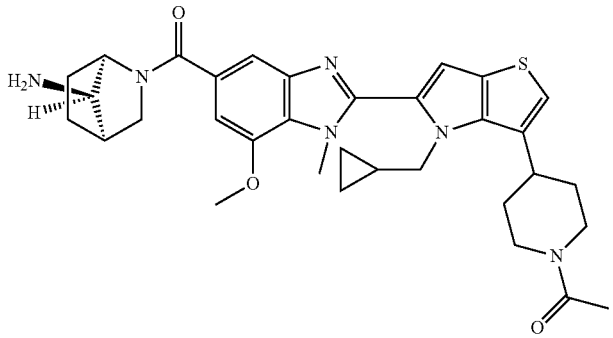 [SMILES: COc1cc(C(=O)N2C[C@H]3CC[C@@H]2[C@@H]3N)cc2nc(-c3cc4scc(C5CCN(C(C)=O)CC5)c4n3CC3CC3)n(C)c12] | 1-(4-(5-(5-((1R,4R,7R)-7-amino-2-azabicyclo[2.2.1]heptane-2-carbonyl)-7-methoxy-1-methyl-1H-benzo[d]imidazol-2-yl)-4-(cyclopropylmethyl)-4H-thieno[3,2-b]pyrrol-3-yl)piperidin-1-yl)ethan-1-one | 601.4 | 1 | 1.48 |
| 5 | 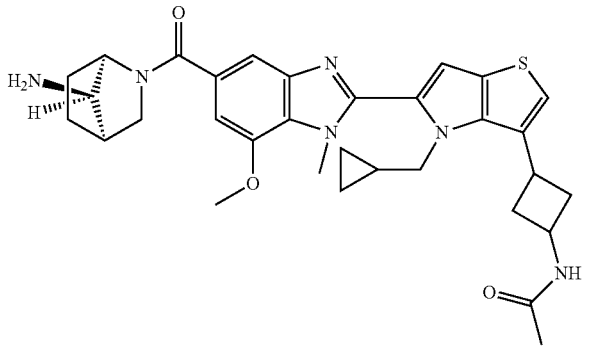 [SMILES: COc1cc(C(=O)N2C[C@H]3CC[C@@H]2[C@@H]3N)cc2nc(-c3cc4scc(C5CC(NC(C)=O)C5)c4n3CC3CC3)n(C)c12] | N-(3-(5-(5-((1R,4R,7R)-7-amino-2-azabicyclo[2.2.1]heptane-2-carbonyl)-7-methoxy-1-methyl-1H-benzo[d]imidazol-2-yl)-4-(cyclopropylmethyl)-4H-thieno[3,2-b]pyrrol-3-yl)cyclobutyl)acetamide | 587.4 | 2 | 1.16 |
| 6 | 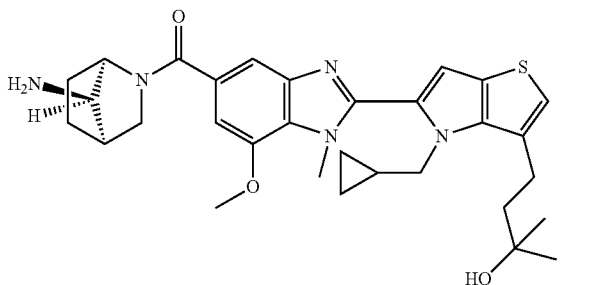 [SMILES: COc1cc(C(=O)N2C[C@H]3CC[C@@H]2[C@@H]3N)cc2nc(-c3cc4scc(CCC(C)(C)O)c4n3CC3CC3)n(C)c12] | ((1R,4R,7R)-7-amino-2-azabicyclo[2.2.1]heptan-2-yl)(2-(4-(cyclopropylmethyl)-3-(3-hydroxy-3-methylbutyl)-4H-thieno[3,2-b]pyrrol-5-yl)-7-methoxy-1-methyl-1H-benzo[d]imidazol-5-yl)methanone | 562.4 | 2 | 1.32 |
| 7 | 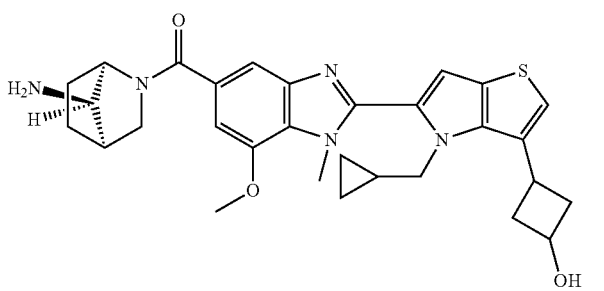 [SMILES: COc1cc(C(=O)N2C[C@H]3CC[C@@H]2[C@@H]3N)cc2nc(-c3cc4scc(C5CC(O)C5)c4n3CC3CC3)n(C)c12] | cis/trans-((1R,4R,7R)-7-amino-2-azabicyclo[2.2.1]heptan-2-yl)(2-(4-(cyclopropylmethyl)-3-(3-hydroxycyclobutyl)-4H-thieno[3,2-b]pyrrol-5-yl)-7-methoxy-1-methyl-1H-benzo[d]imidazol-5-yl)methanone | 546.0 | 2 | 1.27/1.30 |
| 8 | 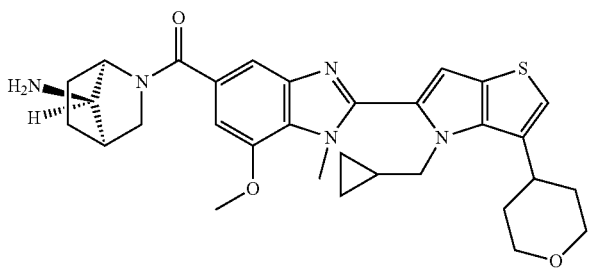 [SMILES: COc1cc(C(=O)N2C[C@H]3CC[C@@H]2[C@@H]3N)cc2nc(-c3cc4scc(C5CCOCC5)c4n3CC3CC3)n(C)c12] | ((1R,4R,7R)-7-amino-2-azabicyclo[2.2.1]heptan-2-yl)(2-(4-(cyclopropylmethyl)-3-(tetrahydro-2H-pyran-4-yl)-4H-thieno[3,2-b]pyrrol-5-yl)-7-methoxy-1-methyl-1H-benzo[d]imidazol-5-yl)methanone | 560.4 | 2 | 1.33 |

TABLE 1-continued

| Ex # | Structure | Name | M + H (obsion) | LC/MS Method | LC/MS Rt (min) |
|---|---|---|---|---|---|
| 9 | 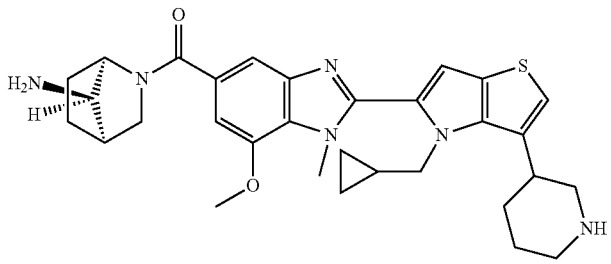 [SMILES: COc1cc(C(=O)N2C[C@H]3CC[C@@H]2[C@@H]3N)cc2nc(-c3cc4scc(C5CCCNC5)c4n3CC3CC3)n(C)c12] | (((1R,4R,7R)-7-amino-2-azabicyclo[2.2.1]heptan-2-yl)(2-(4-(cyclopropylmethyl)-3-(piperidin-3-yl)-4H-thieno[3,2-b]pyrrol-5-yl)-7-methoxy-1-methyl-1H-benzo[d]imidazol-5-yl)methanone, ISOMER 1 | 559.4 | 1 | 1.18 |
| 10 | 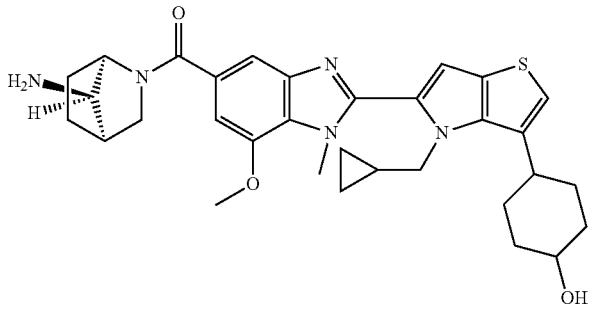 [SMILES: COc1cc(C(=O)N2C[C@H]3CC[C@@H]2[C@@H]3N)cc2nc(-c3cc4scc(C5CCC(O)CC5)c4n3CC3CC3)n(C)c12] | cis/trans-((1R,4R,7R)-7-amino-2-azabicyclo[2.2.1]heptan-2-yl)(2-(4-(cyclopropylmethyl)-3-(4-hydroxycyclohexyl)-4H-thieno[3,2-b]pyrrol-5-yl)-7-methoxy-1-methyl-1H-benzo[d]imidazol-5-yl)methanone | 574.5 | 1 | 1.48/1.51 |
| 11 | 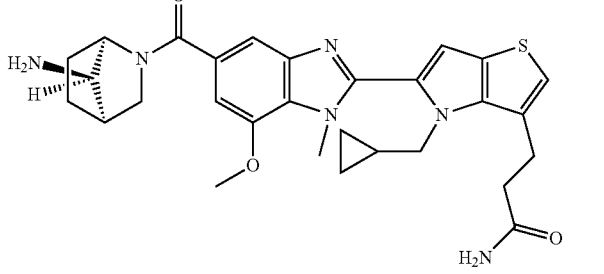 | 3-(5-(5-((1R,4R,7R)-7-amino-2-azabicyclo[2.2.1]heptane-2-carbonyl)-7-methoxy-1-methyl-1H-benzo[d]imidazol-2-yl)-4-(cyclopropylmethyl)-4H-thieno[3,2-b]pyrrol-3-yl)propanamide | 547.5 | 1 | 1.28 |
| 12 | 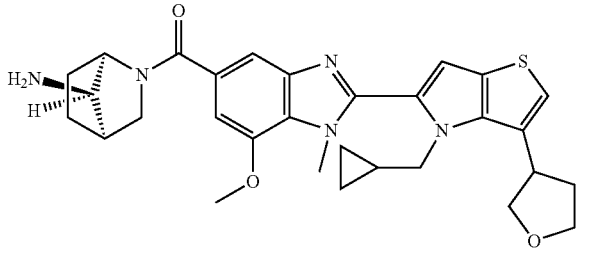 [SMILES: COc1cc(C(=O)N2C[C@H]3CC[C@@H]2[C@@H]3N)cc2nc(-c3cc4scc(C5CCOC5)c4n3CC3CC3)n(C)c12] | ((1R,4R,7R)-7-amino-2-azabicyclo[2.2.1]heptan-2-yl)(2-(4-(cyclopropylmethyl)-3-(tetrahydrofuran-3-yl)-4H-thieno[3,2-b]pyrrol-5-yl)-7-methoxy-1-methyl-1H-benzo[d]imidazol-5-yl)methanone | 545.9 | 1 | 1.67 |
| 13 | 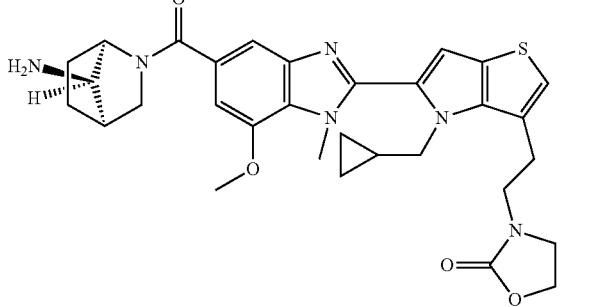 | 3-(2-(5-(5-((1R,4R,7R)-7-amino-2-azabicyclo[2.2.1]heptane-2-carbonyl)-7-methoxy-1-methyl-1H-benzo[d]imidazol-2-yl)-4-(cyclopropylmethyl)-4H-thieno[3,2-b]pyrrol-3-yl)ethyl)oxazolidin-2-one | 589.1 | 1 | 1.55 |

TABLE 1-continued

| Ex # | Structure | Name | M + H (obsrvn) | LC/MS Method | LC/MS Rt (min) |
|---|---|---|---|---|---|
| 14 | 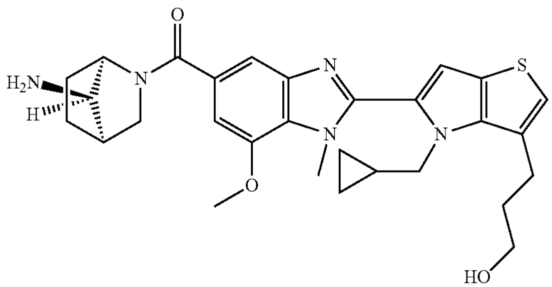 [SMILES: COc1cc(C(=O)N2C[C@H]3CC[C@@H]2[C@@H]3N)cc2nc(-c3cc4scc(CCCO)c4n3CC3CC3)n(C)c12] | ((1R,4R,7R)-7-amino-2-azabicyclo[2.2.1]heptan-2-yl)(2-(4-(cyclopropylmethyl)-3-(3-hydroxypropyl)-4H-thieno[3,2-b]pyrrol-5-yl)-7-methoxy-1-methyl-1H-benzo[d]imidazol-5-yl)methanone | 534.4 | 1 | 1.51 |
| 15 | 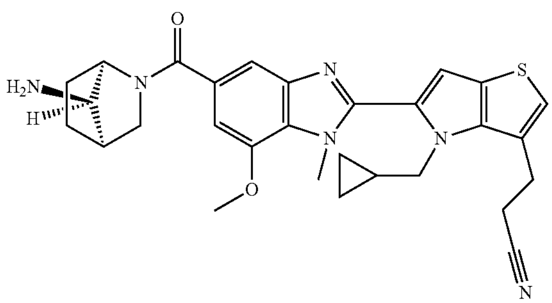 [SMILES: COc1cc(C(=O)N2C[C@H]3CC[C@@H]2[C@@H]3N)cc2nc(-c3cc4scc(CCC#N)c4n3CC3CC3)n(C)c12] | 3-(5-(5-((1R,4R,7R)-7-amino-2-azabicyclo[2.2.1]heptane-2-carbonyl)-7-methoxy-1-methyl-1H-benzo[d]imidazol-2-yl)-4-(cyclopropylmethyl)-4H-thieno[3,2-b]pyrrol-3-yl)propanenitrile | 529.2 | 1 | 1.43 |
| 16 | 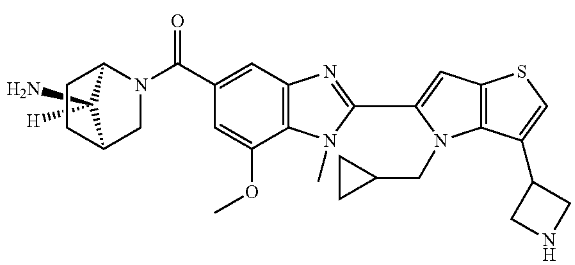 [SMILES: COc1cc(C(=O)N2C[C@H]3CC[C@@H]2[C@@H]3N)cc2nc(-c3cc4scc(C5CNC5)c4n3CC3CC3)n(C)c12] | ((1R,4R,7R)-7-amino-2-azabicyclo[2.2.1]heptan-2-yl)(2-(3-(azetidin-3-yl)-4-(cyclopropylmethyl)-4H-thieno[3,2-b]pyrrol-5-yl)-7-methoxy-1-methyl-1H-benzo[d]imidazol-5-yl)methanone | 531.4 | 1 | 1.12 |
| 17 | 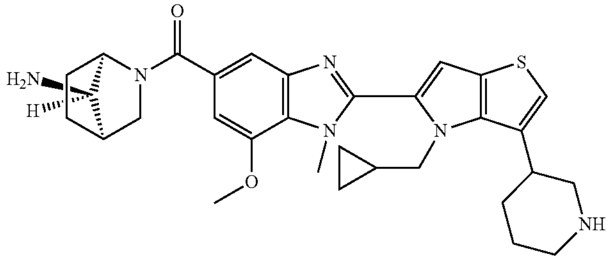 [SMILES: COc1cc(C(=O)N2C[C@H]3CC[C@@H]2[C@@H]3N)cc2nc(-c3cc4scc(C5CCCNC5)c4n3CC3CC3)n(C)c12] | ((1R,4R,7R)-7-amino-2-azabicyclo[2.2.1]heptan-2-yl)(2-(4-(cyclopropylmethyl)-3-(piperidin-3-yl)-4H-thieno[3,2-b]pyrrol-5-yl)-7-methoxy-1-methyl-1H-benzo[d]imidazol-5-yl)methanone, ISOMER 2 | 558.9 | 2 | 1.16 |

Examples 18 and 19

((1R,4R,7R)-7-amino-2-azabicyclo[2.2.1]heptan-2-yl)(2-(3-(azetidin-3-ylmethyl)-4-(cyclopropylmethyl)-4H-thieno[3,2-b]pyrrol-5-yl)-7-methoxy-1l-methyl-1H-benzo[d]imidazol-5-yl)methanone and (2-(3-(3-amino-2-(chloromethyl)propyl)-4-(cyclopropylmethyl)-4H-thieno[3,2-b]pyrrol-5-yl)-7-methoxy-1l-methyl-1H-benzo[d]imidazol-5-yl)((1R,4R,7R)-7-amino-2-azabicyclo[2.2.1]heptan-2-yl)methanone

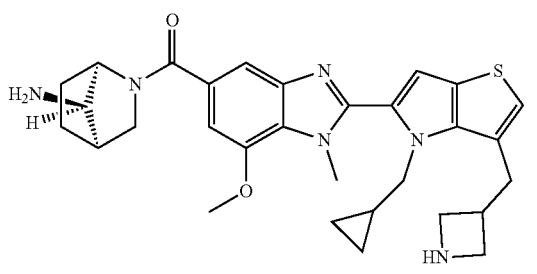

18

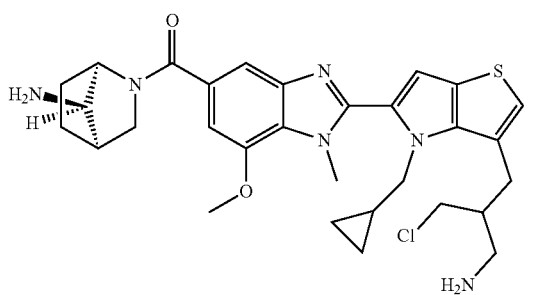

19

Intermediate 18/19A: tert-Butyl 3-((5-(5-((1R,4R,7R)-7-((tert-butoxycarbonyl)amino)-2-azabicyclo[2.2.1]heptane-2-carbonyl)-7-methoxy-1-methyl-1H-benzo[d]imidazol-2-yl)-4-(cyclopropylmethyl)-4H-thieno[3,2-b]pyrrol-3-yl)methyl)azetidine-1-carboxylate

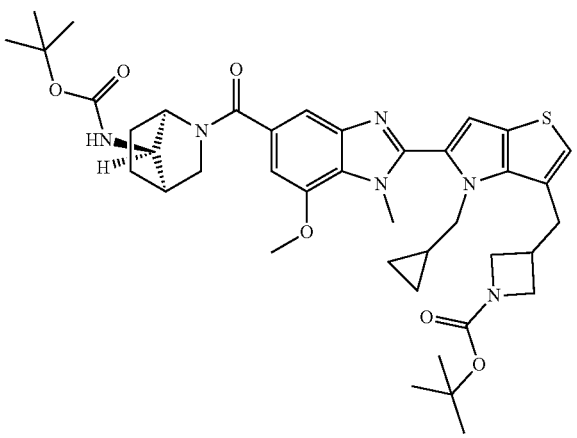 [SMILES: COc1cc(C(=O)N2C[C@H]3CC[C@@H]2[C@@H]3NC(=O)OC(C)(C)C)cc2nc(-c3cc4scc(CC5CN(C(=O)OC(C)(C)C)C5)c4n3CC3CC3)n(C)c12]

In a 2-dram vial, a stirring mixture of tert-butyl 3-(iodomethyl)azetidine-1-carboxylate (137 mg, 0.463 mmol), tert-butyl ((1R,4R,7R)-2-(2-(7-bromo-1-(cyclopropylmethyl)-1H-indol-2-yl)-7-methoxy-1-methyl-1H-benzo[d]imidazole-5-carbonyl)-2-azabicyclo[2.2.1]heptan-7-yl)carbamate (150 mg, 0.231 mmol), tris(trimethylsilyl)silane (0.107 mL, 0.347 mmol), Ir(dF(CF3)ppy)$_2$(dtbbpy)PF6 (7.78 mg, 6.94 μmol), and sodium carbonate (98 mg, 0.925 mmol) in 1,4-Dioxane (2 mL) was degassed with bubbling nitrogen for 10 minutes. In a separate vial, a stirring mixture of nickel(II) chloride ethylene glycol dimethyl ether complex (7.62 mg, 0.035 mmol), and 4,4'-di-tert-butyl-2,2'-bipyridine (10.55 mg, 0.039 mmol) in 1,4-dioxane (1 mL) was degassed with nitrogen for 20 minutes. The nickel complex was transferred to the containing the other mixture, the vial was sealed, and the reaction was stirred at room temperature under a blue Kessil lamp for 60 hours, at which point it was judged to be complete by LCMS. The mixture was diluted with dichloromethane (2 mL) and filtered, and the filtrate was used as-is in the next step. MS ESI m/z=745.5 (M+H). HPLC retention time 0.97 minutes, Method D.

Example 18 and 19

((1R,4R,7R)-7-amino-2-azabicyclo[2.2.1]heptan-2-yl)(2-(3-(azetidin-3-ylmethyl)-4-(cyclopropylmethyl)-4H-thieno[3,2-b]pyrrol-5-yl)-7-methoxy-1-methyl-1H-benzo[d]imidazol-5-yl)methanone and (2-(3-(3-amino-2-(chloromethyl)propyl)-4-(cyclopropylmethyl)-4H-thieno[3,2-b]pyrrol-5-yl)-7-methoxy-1-methyl-1H-benzo[d]imidazol-5-yl)((1R,4R,7R)-7-amino-2-azabicyclo[2.2.1]heptan-2-yl)methanone A stirring solution of tert-butyl 3-((5-(5-((1R,4R,7R)-7-((tert-butoxycarbonyl)amino)-2-azabicyclo[2.2.1]heptane-2-carbonyl)-7-methoxy-1-methyl-1H-benzo[d]imidazol-2-yl)-4-(cyclopropylmethyl)-4H-thieno[3,2-b]pyrrol-3-yl)methyl)azetidine-1-carboxylate (56.6 mg, 0.076 mmol) in 1:1 dichloromethane/dioxane (4 mL) was treated with 4M HCl in dioxane (2 ml, 8.00 mmol). The reaction was stirred at room temperature for 2 hours, at which point it was judged to be complete by LCMS. Two products were detected—the desired azetidine (m/z=545), and HCl addition/ring opening product (m/z=581). The mixture was concentrated in vacuo. The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 10% B, 10-50% B over 20 minutes, then a 4-minute hold at 100% B; Flow Rate: 20 mL/min; Column Temperature: 25 C. Fraction collection was triggered by UV signals. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation to yield:

Example 18: (3.3 mg, 5.69 μmol, 7.49% yield). $^1$H NMR (500 MHz, DMSO-d$_6$) δ 7.42-7.30 (m, 1H), 7.02-6.88 (m, 3H), 4.45 (br d, J=6.1 Hz, 2H), 4.16 (br s, 1H), 4.07 (br s, 3H), 3.98 (br s, 3H), 3.78 (br d, J=6.4 Hz, 1H), 3.49-3.16 (m, 4H), 3.06 (br d, J=11.0 Hz, 1H), 2.99 (s, 1H), 2.28-2.14 (m, 1H), 2.05-1.83 (m, 2H), 1.82-1.71 (m, 1H), 1.45 (br s, 1H), 1.38 (br s, 1H), 1.23 (br s, 2H), 1.02-0.82 (m, 3H), 0.26 (br s, 2H), −0.24 (br s, 2H). MS ESI m/z=545.5 (M+H). HPLC retention time 0.94 minutes, Method 2.

Example 19: (11.8 mg, 0.020 mmol, 26.5% yield). $^1$H NMR (500 MHz, DMSO-d$_6$) δ 7.19-7.07 (m, 1H), 6.99-6.85 (m, 1H), 6.76-6.61 (m, 2H), 4.18 (br t, J=7.2 Hz, 2H), 3.95 (br t, J=9.6 Hz, 1H), 3.83 (br d, J=4.1 Hz, 3H), 3.74 (br s, 3H), 3.60 (br s, 3H), 3.40 (br d, J=10.4 Hz, 1H), 3.02 (br d, J=7.1 Hz, 1H), 2.93-2.83 (m, 1H), 2.74 (br d, J=5.6 Hz, 1H), 2.60-2.47 (m, 1H), 2.19-2.07 (m, 1H), 1.78-1.52 (m, 3H), 1.38-1.20 (m, 1H), 1.00 (br s, 1H), 0.79-0.56 (m, 2H), 0.03 (br d, J=4.4 Hz, 2H), −0.49 (br s, 2H). (Proton count is low due to the water suppression algorithm used during data processing). MS ESI m/z=581.4 (M+H). HPLC retention time 1.31 minutes, Method 1.

Example 20

((1R,4R,7R)-7-amino-2-azabicyclo[2.2.1]heptan-2-yl)(2-(4-(cyclopropylmethyl)-3-(2-azaspiro[3.3]heptan-6-yl)-4H-thieno[3,2-b]pyrrol-5-yl)-7-methoxy-1-methyl-1H-benzo[d]imidazol-5-yl)methanone

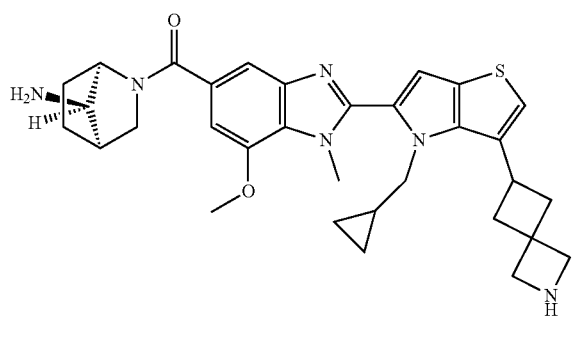 [SMILES: COc1cc(C(=O)N2C[C@H]3CC[C@@H]2[C@@H]3N)cc2nc(-c3cc4scc(C5CC6(CNC6)C5)c4n3CC3CC3)n(C)c12]

Intermediate 20A: tert-Butyl 6-(tosyloxy)-2-azaspiro[3.3]heptane-2-carboxylate

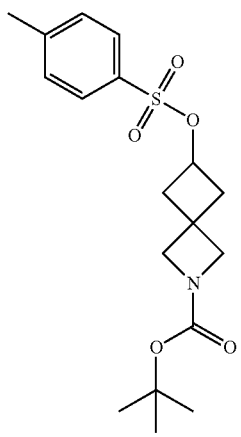 [SMILES: Cc1ccc(S(=O)(=O)OC2CC3(C2)CN(C(=O)OC(C)(C)C)C3)cc1]

In a 20 mL scintillation vial, a stirring solution of tert-butyl 6-hydroxy-2-azaspiro[3.3]heptane-2-carboxylate (291 mg, 1.364 mmol) and triethylamine (0.285 mL, 2.047 mmol) in dichloromethane (5 mL) was treated with tosyl-Cl (286 mg, 1.501 mmol) followed by DMAP (16.67 mg, 0.136 mmol). The vial was sealed, and the reaction was stirred at room temperature for 18 hours. TLC (50% EtOAc/hexane, KMnO$_4$) indicated that the reaction had not gone to completion. The mixture was treated with triethylamine (0.076 mL, 0.544 mmol) and tosyl-Cl (50 mg, 0.262 mmol), and the reaction was stirred at room temperature for 18 hours, at which point it was judged to be complete by TLC. The mixture was diluted with dichloromethane (5 mL), and washed twice with water, twice with 1M NaOH, twice with 1M HCl, and once with brine, then dried over sodium sulfate and concentrated in vacuo. The residue was chromatographed via MPLC over a 24 g silica gel column, eluting at 40 mL/min with a 5% to 50% acetone/hexanes gradient over 13 column volumes. Fractions containing the desired product were pooled and concentrated in vacuo to yield the title compound (425 mg, 1.157 mmol, 85% yield) as a colorless solid. $^1$H NMR (499 MHz, CHLOROFORM-d) δ 7.81-7.75 (m, 2H), 7.37 (d, J=8.0 Hz, 2H), 4.70 (quin, J=7.2 Hz, 1H), 3.86 (d, J=2.1 Hz, 4H), 2.54-2.46 (m, 5H), 2.36-2.28 (m, 2H), 1.42 (s, 9H).

Intermediate 20B: tert-Butyl 6-iodo-2-azaspiro[3.3]heptane-2-carboxylate

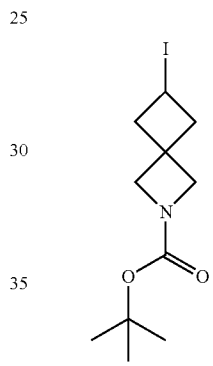

In a 2-dram vial, a solution of tert-butyl 6-(tosyloxy)-2-azaspiro[3.3]heptane-2-carboxylate (420 mg, 1.143 mmol) in methyl ethylketone (5 mL) was treated with sodium iodide (685 mg, 4.57 mmol). The vial was sealed, and the reaction was stirred at 100° C. for 3 hours, then stored in the freezer overnight. The reaction was stirred at 100° C. for 2 hours, at which point it was judged to be complete by LCMS. The mixture was diluted with dichloromethane (10 mL) and filtered, and the filtrate was concentrated in vacuo. The residue was chromatographed via MPLC over a 12 g silica gel column, eluting at 30 mL/min with a 50% to 100% ethyl acetate/hexanes gradient over 12 column volumes, then with 100% ethyl acetate. Fractions containing the desired product were pooled and concentrated in vacuo to yield the title compound (267 mg, 0.826 mmol, 72.3% yield). $^1$H NMR (499 MHz, chloroform-d) δ 4.31 (quin, J=7.8 Hz, 1H), 3.96 (d, J=15.1 Hz, 4H), 2.99-2.89 (m, 2H), 2.77-2.68 (m, 2H), 1.45 (s, 9H).

Example 20

((1R,4R,7R)-7-amino-2-azabicyclo[2.2.1]heptan-2-yl)(2-(4-(cyclopropylmethyl)-3-(2-azaspiro[3.3]heptan-6-yl)-4H-thieno[3,2-b]pyrrol-5-yl)-7-methoxy-1-methyl-1H-benzo[d]imidazol-5-yl)methanone The title compound was prepared from tert-butyl ((1R,4R,7R)-2-(2-(3-bromo-4-(cyclopropylmethyl)-4H-thieno[3, 2-b]pyrrol-5-yl)-7-methoxy-1-methyl-1H-benzo[d]imidazole-5-carbonyl)-2-azabicyclo[2.2.1]heptan-7-yl)carbamate and tert-butyl 6-iodo-2-azaspiro[3.3]heptane-2-carboxylate using the procedure described in Example 2. $^1$H NMR (500 MHz, DMSO-$d_6$) δ 7.28-7.04 (m, 1H), 6.95 (s, 1H), 6.78-6.64 (m, 2H), 4.14 (br d, J=6.6 Hz, 2H), 3.92 (s, 2H), 3.84 (s, 3H), 3.76 (s, 3H), 3.74 (s, 2H), 3.51-3.33 (m, 2H), 3.32-3.04 (m, 1H), 2.99-2.91 (m, 1H), 2.60-2.49 (m, 2H), 2.27 (br s, 9H), 1.71 (br s, 3H), 0.62 (br s, 1H), 0.01 (br d, J=7.8 Hz, 2H), -0.48 (br s, 2H). MS ESI m/z=571.2 (M+H). HPLC retention time 1.14 minutes, Method 2.

Examples 21 and 22

((1R,4R,7R)-7-amino-2-azabicyclo[2.2.1]heptan-2-yl)(2-(4-(cyclopropylmethyl)-3-(3-hydroxycyclobutyl)-4H-thieno[3,2-b]pyrrol-5-yl)-7-methoxy-1-methyl-1H-benzo[d]imidazol-5-yl)methanone, isomer1 and isomer 2

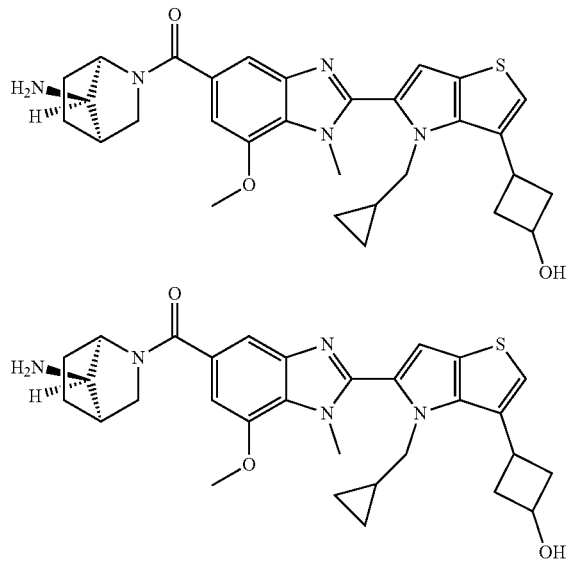

The isomeric mixture of cis trans-((1R,4R,7R)-7-amino-2-azabicyclo[2.2.1]heptan-2-yl)(2-(4-(cyclopropylmethyl)-3-(3-hydroxycyclobutyl)-4H-thieno[3,2-b]pyrrol-5-yl)-7-methoxy-1-methyl-1H-benzo[d]imidazol-5-yl)methanone in Example 7 was separated via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 16% B, 16-56% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The material was further purified via preparative LC/MS with the following conditions: Column: XBridge C18, 200 mm×30 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 3% B, 3-43% B over 20 minutes, then a 2-minute hold at 100% B; Flow Rate: 45 mL/min; Column Temperature: 25 C. Fraction collection was triggered by MS and UV signals. The resolved isomers were handled separately for the remaining steps of the process. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation.

Example 21 (First-eluting): $^1$H NMR (500 MHz, DMSO-$d_6$) δ 7.43-7.25 (m, 1H), 7.09 (s, 1H), 6.90 (s, 2H), 4.40 (br d, J=6.4 Hz, 2H), 4.22-4.12 (m, 1H), 4.07 (s, 3H), 3.98 (s, 3H), 3.90-3.71 (m, 1H), 3.66-3.43 (m, 2H), 3.37 (s, 1H), 3.24-3.14 (m, 1H), 3.07 (br d, J=11.3 Hz, 1H), 2.79-2.68 (m, 2H), 2.28-2.13 (m, 1H), 2.10-1.94 (m, 4H), 1.81-1.66 (m, 1H), 1.52-1.35 (m, 1H), 1.32-1.22 (m, 1H), 0.85 (br d, J=5.1 Hz, 1H), 0.24 (br d, J=7.9 Hz, 2H), -0.27 (br s, 2H). MS ESI m/z=546.3 (M+H). HPLC retention time 1.13 minutes, Method 2.

Example 22 (Second-eluting): $^1$H NMR (500 MHz, DMSO-$d_6$) δ 7.31-7.11 (m, 1H), 7.07-6.96 (m, 2H), 6.95-6.64 (m, 3H), 4.34-4.04 (m, 3H), 4.01-3.83 (m, 3H), 3.77 (br s, 3H), 3.59-3.35 (m, 2H), 3.21 (br s, 1H), 3.07-2.89 (m, 1H), 2.75-2.45 (m, 1H), 2.20-2.05 (m, 2H), 1.91-1.61 (m, 4H), 1.53-1.30 (m, 1H), 1.02 (br s, 1H), 0.63 (br d, J=6.7 Hz, 1H), 0.01 (br d, J=7.3 Hz, 2H), -0.54 (br d, J=6.4 Hz, 2H). MS ESI m/z=546.1 (M+H). HPLC retention time 1.61 minutes, Method 1.

Example 23

1-(3-(5-(5-((1R,4R,7R)-7-amino-2-azabicyclo[2.2.1]heptane-2-carbonyl)-7-methoxy-1-methyl-1H-benzo[d]imidazol-2-yl)-4-(cyclopropylmethyl)-4H-thieno[3,2-b]pyrrol-3-yl)azetidin-1-yl)ethan-1-one

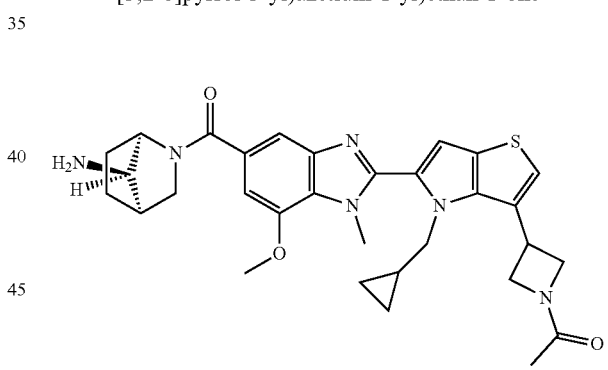

A stirring solution of ((1R,4R,7R)-7-amino-2-azabicyclo[2.2.1]heptan-2-yl)(2-(3-(azetidin-3-yl)-4-(cyclopropylmethyl)-4H-thieno[3,2-b]pyrrol-5-yl)-7-methoxy-1-methyl-1H-benzo[d]imidazol-5-yl)methanone (26 mg, 0.049 mmol) (Table 1, Example 16) and triethylamine (0.014 mL, 0.098 mmol) in dichloromethane (2 mL) was cooled to 0° C. and treated with acetic anhydride (4.62 μl, 0.049 mmol). The reaction was allowed to come to room temperature and stirred for 2 hours, at which point it was judged to be complete by LCMS based on the absence of starting material. The mixture was concentrated n vacuo. The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 6% B, 6-46% B over 20 minutes, then a 4-minute hold at 100% B; Flow Rate: 20 mL/min; Column Temperature: 25 C. Fraction collection was triggered by UV signals. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation to yield the title compound (10.7 mg, 0.019 mmol, 38.1% yield). $^1$H NMR (500 MHz, DMSO-$d_6$) δ 7.27-7.07 (m, 2H), 6.78-6.66 (m, 2H), 4.39-4.25 (m, 1H), 4.14-4.05 (m, 4H), 4.01 (br d, J=7.6 Hz, 1H), 3.84 (br s, 3H), 3.80-3.70 (m, 4H), 3.57-3.32 (m, 1H), 3.28-3.11 (m, 2H), 2.94 (br d, J=9.8 Hz, 1H), 2.40 (br s, 1H), 1.78-1.63 (m, 3H), 1.58 (s, 3H), 1.48-1.34 (m, 1H), 0.69-0.57 (m, 1H), 0.01 (br d, J=7.3 Hz, 2H), −0.52 (br s, 2H). MS ESI m/z=573.3 (M+H). HPLC retention time 1.30 minutes, Method 2.

Example 24

((1R,4R,7R)-7-Amino-2-azabicyclo[2.2.1]heptan-2-yl)(2-(2-bromo-4-(cyclopropylmethyl)-4H-thieno[3,2-b]pyrrol-5-yl)-7-methoxy-1-methyl-1H-benzo[d]imidazol-5-yl)methanone

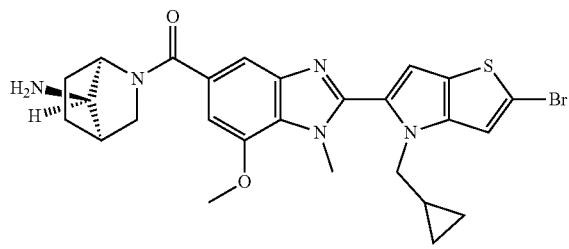 [SMILES: COc1cc(C(=O)N2C[C@H]3CC[C@@H]2[C@@H]3N)cc2nc(-c3cc4sc(Br)cc4n3CC3CC3)n(C)c12]

Intermediate 24A: tert-Butyl ((1R,4R,7R)-2-(2-(2-bromo-4-(cyclopropylmethyl)-4H-thieno[3,2-b]pyrrol-5-yl)-7-methoxy-1-methyl-1H-benzo[d]imidazole-5-carbonyl)-2-azabicyclo[2.2.1]heptan-7-yl)carbamate

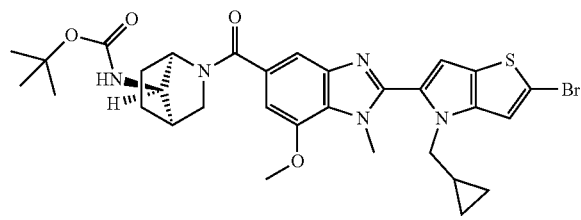 [SMILES: COc1cc(C(=O)N2C[C@H]3CC[C@@H]2[C@@H]3NC(=O)OC(C)(C)C)cc2nc(-c3cc4sc(Br)cc4n3CC3CC3)n(C)c12]

The title compound was synthesized from ethyl 2-bromo-4H-thieno[3,2-b]pyrrole-5-carboxylate by the procedures in Example 1. MS ESI m/z 654/656.3 (M+H). Analytical LC/MS retention time: 1.00 min. (Method D).

Example 24

((1R,4R,7R)-7-Amino-2-azabicyclo[2.2.1]heptan-2-yl)(2-(2-bromo-4-(cyclopropylmethyl)-4H-thieno[3,2-b]pyrrol-5-yl)-7-methoxy-1-methyl-1H-benzo[d]imidazol-5-yl)methanone tert-Butyl ((1R,4R,7R)-2-(2-(2-bromo-4-(cyclopropylmethyl)-4H-thieno[3,2-b]pyrrol-5-yl)-7-methoxy-1-methyl-1H-benzo[d]imidazole-5-carbonyl)-2-azabicyclo[2.2.1]heptan-7-yl)carbamate was dissolved in dioxane and reacted with 4H HCl in dioxane as described in Example 1, step 6. After workup the crude product was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 40% B, 40-80% B over 20 minutes, then a 4-minute hold at 100% B; Flow Rate: 20 mL/min; Column Temperature: 25 C. Fraction collection was triggered by UV signals. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation. The yield of the product from the last step was 14.2 mg, and its estimated purity by LC/MS analysis was 100.0% (Method 1) and 99.2% (Method 2). MS ESI m/z 554.09 (M+H). $^1$H NMR (500 MHz, DMSO-d6) δ 7.51 (s, 1H), 7.36-7.28 (m, 1H), 7.28 (br s, 1H), 6.86 (s, 2H), 4.25 (br s, 2H), 4.02 (s, 3H), 3.99-3.88 (m, 3H), 3.71 (br s, 1H), 3.47 (br d, J=8.8 Hz, 1H), 3.02 (br d, J=10.9 Hz, 1H), 2.21-2.06 (m, 1H), 1.98-1.88 (m, 2H), 1.68 (br s, 1H), 1.39 (br s, 1H), 1.30-1.11 (m, 1H), 1.04 (br s, 2H), 0.30 (br d, J=7.7 Hz, 2H), 0.07 (br s, 2H). Analytical LC/MS retention time: 1.50 min (Method 2).

Example 25

((1R,4R,7R)-7-Amino-2-azabicyclo[2.2.1]heptan-2-yl)(2-(4-(cyclopropylmethyl)-2-(pyridin-4-yl)-4H-thieno[3,2-b]pyrrol-5-yl)-7-methoxy-1-methyl-1H-benzo[d]imidazol-5-yl)methanone

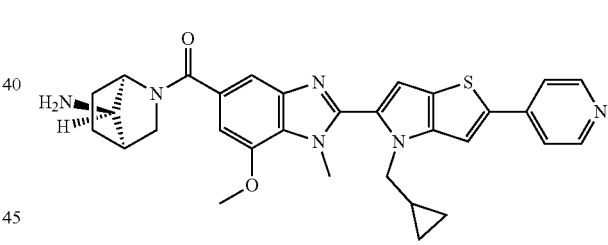

tert-Butyl (2-(2-(2-bromo-4-(cyclopropylmethyl)-4H-thieno[3,2-b]pyrrol-5-yl)-7-methoxy-1-methyl-1H-benzo[d]imidazole-5-carbonyl)-2-azabicyclo[2.2.1]heptan-7-yl)carbamate (25 mg, 0.038 mmol), pyridin-4-ylboronic acid (4.69 mg, 0.038 mmol), PdCl$_2$(dppf) (2.79 mg, 3.82 μmol), and dioxane (2 mL) were mixed and sparged with argon for 5 min. 2M K$_2$HPO$_4$ (0.050 mL, 0.099 mmol) was added and the vial was capped and warmed to 85° C. for 4 hours. LC/MS detects the formation of desired intermediate with a (M+H)+=653.40. The reaction was filtered and concentrated. The residue was dissolved in dioxane (2 mL) and 4N HCl in dioxane (0.116 mL, 0.463 mmol) was added thereto and stirred at rt for 2 hours until LC/MS detected no starting material, only product with a (M+H)+=553.30. The reaction was concentrated 5 times from methylene chloride to remove traces of HCl yielding an amber oil. The crude material was purified via preparative LC/MS with the following conditions: Column: XBridge C18, 200 mm×19 mm, 5-μm particles; Mobile Phase A: 5:95 acetonitrile: water with 10-mM ammonium acetate; Mobile Phase B: 95:5 acetonitrile: water with 10-mM ammonium acetate; Gradient: a 0-minute hold at 21% B, 21-61% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation. The yield of the product was 6.8 mg, and its estimated purity by LCMS analysis was 92.8% (Method 1) and 92.1% (Method 2). MS ESI m/z 553.14 (M+H). $^1$H NMR (500 MHz, DMSO-d6) δ 7.96-7.79 (m, 2H), 7.36-7.27 (m, 2H), 7.20-6.94 (m, 2H), 6.84 (s, 2H), 4.26 (br s, 2H), 4.09-3.95 (m, 3H), 3.95-3.83 (m, 3H), 3.11-3.02 (m, 3H), 2.85-2.64 (m, 2H), 1.96-1.72 (m, 3H), 1.50-1.36 (m, 1H), 1.32-1.20 (m, 1H), 1.06-0.74 (m, 4H), 0.30 (br d, J=7.9 Hz, 2H), 0.08-0.02 (in, 2H). Analytical LC/MS retention time: 1.10 min (Method 2).

The following compounds in Table 2 were synthesized by the procedures in Examples 1, 24 and 25 employing the appropriate starting materials.

TABLE 2

| Ex # | Structure | Name | LC/MS Rt (min) | LC/MS Method | M + H (obsion) |
|---|---|---|---|---|---|
| 26 | 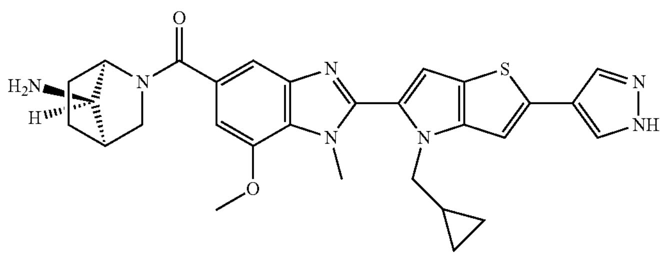 [SMILES: COc1cc(C(=O)N2C[C@H]3CC[C@@H]2[C@@H]3N)cc2nc(-c3cc4sc(-c5cn[nH]c5)cc4n3CC3CC3)n(C)c12] | ((1R,4R,7R)-7-amino-2-azabicyclo[2.2.1]heptan-2-yl)(2-(4-(cyclopropylmethyl)-2-(1H-pyrazol-4-yl)-4H-thieno[3,2-b]pyrrol-5-yl)-7-methoxy-1-methyl-1H-benzo[d]imidazol-5-yl)methanone | 1.49 | 1 | 541.88 |
| 27 | 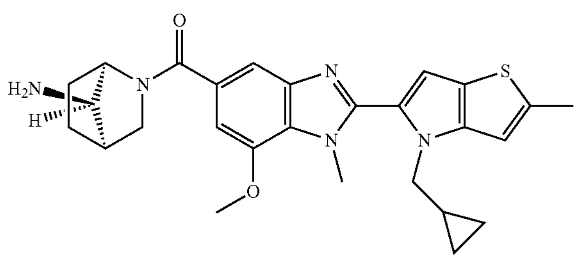 [SMILES: COc1cc(C(=O)N2C[C@H]3CC[C@@H]2[C@@H]3N)cc2nc(-c3cc4sc(C)cc4n3CC3CC3)n(C)c12] | ((1R,4R,7R)-7-amino-2-azabicyclo[2.2.1]heptan-2-yl)(2-(4-(cyclopropylmethyl)-2-methyl-4H-thieno[3,2-b]pyrrol-5-yl)-7-methoxy-1-methyl-1H-benzo[d]imidazol-5-yl)methanone | 1.83 | 1 | 490.03 |
| 28 | 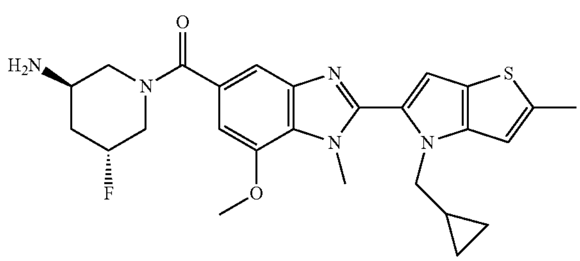 [SMILES: COc1cc(C(=O)N2C[C@H](N)C[C@@H](F)C2)cc2nc(-c3cc4sc(C)cc4n3CC3CC3)n(C)c12] | ((3R,5R)-3-amino-5-fluoropiperidin-1-yl)(2-(4-(cyclopropylmethyl)-2-methyl-4H-thieno[3,2-b]pyrrol-5-yl)-7-methoxy-1-methyl-1H-benzo[d]imidazol-5-yl)methanone | 1.77 | 1 | 496.24 |
| 29 | 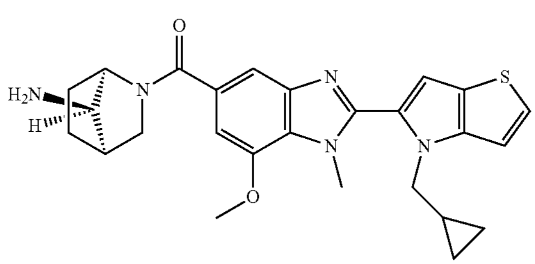 [SMILES: COc1cc(C(=O)N2C[C@H]3CC[C@@H]2[C@@H]3N)cc2nc(-c3cc4sccc4n3CC3CC3)n(C)c12] | ((1R,4R,7R)-7-amino-2-azabicyclo[2.2.1]heptan-2-yl)(2-(4-(cyclopropylmethyl)-4H-thieno[3,2-b]pyrrol-5-yl)-7-methoxy-1-methyl-1H-benzo[d]imidazol-5-yl)methanone | 1.62 | 1 | 476.37 |

TABLE 2-continued

| Ex # | Structure | Name | LC/MS Rt (min) | LC/MS Method | M + H (obsion) |
|---|---|---|---|---|---|
| 30 | 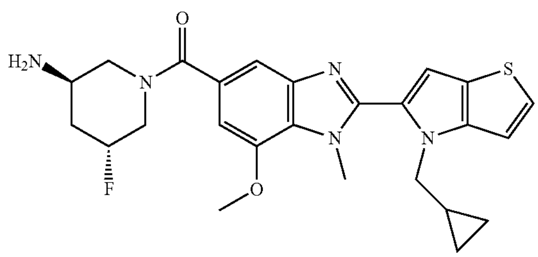 [SMILES: COc1cc(C(=O)N2C[C@H](N)C[C@@H](F)C2)cc2nc(-c3cc4sccc4n3CC3CC3)n(C)c12] | ((3R,5R)-3-amino-5-fluoropiperidin-1-yl)(2-(4-(cyclopropylmethyl)-4H-thieno[3,2-b]pyrrol-5-yl)-7-methoxy-1-methyl-1H-benzo[d]imidazol-5-yl)methanone | 1.61 | 1 | 482.38 |
| 31 | 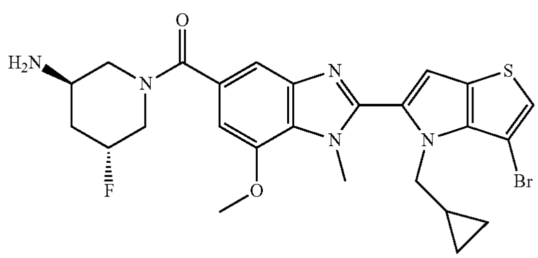 [SMILES: COc1cc(C(=O)N2C[C@H](N)C[C@@H](F)C2)cc2nc(-c3cc4scc(Br)c4n3CC3CC3)n(C)c12] | ((3R,5R)-3-amino-5-fluoropiperidin-1-yl)(2-(3-bromo-4-(cyclopropylmethyl)-4H-thieno[3,2-b]pyrrol-5-yl)-7-methoxy-1-methyl-1H-benzo[d]imidazol-5-yl)methanone | 1.75 | 1 | 560.28 |
| 32 | 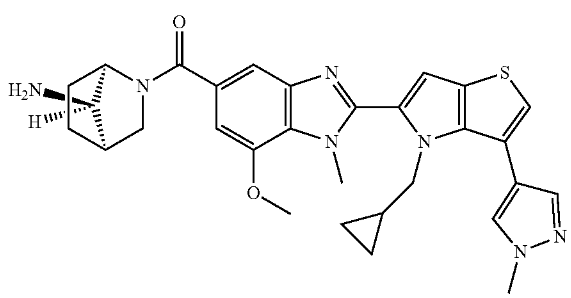 [SMILES: COc1cc(C(=O)N2C[C@H]3CC[C@@H]2[C@@H]3N)cc2nc(-c3cc4scc(-c5cnn(C)c5)c4n3CC3CC3)n(C)c12] | ((1R,4R,7R)-7-amino-2-azabicyclo[2.2.1]heptan-2-yl)(2-(4-(cyclopropylmethyl)-3-(1-methyl-1H-pyrazol-4-yl)-4H-thieno[3,2-b]pyrrol-5-yl)-7-methoxy-1-methyl-1H-benzo[d]imidazol-5-yl)methanone | 1.62 | 1 | 556.32 |
| 33 | 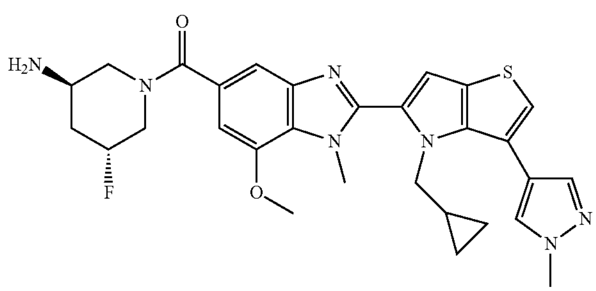 [SMILES: COc1cc(C(=O)N2C[C@H](N)C[C@@H](F)C2)cc2nc(-c3cc4scc(-c5cnn(C)c5)c4n3CC3CC3)n(C)c12] | ((3R,5R)-3-amino-5-fluoropiperidin-1-yl)(2-(4-(cyclopropylmethyl)-3-(1-methyl-1H-pyrazol-4-yl)-4H-thieno[3,2-b]pyrrol-5-yl)-7-methoxy-1-methyl-1H-benzo[d]imidazol-5-yl)methanone | 1.60 | 1 | 562.33 |
| 34 | 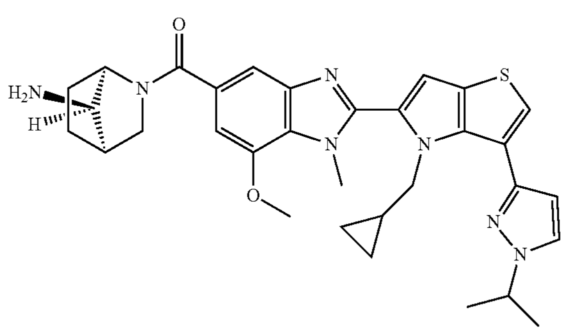 [SMILES: COc1cc(C(=O)N2C[C@H]3CC[C@@H]2[C@@H]3N)cc2nc(-c3cc4scc(-c5ccn(C(C)C)n5)c4n3CC3CC3)n(C)c12] | ((1R,4R,7R)-7-amino-2-azabicyclo[2.2.1]heptan-2-yl)(2-(4-(cyclopropylmethyl)-3-(1-isopropyl-1H-pyrazol-3-yl)-4H-thieno[3,2-b]pyrrol-5-yl)-7-methoxy-1-methyl-1H-benzo[d]imidazol-5-yl)methanone | 1.88 | 1 | 584.21 |

TABLE 2-continued

| Ex # | Structure | Name | LC/MS Rt (min) | LC/MS Method | M + H (obsion) |
|---|---|---|---|---|---|
| 35 | 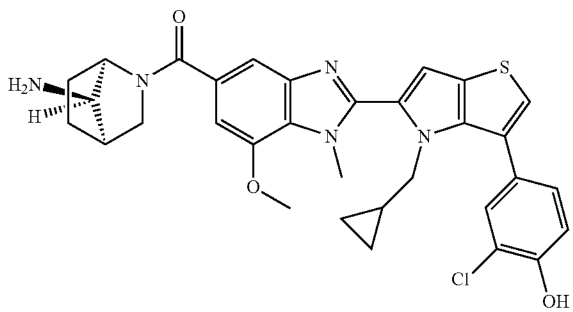 [SMILES: COc1cc(C(=O)N2C[C@H]3CC[C@@H]2[C@@H]3N)cc2nc(-c3cc4scc(-c5ccc(O)c(F)c5)c4n3CC3CC3)n(C)c12] | ((1R,4R,7R)-7-amino-2-azabicyclo[2.2.1]heptan-2-yl)(2-(3-(3-chloro-4-hydroxyphenyl)-4-(cyclopropylmethyl)-4H-thieno[3,2-b]pyrrol-5-yl)-7-methoxy-1-methyl-1H-benzo[d]imidazol-5-yl)methanone | 2.07 | 1 | 601.98 |
| 36 | 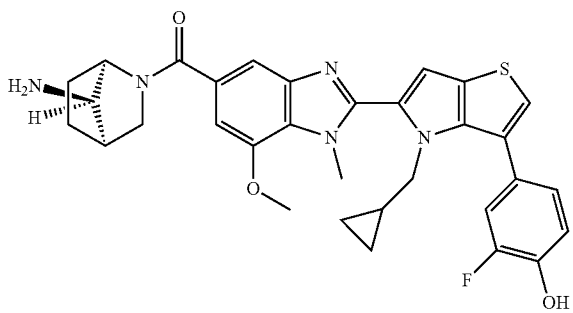 | ((1R,4R,7R)-7-amino-2-azabicyclo[2.2.1]heptan-2-yl)(2-(4-(cyclopropylmethyl)-3-(3-fluoro-4-hydroxyphenyl)-4H-thieno[3,2-b]pyrrol-5-yl)-7-methoxy-1-methyl-1H-benzo[d]imidazol-5-yl)methanone | 1.95 | 1 | 586.24 |
| 37 | 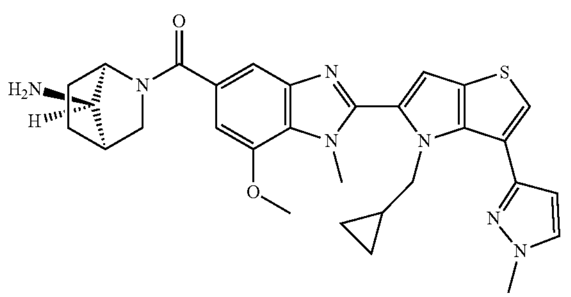 [SMILES: COc1cc(C(=O)N2C[C@H]3CC[C@@H]2[C@@H]3N)cc2nc(-c3cc4scc(-c5ccn(C)n5)c4n3CC3CC3)n(C)c12] | ((1R,4R,7R)-7-amino-2-azabicyclo[2.2.1]heptan-2-yl)(2-(4-(cyclopropylmethyl)-3-(1-methyl-1H-pyrazol-3-yl)-4H-thieno[3,2-b]pyrrol-5-yl)-7-methoxy-1-methyl-1H-benzo[d]imidazol-5-yl)methanone | 1.73 | 1 | 556.19 |
| 38 | 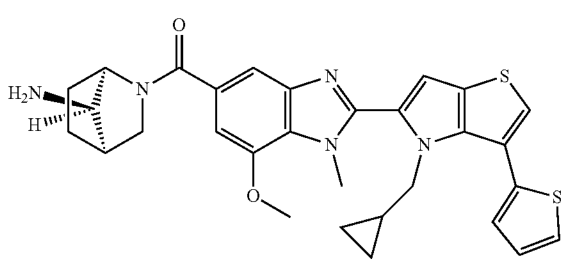 [SMILES: COc1cc(C(=O)N2C[C@H]3CC[C@@H]2[C@@H]3N)cc2nc(-c3cc4scc(-c5cccs5)c4n3CC3CC3)n(C)c12] | ((1R,4R,7R)-7-amino-2-azabicyclo[2.2.1]heptan-2-yl)(2-(4-(cyclopropylmethyl)-3-(thiophen-2-yl)-4H-thieno[3,2-b]pyrrol-5-yl)-7-methoxy-1-methyl-1H-benzo[d]imidazol-5-yl)methanone | 2.10 | 1 | 558.15 |
| 39 | 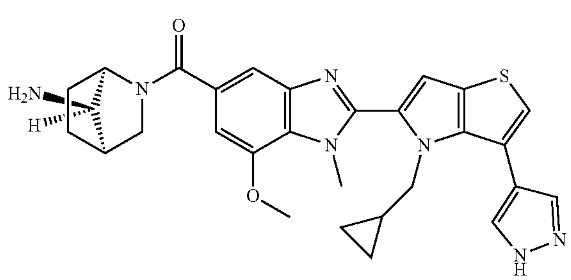 [SMILES: COc1cc(C(=O)N2C[C@H]3CC[C@@H]2[C@@H]3N)cc2nc(-c3cc4scc(-c5cn[nH]c5)c4n3CC3CC3)n(C)c12] | ((1R,4R,7R)-7-amino-2-azabicyclo[2.2.1]heptan-2-yl)(2-(4-(cyclopropylmethyl)-3-(1H-pyrazol-4-yl)-4H-thieno[3,2-b]pyrrol-5-yl)-7-methoxy-1-methyl-1H-benzo[d]imidazol-5-yl)methanone | 1.49 | 1 | 548.38 |

TABLE 2-continued

| Ex # | Structure | Name | LC/MS Rt (min) | LC/MS Method | M + H (obsion) |
|---|---|---|---|---|---|
| 40 | 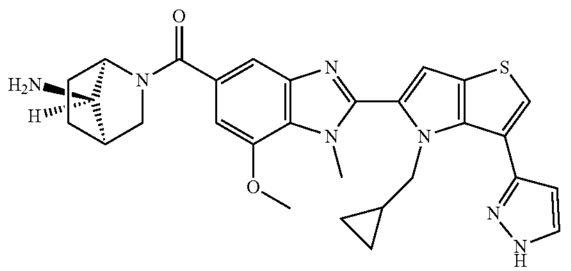 [SMILES: COc1cc(C(=O)N2C[C@H]3CC[C@@H]2[C@@H]3N)cc2nc(-c3cc4scc(-c5cc[nH]n5)c4n3CC3CC3)n(C)c12] | ((1R,4R,7R)-7-amino-2-azabicyclo[2.2.1]heptan-2-yl)(2-(4-(cyclopropylmethyl)-3-(1H-pyrazol-3-yl)-4H-thieno[3,2-b]pyrrol-5-yl)-7-methoxy-1-methyl-1H-benzo[d]imidazol-5-yl)methanone | 1.59 | 1 | 542.06 |
| 41 | 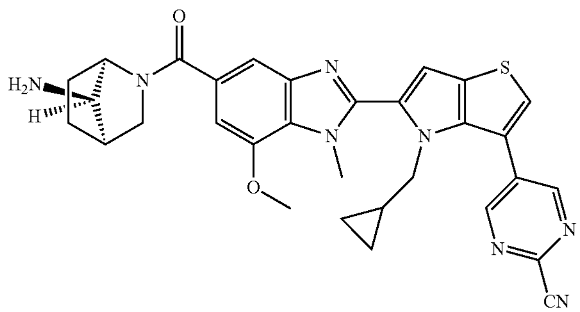 [SMILES: COc1cc(C(=O)N2C[C@H]3CC[C@@H]2[C@@H]3N)cc2nc(-c3cc4scc(-c5cnc(C#N)nc5)c4n3CC3CC3)n(C)c12] | 5-(5-(5-((1R,4R,7R)-7-amino-2-azabicyclo[2.2.1]heptane-2-carbonyl)-7-methoxy-1-methyl-1H-benzo[d]imidazol-2-yl)-4-(cyclopropylmethyl)-4H-thieno[3,2-b]pyrrol-3-yl)pyrimidine-2-carbonitrile | 1.62 | 1 | 579.35 |
| 42 | 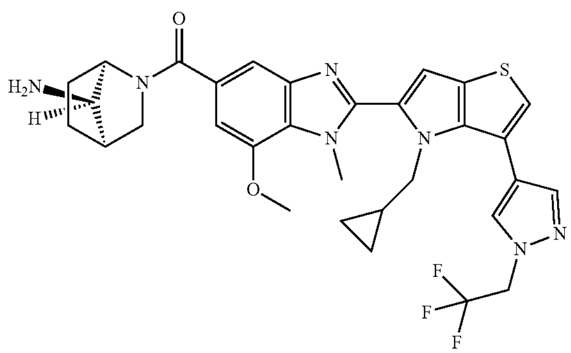 [SMILES: COc1cc(C(=O)N2C[C@H]3CC[C@@H]2[C@@H]3N)cc2nc(-c3cc4scc(-c5cnn(CC(F)(F)F)c5)c4n3CC3CC3)n(C)c12] | ((1R,4R,7R)-7-amino-2-azabicyclo[2.2.1]heptan-2-yl)(2-(4-(cyclopropylmethyl)-3-(1-(2,2,2-trifluoroethyl)-1H-pyrazol-4-yl)-4H-thieno[3,2-b]pyrrol-5-yl)-7-methoxy-1-methyl-1H-benzo[d]imidazol-5-yl)methanone | 1.80 | 1 | 624.16 |
| 43 | 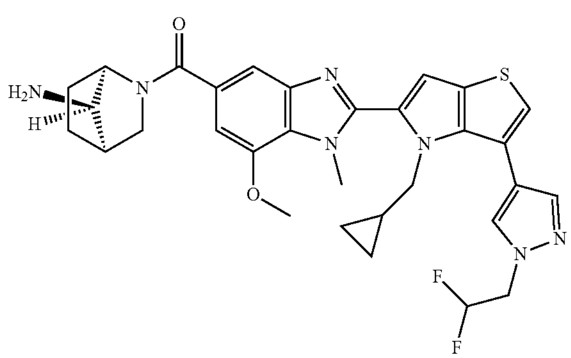 [SMILES: COc1cc(C(=O)N2C[C@H]3CC[C@@H]2[C@@H]3N)cc2nc(-c3cc4scc(-c5cnn(CC(F)F)c5)c4n3CC3CC3)n(C)c12] | ((1R,4R,7R)-7-amino-2-azabicyclo[2.2.1]heptan-2-yl)(2-(4-(cyclopropylmethyl)-3-(1-(2,2-difluoroethyl)-1H-pyrazol-4-yl)-4H-thieno[3,2-b]pyrrol-5-yl)-7-methoxy-1-methyl-1H-benzo[d]imidazol-5-yl)methanone | 1.61 | 1 | 606.37 |
| 44 | 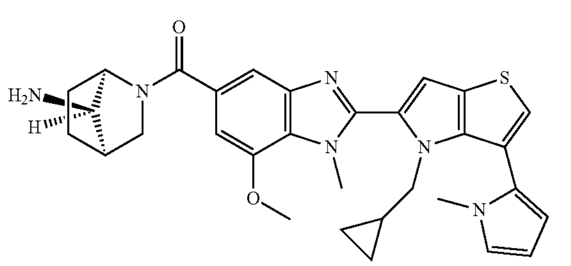 [SMILES: COc1cc(C(=O)N2C[C@H]3CC[C@@H]2[C@@H]3N)cc2nc(-c3cc4scc(-c5cccn5C)c4n3CC3CC3)n(C)c12] | ((1R,4R,7R)-7-amino-2-azabicyclo[2.2.1]heptan-2-yl)(2-(4-(cyclopropylmethyl)-3-(1-methyl-1H-pyrrol-2-yl)-4H-thieno[3,2-b]pyrrol-5-yl)-7-methoxy-1-methyl-1H-benzo[d]imidazol-5-yl)methanone | 1.93 | 1 | 555.36 |

TABLE 2-continued

| Ex # | Structure | Name | LC/MS Rt (min) | LC/MS Method | M + H (obsion) |
|---|---|---|---|---|---|
| 45 | 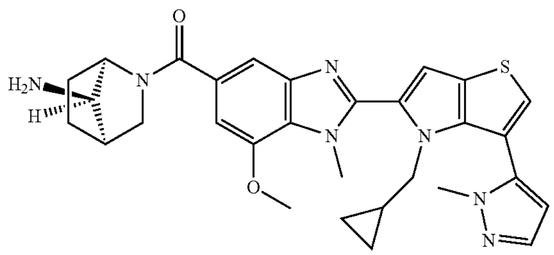 [SMILES: COc1cc(C(=O)N2C[C@H]3CC[C@@H]2[C@@H]3N)cc2nc(-c3cc4scc(-c5ccnn5C)c4n3CC3CC3)n(C)c12] | ((1R,4R,7R)-7-amino-2-azabicyclo[2.2.1]heptan-2-yl)(2-(4-(cyclopropylmethyl)-3-(1-methyl-1H-pyrazol-5-yl)-4H-thieno[3,2-b]pyrrol-5-yl)-7-methoxy-1-methyl-1H-benzo[d]imidazol-5-yl)methanone | 1.62 | 1 | 556.12 |
| 46 | 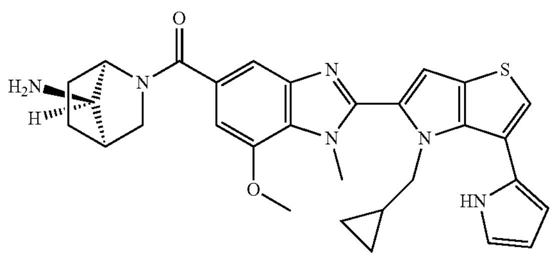 [SMILES: COc1cc(C(=O)N2C[C@H]3CC[C@@H]2[C@@H]3N)cc2nc(-c3cc4scc(-c5ccc[nH]5)c4n3CC3CC3)n(C)c12] | ((1R,4R,7R)-7-amino-2-azabicyclo[2.2.1]heptan-2-yl)(2-(4-(cyclopropylmethyl)-3-(1H-pyrrol-2-yl)-4H-thieno[3,2-b]pyrrol-5-yl)-7-methoxy-1-methyl-1H-benzo[d]imidazol-5-yl)methanone | 1.80 | 1 | 541.08 |
| 47 | 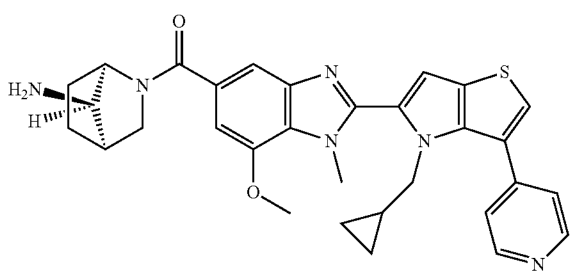 [SMILES: COc1cc(C(=O)N2C[C@H]3CC[C@@H]2[C@@H]3N)cc2nc(-c3cc4scc(-c5ccncc5)c4n3CC3CC3)n(C)c12] | ((1R,4R,7R)-7-amino-2-azabicyclo[2.2.1]heptan-2-yl)(2-(4-(cyclopropylmethyl)-3-(pyridin-4-yl)-4H-thieno[3,2-b]pyrrol-5-yl)-7-methoxy-1-methyl-1H-benzo[d]imidazol-5-yl)methanone | 1.53 | 1 | 553.39 |
| 48 | 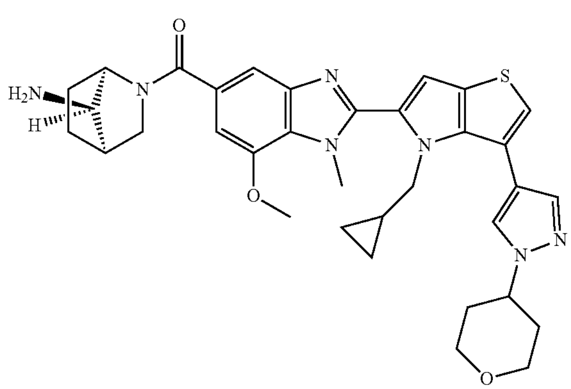 [SMILES: COc1cc(C(=O)N2C[C@H]3CC[C@@H]2[C@@H]3N)cc2nc(-c3cc4scc(-c5cnn(C6CCOCC6)c5)c4n3CC3CC3)n(C)c12] | ((1R,4R,7R)-7-amino-2-azabicyclo[2.2.1]heptan-2-yl)(2-(4-(cyclopropylmethyl)-3-(1-(tetrahydro-2H-pyran-4-yl)-1H-pyrazol-4-yl)-4H-thieno[3,2-b]pyrrol-5-yl)-7-methoxy-1-methyl-1H-benzo[d]imidazol-5-yl)methanone | 1.70 | 1 | 626.10 |

Example 49

((1R,4R,7R)-7-Amino-2-azabicyclo[2.2.1]heptan-2-yl)(2-(4-(cyclopropylmethyl)-3-(pyridin-4-ylamino)-4H-thieno[3,2-b]pyrrol-5-yl)-7-methoxy-1-methyl-1H-benzo[d]imidazol-5-yl)methanone

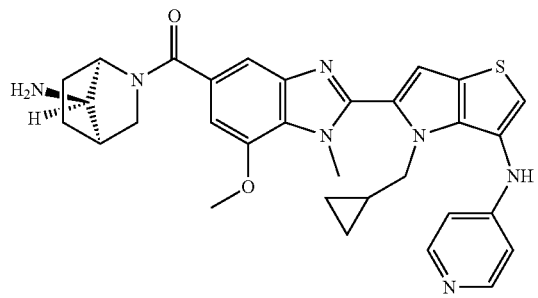 [SMILES: COc1cc(C(=O)N2C[C@H]3CC[C@@H]2[C@@H]3N)cc2nc(-c3cc4scc(Nc5ccncc5)c4n3CC3CC3)n(C)c12]

A mixture of tert-butyl ((1R,4R,7R)-2-(2-(3-bromo-4-(cyclopropylmethyl)-4H-thieno[3,2-b]pyrrol-5-yl)-7-methoxy-1-methyl-1H-benzo[d]imidazole-5-carbonyl)-2-azabicyclo[2.2.1]heptan-7-yl)carbamate (25 mg, 0.038 mmol), pyridin-4-amine (5.03 mg, 0.053 mmol), $Cs_2CO_3$ (37.3 mg, 0.115 mmol) in 1,4-dioxane was degassed via bubbling nitrogen for 10 min. Xantphos (4.42 mg, 7.64 μmol) was then added, followed by $Pd_2(dba)_3$ (3.50 mg, 3.82 μmol) and the reaction mixture stirred at 110° C. for 16 hours. LC/MS detects $(M+H)^+=668.40$ for intermediate product showing the reaction to be essentially complete. The reaction was filtered and concentrated to yield an amber oil. This intermediate was then dissolved in 1,4-dioxane (2 mL) and 4N HCl in dioxane (0.018 mL, 0.073 mmol) was added thereto. The contents were stirred at rt for 2 hours after which LC/MS detected product. Workup entailed concentrating the reaction 5 times from methylene chloride to yield an amber oil. The crude material was purified via preparative LC/MS with the following conditions: Column: XBridge C18, 200 mm×19 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: a 0-minute hold at 0% B, 0-35% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation. The purified material was then diluted with DMF, treated with Si-Pyridine and shaken for a minimum of 2 h. The resulting mixture was filtered and dried via centrifugal evaporation. The yield of the product was 7.9 mg, and its estimated purity by LCMS analysis was 100.0% (Method 1); Observed Mass: 568.16; Retention Time: 1.42 min. and 97.0% (Method 2). MS ESI m/z 568.16 (M+H). $^1$H NMR (500 MHz, DMSO-d6) δ 8.24 (br d, J=6.7 Hz, 2H), 7.48 (s, 1H), 7.29 (s, 1H), 7.04-6.81 (m, 4H), 4.20-4.07 (m, 2H), 4.05-3.97 (m, 2H), 3.94-3.85 (m, 2H), 3.65 (br d, J=7.3 Hz, 2H), 3.16-3.04 (m, 1H), 2.92-2.80 (m, 2H), 2.00-1.87 (m, 1H), 1.86-1.76 (m, 2H), 1.67-1.50 (m, 1H), 1.22-1.05 (m, 4H), 1.01-0.80 (m, 1H), 0.72 (br d, J=5.2 Hz, 1H), 0.15-0.01 (m, 2H), −0.30--0.44 (m, 2H). Analytical LC/MS retention time: 1.42 min (Method 1).

Biological Assays

Compounds of the present invention were assayed as inhibitors of PAD4 using the assay protocol described below.

RFMS Human PAD4 Functional Assay:

Compounds were solubilized in 100% DMSO to achieve a10 mM compound concentration. Compound stock solutions were stored at RT. A series of dilutions were prepared in DMSO and mixed 8 times with 20 μL mixing volume. Final top concentration of compound in the assay is 50 μM. Final assay conditions were as follows:

Reaction volume: 26 μl
Assay buffer: 25 mM hepes, pH 7.5, 5 mM NaCl, 1 mM DTT, 0.2 mg/ml BSA, 0.01% CHAPS, 50 μM Calcium, and 5 μM TPEN
Final concentrations: 5 nM hPAD4 enzyme, 250 μM BAEE, and 0.5% DMSO
Total incubation time: 30 mins compound and enzyme preincubation at 37° C., 90 min enzyme/substrate reaction, 30 min reaction with phenyl glyoxal at 37° C.
Stop solution: 40 μl 5% TCA in ACN 0.13 μL of compound solution was added to 13 μL of 10 nM PAD4 in assay buffer. After 30 min 13 μl of 500 μM of BAEE was added in 25 mM hepes, pH 7.5, 5 mM NaCl, 1 mM DTT, 0.2 mg/ml BSA, 0.01% CHAPS, 50 μM Calcium, 5 μM TPEN was added and the reaction incubated for 90 min at 37° C. The enzymatic reaction was quenched by addition of 15 μl of 6.1N TCA, 100% Final Concentration is 20%, 35 μl of 8.5 mM phenyl glyoxal (final concentration 4 mM) is then added and the reaction is incubated for 30 min at 37° C.

After 30 minutes the plates are spun down to remove all precipitate. The enzyme reaction was quenched with an equal volume of methanol containing internal standard (modified citrulline). Samples were loaded onto the Rapid Fire RF300 system (Agilent) wherein they were first sipped for 1000 ms and then directly loaded to a $C_{18}$ separations cartridge using a mixture of acetonitrile containing 0.01% formic acid for 3000 ms desalting. The flow rate of the mobile phase was 1.5 ml/min. Once the samples were eluted from the cartridge, a mobile phase of acetonitrile containing 0.01% formic acid was used to move the samples into the mass spectrometer for 4000 ms at a flow rate of 1.25 ml/min/Sciex API5500 triple quadrupole mass spectrometer (Applied Biosystems) equipped with ESI was used to analyze the peptidyl citrulline and internal standard ions.

MRM transition of product and internal standard were monitored at m/z 424.5 to 350.4 and m/z 293 to 247 respectively. The dwell time for each transition was set at 200 ms, and the ESI voltage was used at 5500 with a source temperature of 400° C. Extracted ion peaks for each transition were integrated using the Rapid Fire Integrator software. Peak area of analyte was normalized with internal standard.).

For a given compound example, the Table below shows the human PAD4 (hPAD4) $IC_{50}$ in the rapid-fire mass spectrum (RFMS) assay.

TABLE 3

PAD4 Activity

| EX NO | hPAD4 RFMS $IC_{50}$ μM |
|---|---|
| 1 | 0.035 |
| 2 | 0.063 |
| 3 | 0.012 |
| 4 | 0.014 |
| 5 | 0.019 |
| 6 | 0.032 |
| 7 | 0.034 |
| 8 | 0.040 |

TABLE 3-continued

PAD4 Activity

| EX NO | hPAD4 RFMS IC$_{50}$ μM |
|---|---|
| 9 | 0.040 |
| 10 | 0.046 |
| 11 | 0.047 |
| 12 | 0.049 |
| 13 | 0.054 |
| 14 | 0.056 |
| 15 | 0.059 |
| 16 | 0.127 |
| 17 | 0.079 |
| 18 | 0.165 |
| 19 | 0.070 |
| 20 | 0.036 |
| 21 | 0.038 |
| 22 | 0.082 |
| 23 | 0.055 |
| 24 | 0.041 |
| 25 | 0.179 |
| 26 | 0.107 |
| 27 | 0.062 |
| 28 | 0.067 |
| 29 | 0.084 |
| 30 | 0.086 |
| 31 | 0.060 |
| 32 | 0.017 |
| 33 | 0.050 |
| 34 | 0.048 |
| 35 | 0.150 |
| 36 | 0.059 |
| 37 | 0.054 |
| 38 | 0.100 |
| 39 | 0.035 |
| 40 | 0.024 |
| 41 | 0.140 |
| 42 | 0.059 |
| 43 | 0.051 |
| 44 | 0.113 |
| 45 | 0.053 |
| 46 | 0.173 |
| 47 | 0.147 |
| 48 | 0.029 |
| 49 | 0.062 |

What is claimed is:

1. A compound of Formula (I):

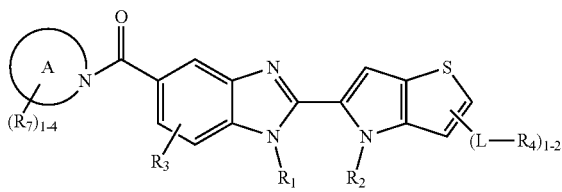

or a pharmaceutically acceptable salt thereof, wherein:

Ring A is 4- to 15-membered heterocyclyl substituted with 1-4 $R_7$;

$R_1$ is selected from $CH_3$ and $CD_3$;

$R_2$ is selected from H, $C_{1-3}$ alkyl substituted with 0-5 $R_e$, and —$(CH_2)_r$—$C_{3-6}$ cycloalkyl with 0-5 $R_e$;

$R_3$ is selected from F, Cl, Br, and —$OR_b$;

L is selected from —$(CR_dR_d)_{0-3}$—, —$NR_a$—, —$S(O)_p$—, and —$C(=O)$—;

$R_4$ is selected from H, F, Cl, Br, —CN, —$OR_b$, $C_{1-6}$ alkyl substituted with 1-5 $R_5$, aryl substituted with 1-5 $R_5$, $C_{3-12}$ cycloalkyl substituted with 1-5 $R_5$, and heterocyclyl comprising carbon atoms and 1-3 heteroatoms selected from N, $NR_6$, O, and S and substituted with 1-5 $R_5$;

$R_5$, at each occurrence, is independently selected from H, F, Cl, Br, nitro, =O, —$C_{1-4}$alkyl substituted with 0-4 $R_e$, $C_{2-4}$alkenyl substituted with 0-4 $R_e$, $C_{2-4}$alkynyl substituted with 0-4 $R_e$, —$(CH_2)_r$CN, —$(CH_2)_rOR_b$, —$(CH_2)_sS(O)_pR_c$, —$(CH_2)_sS(O)_pNR_aR_a$, —$(CH_2)_rNR_aS(O)_pR_c$, —$(CH_2)_rNR_aR_a$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$(CH_2)_rOC(=O)R_b$, —$(CH_2)_rC(=O)NR_aR_a$, —$P(=O)(OC_{1-4}alkyl)_2$, —$P(=O)(C_{1-4}alkyl)_2$, $C_{3-6}$cycloalkyl substituted with 0-4 $R_e$, aryl substituted with 0-4 $R_e$, heterocyclyl substituted with 0-4 $R_e$, and heteroaryl substituted with 0-4 $R_e$;

$R_6$, at each occurrence, is independently selected from H, $C_{1-3}$alkyl substituted with 0-5 $R_e$, —$C(=O)R_b$, —$C(=O)(CH_2)_rNR_aR_a$, —$C(=O)(CH_2)_rNR_aC(=O)R_b$, —$C(=O)OR_b$, —$S(O)_pR_c$, —$S(O)_pNR_aR_a$, —$(CH_2)_r$—$C_{3-6}$cycloalkyl substituted with 0-4 $R_e$, —$(CH_2)_r$-aryl substituted with 0-4 $R_e$, —$(CH_2)_r$-heterocyclyl substituted with 0-4 $R_e$, and —$(CH_2)_r$-heteroaryl substituted with 0-4 $R_e$;

$R_7$ is selected from H, F, Cl, CN, $C_{1-3}$ alkyl, =N—$OR_b$, —$(CH_2)_rOR_b$, —$(CH_2)_rNR_aR_a$, —$NR_aC(=NH)C_{1-3}$ alkyl, —$NR_aC(=O)OR_b$, carbocyclyl, and a heterocyclyl; alternatively, two $R_7$ groups are taken together to form carbocyclyl or heterocyclyl;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$ alkynyl substituted with 0-5 $R_e$, —$(CH_2)_r$—$C_{3-6}$ carbocyclyl substituted with 0-5 $R_e$, and —$(CH_2)_r$-heterocyclyl substituted with 0-5 $R_e$;

$R_d$, at each occurrence, is independently selected from H and $C_{1-6}$ alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-aryl, F, Cl, Br, CN, $NO_2$, =O, —$C(=O)OH$, —$C(=O)OC_{1-4}$ alkyl, —$(CH_2)_rOH$, and —$(CH_2)_rOC_{1-4}$alkyl;

$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2;

r, at each occurrence, is independently selected from zero, 1, 2, 3, and 4; and provided when L is selected from —$NR_a$—, —$S(O)_p$—, and —$C(=O)$—, $R_4$ is selected from aryl substituted with 1-5 $R_5$, $C_{3-12}$ cycloalkyl substituted with 1-5 $R_5$, and heterocyclyl comprising carbon atoms and 1-3 heteroatoms selected from N, $NR_6$, O, and S and substituted with 1-5 $R_5$.

2. The compound according to claim 1 of Formula (II):

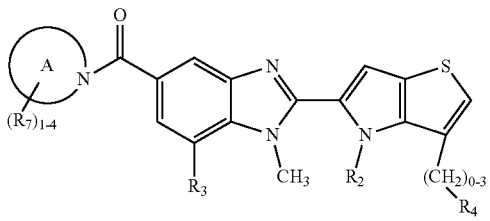
(II)

or a pharmaceutically acceptable salt thereof, wherein:

Ring A is selected from

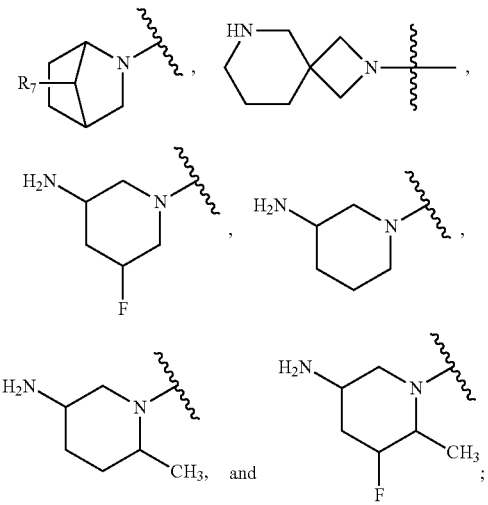

$R_2$ is selected from —$CH_3$, —$CH_2CH_3$, and —$CH_2$-cyclopropyl;

$R_3$ is selected from H, F, Cl, Br, and —$OC_{1-4}$ alkyl;

$R_4$ is selected from F, Cl, Br, $C_{1-5}$ alkyl substituted with 1-4 $R_5$,

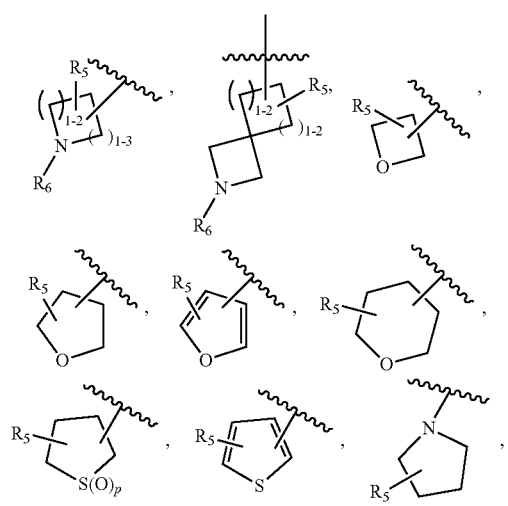

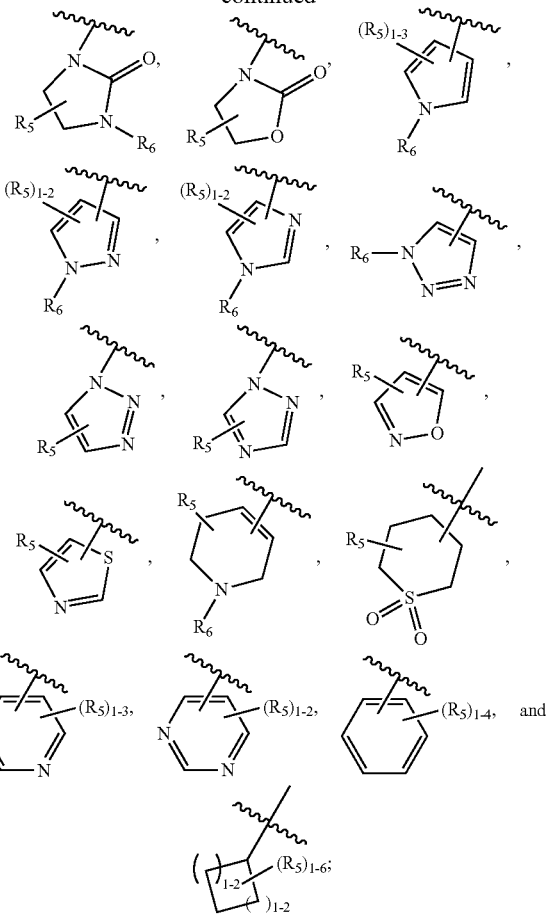

$R_5$, at each occurrence, is independently selected from H, F, Cl, Br, $C_{1-4}$alkyl, $C_{2-4}$alkenyl, $C_{2-4}$alkynyl, nitro, —CN, $OR_b$, —$S(O)_pR_c$, —$S(O)_pNR_aR_a$, —$NR_aS(O)_p$ $R_c$, —$NR_aR_a$, —$NR_aC(=O)R_b$, —$NR_aC(=O)NR_aR_a$, —$C(=O)OR_b$, —$C(=O)R_b$, —$OC(=O)R_b$, —$C(=O)NR_aR_a$, —$P(=O)(C_{1-4}alkyl)_2$, $C_{3-6}$ cycloalkyl substituted with 0-4 $R_e$, aryl substituted with 0-4 $R_e$, heterocyclyl substituted with 0-4 $R_e$, and heteroaryl substituted with 0-4 $R_e$;

$R_6$, at each occurrence, is independently selected from H, $C_{1-6}$ alkyl substituted with 0-5 $R_e$, —$C(=O)R_b$, —$C(=O)NR_aR_a$, —$C(=O)OR_b$, —$S(O)_pR_c$, —$S(O)_p$ $NR_aR_a$, —$(CH_2)_r$—$C_{3-6}$cycloalkyl substituted with 0-4 $R_e$, —$(CH_2)_r$-aryl substituted with 0-4 $R_e$, —$(CH_2)_r$-heterocyclyl substituted with 0-4 $R_e$, and —$(CH_2)_r$-heteroaryl substituted with 0-4 $R_e$;

$R_a$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-6}$ carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-aryl, F, Cl, Br, CN, $NO_2$, =O, C(=O)OH, —C(=O)$OC_{1-4}$ alkyl, —$(CH_2)_r$OH, and —$(CH_2)_r$$OC_{1-4}$alkyl;

$R_f$, at each occurrence, is independently selected from H, F, Cl, Br, CN, OH, $C_{1-5}$ alkyl optionally substituted with OH, $C_{3-6}$ cycloalkyl, and phenyl;

p, at each occurrence, is independently selected from zero, 1, and 2; and r, at each occurrence, is independently selected from zero, 1, 2, 3, and 4.

3. The compound according to claim 2 of Formula (III):

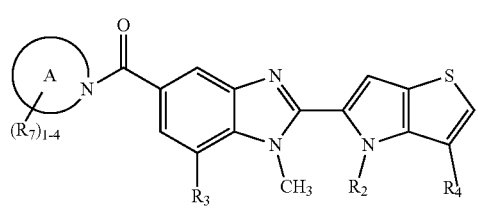

(III)

or a pharmaceutically acceptable salt thereof, wherein:
Ring A is selected from

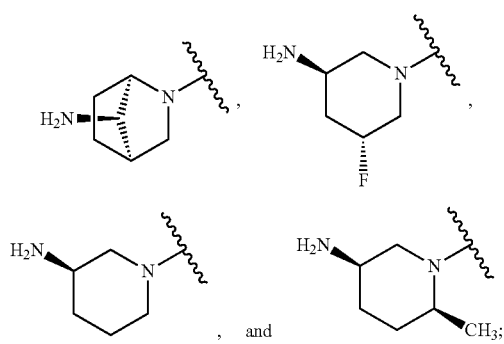

$R_2$ is selected from —$CH_3$, and —$CH_2$-cyclopropyl;
$R_3$ is -O$C_{1-4}$ alkyl;
$R_4$ is selected from

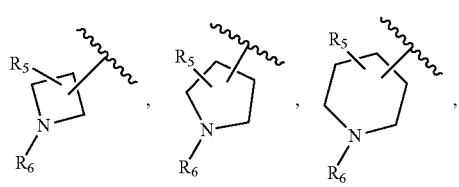

-continued

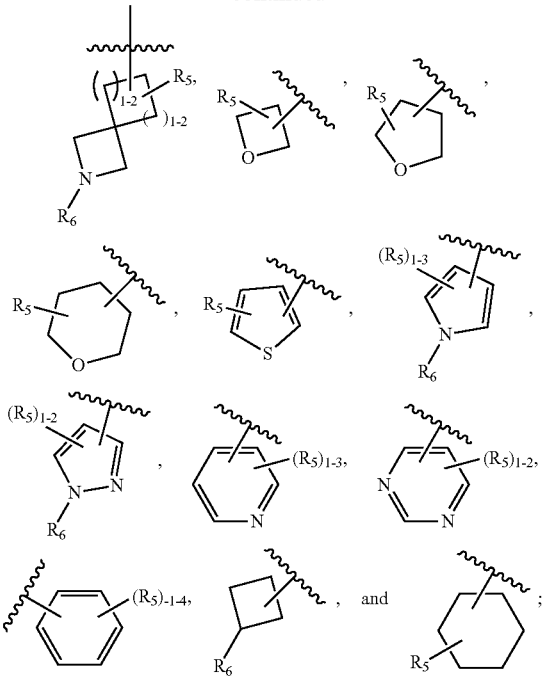

$R_5$, at each occurrence, is independently selected from H, F, Cl, Br, $C_{1-4}$alkyl, —CN, —$OR_b$, —S(O)$_p R_c$, —S(O)$_p$ $NR_a R_a$, —$NR_a$S(O)$_p R_c$, —$NR_a$C(=O)$NR_a R_a$, —C(=O)$OR_b$, —C(=O)$R_b$, —OC(=O)$R_b$, —C(=O)$NR_a R_a$, and NHC(=O)$R_b$;

$R_6$, at each occurrence, is independently selected from H, $C_{1-3}$alkyl substituted with 0-5 $R_e$, —C(=O)$R_b$, —C(=O)$OR_b$,

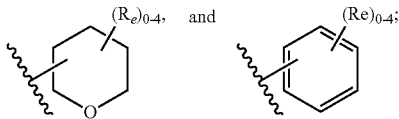

$R_a$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, —$(CH_2)_r$-aryl, F, Cl, Br;

$R_f$, at each occurrence, is independently selected from H, F, Cl, Br, CN, OH, $C_{1-5}$ alkyl optionally substituted with OH, $C_{3-6}$ cycloalkyl, and phenyl;

r, at each occurrence, is independently selected from zero, 1, 2, 3, and 4.

4. The compound according to claim 3, or a pharmaceutically acceptable salt thereof, wherein:

Ring A is

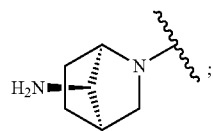

R₂ is selected from —CH₃ and —CH₂-cyclopropyl;
R₃ is —OCH₃;
R₄ is selected from

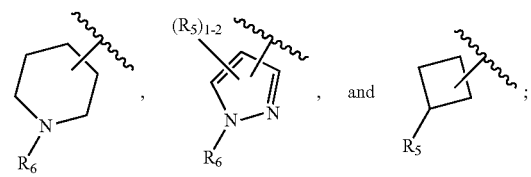

R₅, at each occurrence, is independently selected from H, C₁₋₄ alkyl, CN, OH, —C(=O)NR_aR_a, and NHC(=O)C₁₋₄ alkyl; and
R₆, at each occurrence, is independently selected from H, methyl, ethyl, and —C(=O)C₁₋₄ alkyl.

5. The compound according to claim 1 of Formula (IV):

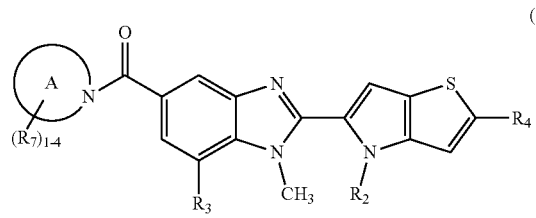

or a pharmaceutically acceptable salt thereof, wherein:
Ring A is selected from

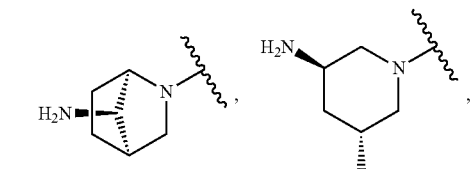

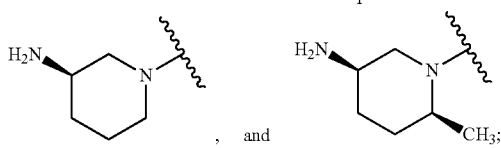

R₂ is selected from —CH₃, —CH₂CH₃, and —CH₂-cyclopropyl;
R₃ is selected from F, Cl, Br, and —OC₁₋₄ alkyl;
R₄ is selected from H, F, Cl, Br, C₁₋₃ alkyl substituted with 0-4 R_e,

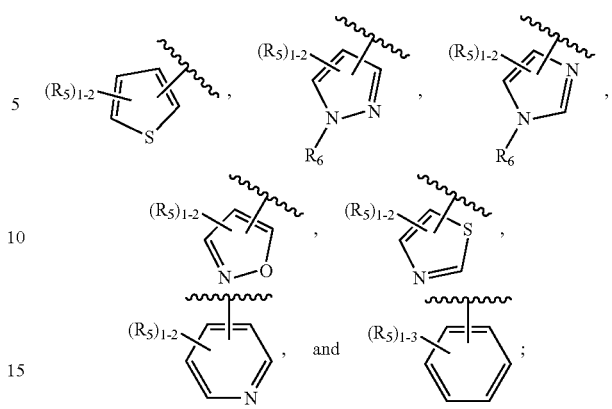

R₅, at each occurrence, is independently selected from H, F, Cl, Br, C₁₋₄alkyl;
R₆, at each occurrence, is independently selected from H, C₁₋₆ alkyl substituted with 0-5 R_e, —(CH₂)_r-aryl substituted with 0-4 R_e, and —(CH₂)_r-heterocyclyl substituted with 0-4 R_e;
R_e, at each occurrence, is independently selected from C₁₋₆ alkyl substituted with 0-5 R_f; C₂₋₆ alkenyl, C₂₋₆ alkynyl, —(CH₂)_r—C₃₋₆ cycloalkyl, —(CH₂)_r-aryl, F, Cl, Br, CN, NO₂, =O, C(=O)OH, —C(=O)OC₁₋₄ alkyl, —(CH₂)_rOH, and —(CH₂)_rOC₁₋₄alkyl;
R_f, at each occurrence, is independently selected from H, F, Cl, Br, CN, OH, C₁₋₅ alkyl optionally substituted with OH, C₃₋₆ cycloalkyl, and phenyl; and
r, at each occurrence, is independently selected from zero, 1, 2, 3, and 4.

6. The compound according to claim 5 or a pharmaceutically acceptable salt thereof, wherein:
Ring A is selected from

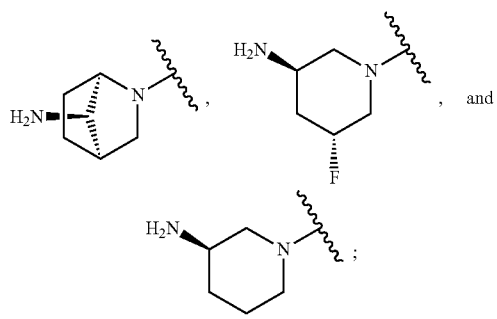

R₂ is —CH₂-cyclopropyl;
R₃ is –OC₁₋₄ alkyl;
R₄ is selected from H, F, Cl, Br, C₁₋₃ alkyl,

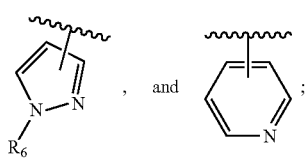

and
R₆ is selected from H and C₁₋₃ alkyl.

7. The compound according to claim 2 or a pharmaceutically acceptable salt thereof, wherein:

L is —(CHR$_a$)$_0$—;

R$_4$ is C$_{1-5}$ alkyl substituted with 1-3 R$_5$;

R$_5$, at each occurrence, is independently selected from H, F, Cl, Br, C$_{1-4}$alkyl, —OR$_b$, —CN, —NR$_a$R$_a$, and —C(=O)NR$_a$R$_a$;

R$_a$, at each occurrence, is independently selected from H, and C$_{1-6}$ alkyl; and R$_b$, at each occurrence, is independently selected from H and C$_{1-6}$ alkyl.

8. The compound according to claim 1 of Formula (V)

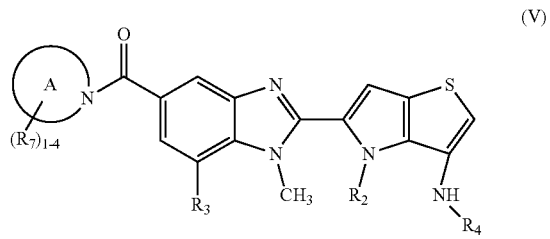

(V)

or a pharmaceutically acceptable salt thereof, wherein:
Ring A is selected from

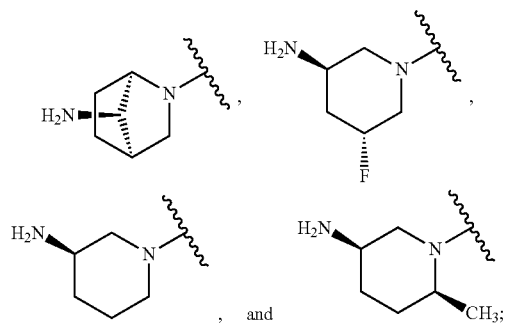

R$_2$ is selected from —CH$_3$ and —CH$_2$-cyclopropyl;

R$_3$ is —OC$_{1-4}$ alkyl;

R$_4$ is selected from

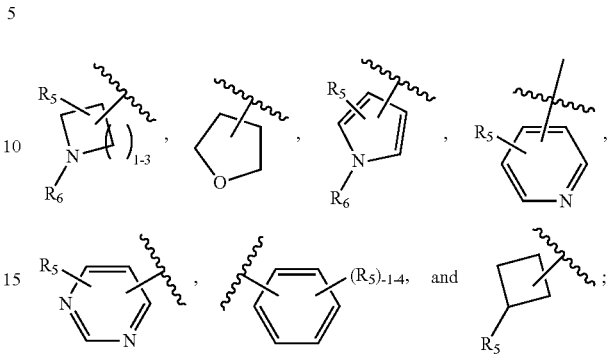

R$_5$, at each occurrence, is independently selected from H, F, Cl, Br, C$_{1-4}$alkyl, —CN, —OR$_b$, —C(=O)NR$_a$R$_a$, and NHC(=O)R$_b$;

R$_6$, at each occurrence, is independently selected from H, C$_{1-3}$ alkyl, —C(=O)R$_b$, and —C(=O)OR$_b$;

R$_a$, at each occurrence, is independently selected from H, and C$_{1-6}$ alkyl; and R$_b$, at each occurrence, is independently selected from H and C$_{1-6}$ alkyl.

9. A pharmaceutically acceptable composition comprising the compound according to claim 1, and a pharmaceutically acceptable carrier, adjuvant, or vehicle.

10. The composition according to claim 9 in combination with an additional therapeutic agent.

11. A method of inhibiting PAD4 in a subject or in a biological sample comprising a step of contacting the PAD4 with a compound according to claim 1.

* * * * *